(12) United States Patent
Seo et al.

(10) Patent No.: US 10,305,044 B2
(45) Date of Patent: May 28, 2019

(54) HETEROCYCLIC COMPOUND, LIGHT-EMITTING ELEMENT, LIGHT-EMITTING DEVICE, ELECTRONIC DEVICE, AND LIGHTING DEVICE

(71) Applicant: Semiconductor Energy Laboratory Co., Ltd., Kanagawa-ken (JP)

(72) Inventors: Satoshi Seo, Kanagawa (JP); Yuko Kubota, Kanagawa (JP); Tatsuyoshi Takahashi, Kanagawa (JP); Satomi Mitsumori, Kanagawa (JP)

(73) Assignee: Semiconductor Energy Laboratory Co., Ltd. (JP)

( * ) Notice: Subject to any disclaimer, the term of this patent is extended or adjusted under 35 U.S.C. 154(b) by 410 days.

(21) Appl. No.: 15/097,520

(22) Filed: Apr. 13, 2016

(65) Prior Publication Data

US 2016/0308139 A1    Oct. 20, 2016

(30) Foreign Application Priority Data

Apr. 14, 2015    (JP) ................................. 2015-082469

(51) Int. Cl.
*H01L 51/00*    (2006.01)
*C07D 403/14*    (2006.01)
(Continued)

(52) U.S. Cl.
CPC ........ *H01L 51/0067* (2013.01); *C07D 401/14* (2013.01); *C07D 403/14* (2013.01);
(Continued)

(58) Field of Classification Search
CPC .................................................. H01L 51/0067
See application file for complete search history.

(56) References Cited

U.S. PATENT DOCUMENTS 8,790,794 B2    7/2014 Osaka et al.
8,968,888 B2    3/2015 Kawata et al.
(Continued)

FOREIGN PATENT DOCUMENTS

JP    2006-188493 A    7/2006
JP    2009-035524 A    2/2009
KR    1020110132721    * 12/2011

OTHER PUBLICATIONS

Machine Translation of KR1020110132721 (Year: 2011).*
(Continued)

*Primary Examiner* — Michael M Dollinger
(74) *Attorney, Agent, or Firm* — Husch Blackwell LLP

(57) ABSTRACT

A novel heterocyclic compound is provided. A highly efficient and reliable light-emitting element is provided. The heterocyclic compound is represented by a general formula (G1).

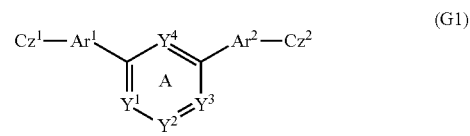

(G1)

In the general formula (G1), any one, two, or three of $Y^1$ to $Y^4$ in a ring A represent N atoms, and the rest of $Y^1$ to $Y^4$ represents CH. In the case where any two or three of the $Y^1$ to $Y^4$ are N atoms, the N atoms are not next to each other. Further, $Ar^1$ represents a substituted or unsubstituted biphenyldiyl group, $Ar^2$ represents a substituted or unsubstituted biphenyldiyl group, $Cz^1$ represents a substituted or unsubstituted heterocyclic group including a carbazole skeleton, $Cz^2$ represents a substituted or unsubstituted heterocyclic (Continued)

group including a carbazole skeleton, the carbazole skeleton included in the $Cz^1$ is directly bonded to the $Ar^1$, and the carbazole skeleton included in the $Cz^2$ is directly bonded to the $Ar^2$.

25 Claims, 37 Drawing Sheets

(51) Int. Cl.
*C09K 11/06* (2006.01)
*C07D 401/14* (2006.01)
*H01L 51/50* (2006.01)

(52) U.S. Cl.
CPC .......... C09K 11/06 (2013.01); H01L 51/0072 (2013.01); *C09K 2211/1007* (2013.01); *C09K 2211/1029* (2013.01); *C09K 2211/1044* (2013.01); *H01L 51/5016* (2013.01); *H01L 51/5072* (2013.01); *H01L 2251/5338* (2013.01); *H01L 2251/5361* (2013.01)

(56) References Cited

U.S. PATENT DOCUMENTS

| | | |
|---|---|---|
| 2005/0221123 A1 | 10/2005 | Inoue et al. |
| 2007/0129545 A1 | 6/2007 | Inoue et al. |
| 2007/0244320 A1 | 10/2007 | Inoue et al. |
| 2008/0318525 A1 | 12/2008 | Tanabe |
| 2009/0015143 A1 | 1/2009 | Inoue et al. |
| 2009/0236973 A1* | 9/2009 | Yabe .................... C07D 401/14 313/504 |
| 2010/0105902 A1 | 4/2010 | Inoue et al. |
| 2011/0082296 A1 | 4/2011 | Inoue et al. |
| 2011/0248246 A1 | 10/2011 | Ogita et al. |
| 2012/0061707 A1 | 3/2012 | Seo et al. |
| 2012/0098417 A1 | 4/2012 | Inoue et al. |
| 2013/0088144 A1 | 4/2013 | Inoue et al. |
| 2013/0204003 A1* | 8/2013 | Osaka ................. H01L 51/0072 546/276.7 |
| 2013/0324721 A1 | 12/2013 | Inoue et al. |
| 2014/0291645 A1 | 10/2014 | Inoue et al. |
| 2014/0339526 A1 | 11/2014 | Inoue et al. |
| 2016/0013421 A1 | 1/2016 | Inoue et al. |
| 2016/0343954 A1* | 11/2016 | Seo ..................... H01L 51/0067 |

OTHER PUBLICATIONS

Su, S-J. et al., "RGB Phosphorescent Organic Light-Emitting Diodes by Using Host Materials with Heterocyclic Cores:Effect of Nitrogen Atom Orientations," Chemistry of Materials, 2011, vol. 23, No. 2, pp. 274-284.

* cited by examiner

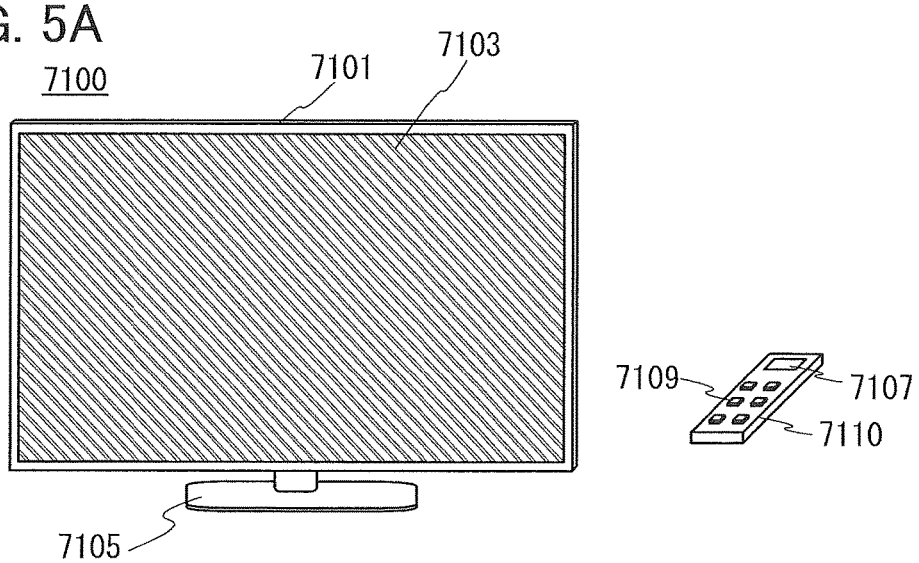
FIG. 5A
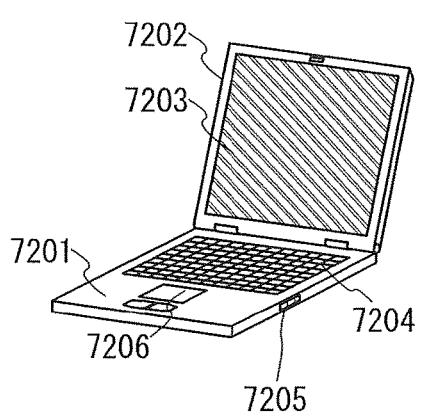
FIG. 5B
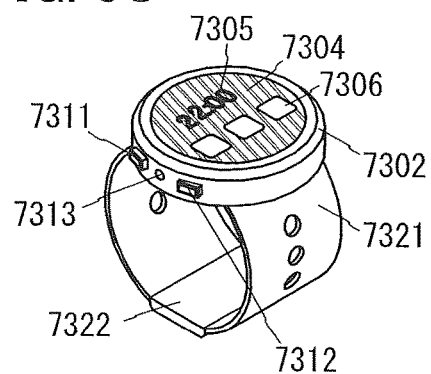
FIG. 5C
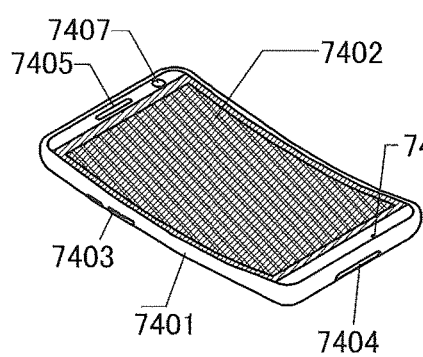
FIG. 5D
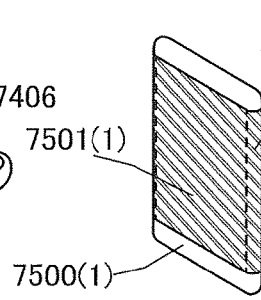
FIG. 5D'1
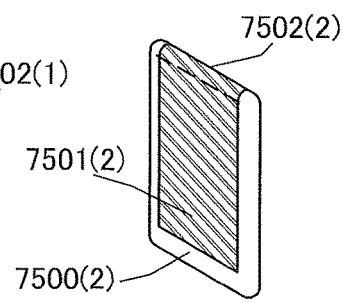
FIG. 5D'2

HETEROCYCLIC COMPOUND, LIGHT-EMITTING ELEMENT, LIGHT-EMITTING DEVICE, ELECTRONIC DEVICE, AND LIGHTING DEVICE

BACKGROUND OF THE INVENTION

1. Field of the Invention

One embodiment of the present invention relates to an object, a method, or a manufacturing method. In addition, the present invention relates to a process, a machine, manufacture, or a composition of matter. In particular, one embodiment of the present invention relates to a semiconductor device, a display device, a light-emitting device, a driving method thereof, or a manufacturing method thereof. Further, one embodiment of the present invention relates to a heterocyclic compound and a novel method for synthesizing the heterocyclic compound. In addition, one embodiment of the present invention relates to a light-emitting element, a light-emitting device, an electronic device, and a lighting device that include the heterocyclic compound. Note that one embodiment of the present invention is not limited to the above technical field. Specific examples of the technical field of one embodiment of the present invention disclosed in this specification include a semiconductor device, a display device, a liquid crystal display device, a power storage device, a memory device, an imaging device, a method for driving any of them, and a method for manufacturing any of them.

2. Description of the Related Art

A light-emitting element using an organic compound as a luminous body, which has features such as thinness, lightness, high-speed response, and DC drive at low voltage, is expected to be applied to a next-generation flat panel display. A display device in which light-emitting elements are arranged in matrix is, in particular, considered to have advantages in a wide viewing angle and excellent visibility over a conventional liquid crystal display device.

It is said that the light emission mechanism of a light-emitting element is as follows: when a voltage is applied between a pair of electrodes with an EL layer including a luminous body provided therebetween, electrons injected from the cathode and holes injected from the anode recombine in the light emission center of the EL layer to form molecular excitons, and energy is released and light is emitted when the molecular excitons relax to the ground state. A singlet excited state and a triplet excited state are known as excited states, and it is thought that light emission can be achieved through either of the excited states.

An organic compound is mainly used in an EL layer in such a light-emitting element and greatly affects an improvement in the characteristics of the light-emitting element. For this reason, a variety of novel organic compounds have been developed (e.g., Patent Documents 1 and 2).

REFERENCE

Patent Document

[Patent Document 1] Japanese Published Patent Application No. 2006-188493
[Patent Document 2] Japanese Published Patent Application No. 2009-35524

SUMMARY OF THE INVENTION

In Patent Documents 1 and 2, novel materials for light-emitting elements, that is, heteroaromatic rings such as pyridine or pyrimidine each having a plurality of substituents or a plurality of carbazolyl groups have been reported.

Specifically, for example, an organic compound having a structure in which a heteroaromatic ring is provided with three or more substituents including a carbazolyl group is disclosed in Patent Document 1. Further, an organic compound having a structure in which a carbazolyl group is bonded to a heteroaromatic ring via a phenyl group is disclosed, for example, in Patent Document 2.

However, light-emitting elements using such organic compounds with those structures are still insufficient in terms of element characteristics such as emission efficiency and reliability.

In view of the above, one embodiment of the present invention provides a novel heterocyclic compound. In particular, one embodiment of the present invention provides a novel heterocyclic compound which can serve as a host material capable of being used in combination with a phosphorescent material (dopant) that emits blue light. Another embodiment of the present invention provides a novel heterocyclic compound with high emission efficiency. Another embodiment of the present invention provides a novel heterocyclic compound with long emission life. Another embodiment of the present invention provides a novel heterocyclic compound that can be used in a light-emitting element. Another embodiment of the present invention provides a novel heterocyclic compound that can be used in an EL layer of a light-emitting element. Another embodiment of the present invention provides a novel light-emitting element. Another embodiment of the present invention provides an efficient light-emitting element. Another embodiment of the present invention provides a reliable light-emitting element. Another embodiment of the present invention provides a novel light-emitting device, a novel electronic device, or a novel lighting device. Note that the descriptions of these objects do not disturb the existence of other objects. In one embodiment of the present invention, there is no need to achieve all of these objects. Other objects will be apparent from and can be derived from the description of the specification, the drawings, the claims, and the like.

One embodiment of the present invention is a compound in which a ring structure including nitrogen is bonded to a heterocyclic group including a carbazole skeleton via an arylene group.

One embodiment of the present invention is a heterocyclic compound represented by a general formula (G1).

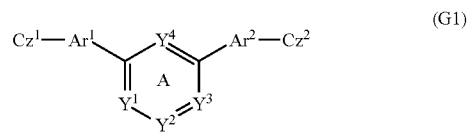

(G1)

In the general formula (G1), any one, two, or three of $Y^1$ to $Y^4$ in a ring A represent N atoms, and the rest of $Y^1$ to $Y^4$ represents CH. In the case where any two or three of the $Y^1$ to $Y^4$ are N atoms, the N atoms are not next to each other. Further, $Ar^1$ represents a substituted or unsubstituted biphenyldiyl group, $Ar^2$ represents a substituted or unsubstituted biphenyldiyl group, $Cz^1$ represents a substituted or unsubstituted heterocyclic group including a carbazole skeleton, and $Cz^2$ represents a substituted or unsubstituted heterocyclic group including a carbazole skeleton. The carbazole skeleton included in the Cz$^1$ is directly bonded to the Ar$^1$, and the carbazole skeleton included in the Cz$^2$ is directly bonded to the Ar$^2$.

Another embodiment of the present invention is a heterocyclic compound represented by the general formula (G1), in which any one or two of Y$^1$ to Y$^4$ in a ring A represent N atoms, and the rest of Y$^1$ to Y$^4$ represents CH. In the case where two of the Y$^1$ to Y$^4$ are N atoms, Y$^1$ and Y$^3$ are N atoms. Further, Ar$^1$ represents a substituted or unsubstituted biphenyldiyl group, Ar$^2$ represents a substituted or unsubstituted biphenyldiyl group, Cz$^1$ represents a substituted or unsubstituted heterocyclic group including a carbazole skeleton, and Cz$^2$ represents a substituted or unsubstituted heterocyclic group including a carbazole skeleton. The carbazole skeleton included in the Cz$^1$ is directly bonded to the Ar$^1$, and the carbazole skeleton included in the Cz$^2$ is directly bonded to the Ar$^2$.

In each of the above-described structures, in the general formula (G1), the Ar$^1$ represents a substituted or unsubstituted biphenyl-3,3'-diyl group and the Ar$^2$ represents a substituted or unsubstituted biphenyl-3,3'-diyl group.

In each of the above-described structures, in the general formula (G1), an N atom in the carbazole skeleton included in the Cz$^1$ is directly bonded to the Ar$^1$, and an N atom in the carbazole skeleton included in the Cz$^2$ is directly bonded to the Ar$^2$.

In each of the above-described structures, in the general formula (G1), the Cz$^1$ represents a substituted or unsubstituted carbazolyl group and the Cz$^2$ represents a substituted or unsubstituted carbazolyl group. Note that the carbazolyl group is preferably a N-carbazolyl group.

Another embodiment of the present invention is a heterocyclic compound represented by a general formula (G2).

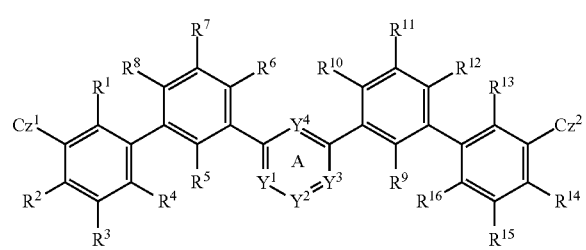

(G2)

In the general formula (G2), any one, two, or three of Y$^1$ to Y$^4$ in a ring A represent N atoms, and the rest of Y$^1$ to Y$^4$ represents CH. In the case where any two or three of the Y$^1$ to Y$^4$ are N atoms, the N atoms are not next to each other. Further, Cz$^1$ represents a substituted or unsubstituted heterocyclic group including a carbazole skeleton, and Cz$^2$ represents a substituted or unsubstituted heterocyclic group including a carbazole skeleton. The carbazole skeleton included in the Cz$^1$ and the carbazole skeleton included in the Cz$^2$ are directly bonded to different phenyl groups from each other. Each of R$^1$ to R$^{16}$ independently represents any one of hydrogen, an alkyl group having 1 to 6 carbon atoms, an alkoxy group having 1 to 6 carbon atoms, and an aryl group having 6 to 12 carbon atoms.

Another embodiment of the present invention is a heterocyclic compound represented by the general formula (G2), in which any one or two of Y$^1$ to Y$^4$ in a ring A represent N atoms, and the rest of Y$^1$ to Y$^4$ represents CH. In the case where two of the Y$^1$ to Y$^4$ are N atoms, Y$^1$ and Y$^3$ are N atoms. Further, Cz$^1$ represents a substituted or unsubstituted heterocyclic group including a carbazole skeleton, and Cz$^2$ represents a substituted or unsubstituted heterocyclic group including a carbazole skeleton. The carbazole skeleton included in the Cz$^1$ and the carbazole skeleton included in the Cz$^2$ are directly bonded to different phenyl groups from each other. Each of R$^1$ to R$^{16}$ independently represents any one of hydrogen, an alkyl group having 1 to 6 carbon atoms, an alkoxy group having 1 to 6 carbon atoms, and an aryl group having 6 to 12 carbon atoms.

Another embodiment of the present invention is a heterocyclic compound represented by a general formula (G3).

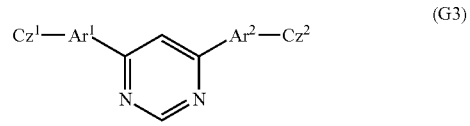

(G3)

In the general formula (G3), Ar$^1$ represents a substituted or unsubstituted biphenyldiyl group, Ar$^2$ represents a substituted or unsubstituted biphenyldiyl group, Cz$^1$ represents a substituted or unsubstituted heterocyclic group including a carbazole skeleton, and Cz$^2$ represents a substituted or unsubstituted heterocyclic group including a carbazole skeleton. The carbazole skeleton included in the Cz$^1$ is directly bonded to the Ar$^1$, and the carbazole skeleton included in the Cz$^2$ is directly bonded to the Ar$^2$.

In the above-described structure, in the general formula (G3), the Ar$^1$ represents a substituted or unsubstituted biphenyl-3,3'-diyl group and the Ar$^2$ represents a substituted or unsubstituted biphenyl-3,3'-diyl group.

Another embodiment of the present invention is a heterocyclic compound represented by a general formula (G4).

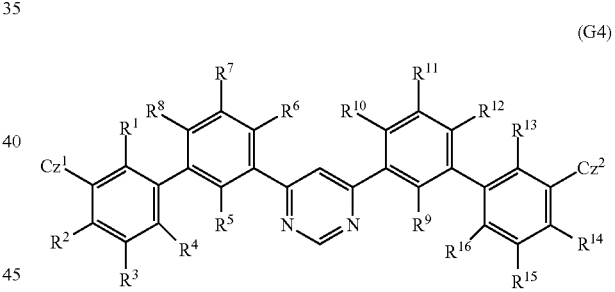

(G4)

In the general formula (G4), Cz$^1$ represents a substituted or unsubstituted heterocyclic group including a carbazole skeleton, Cz$^2$ represents a substituted or unsubstituted heterocyclic group including a carbazole skeleton, the carbazole skeleton included in the Cz$^1$ and the carbazole skeleton included in the Cz$^2$ are directly bonded to different phenyl groups from each other, and each of R$^1$ to R$^{16}$ independently represents any one of hydrogen, an alkyl group having 1 to 6 carbon atoms, an alkoxy group having 1 to 6 carbon atoms, and an aryl group having 6 to 12 carbon atoms.

Another embodiment of the present invention is a heterocyclic compound represented by a general formula (G5).

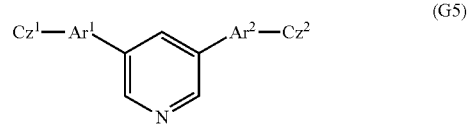

(G5)

In the general formula (G5), $Ar^1$ represents a substituted or unsubstituted biphenyldiyl group, $Ar^2$ represents a substituted or unsubstituted biphenyldiyl group, $Cz^1$ represents a substituted or unsubstituted heterocyclic group including a carbazole skeleton, $Cz^2$ represents a substituted or unsubstituted heterocyclic group including a carbazole skeleton, the carbazole skeleton included in the $Cz^1$ is directly bonded to the $Ar^1$, and the carbazole skeleton included in the $Cz^2$ is directly bonded to the $Ar^2$.

In the above-described structure, in the general formula (G5), the $Ar^1$ represents a substituted or unsubstituted biphenyl-3,3'-diyl group and the $Ar^2$ represents a substituted or unsubstituted biphenyl-3,3'-diyl group.

Another embodiment of the present invention is a heterocyclic compound represented by a general formula (G6).

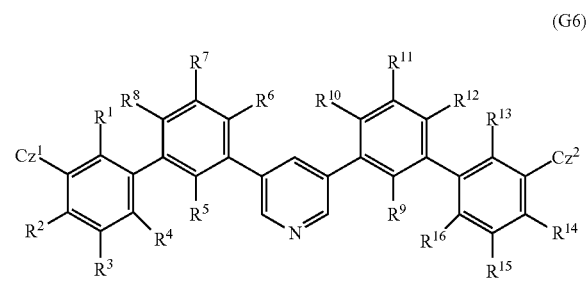

(G6)

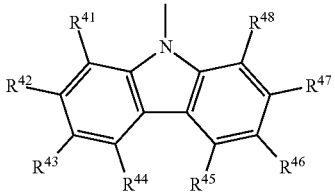

(α)

In the general formula (α), each of $R^{41}$ to $R^{48}$ independently represents any one of hydrogen, an alkyl group having 1 to 6 carbon atoms, an alkoxy group having 1 to 6 carbon atoms, a hydroxyl group, a sulfanyl group, an arylamino group having 6 to 12 carbon atoms, a vinyl group, and an aryl group having 6 to 12 carbon atoms. Further, any adjacent substituents among the $R^{41}$ to $R^{48}$ may be bonded to each other to form a ring.

In each of the above-described structures, at least one of the heterocyclic groups in the general formulae (G1) to (G6) may be an unsubstituted N-carbazolyl group.

Another embodiment of the present invention is a heterocyclic compound represented by the following structural formula (100) or structural formula (200).

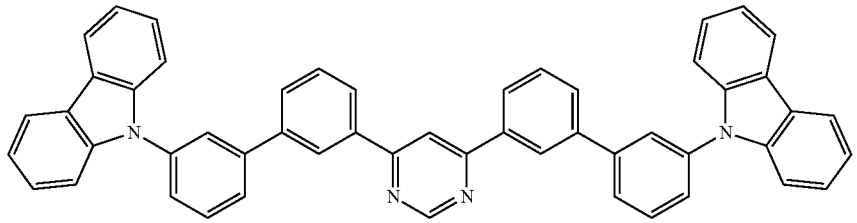

(100)

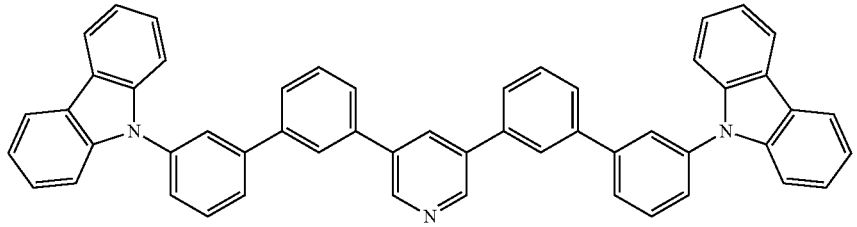

(200)

In the general formula (G6), $Cz^1$ represents a substituted or unsubstituted heterocyclic group including a carbazole skeleton, $Cz^2$ represents a substituted or unsubstituted heterocyclic group including a carbazole skeleton, the carbazole skeleton included in the $Cz^1$ and the carbazole skeleton included in the $Cz^2$ are directly bonded to different phenyl groups from each other, and each of $R^1$ to $R^{16}$ independently represents any of hydrogen, an alkyl group having 1 to 6 carbon atoms, an alkoxy group having 1 to 6 carbon atoms, and an aryl group having 6 to 12 carbon atoms.

In each of the above-described structures, at least one of the heterocyclic groups in the general formulae (G1) to (G6) is represented by a general formula (α).

Because the above-described heterocyclic compounds of embodiments of the present invention are materials having high T1 levels, they can each be used as a host material capable of being used in combination with a phosphorescent material (dopant) that emits blue light.

The heterocyclic compound of one embodiment of the present invention is a material having a high electron transport property, and accordingly can be used in an electron-transport layer or the like as well as a light-emitting layer in an EL layer of a light-emitting element. Furthermore, the heterocyclic compound of one embodiment of the present invention is a light-emitting substance, and accordingly can be used as a light-emitting substance as well as a host material which is used in combination with a light-emitting substance such as a phosphorescent material in a light-emitting layer. Accordingly, one embodiment of the present invention is a light-emitting element that uses the heterocyclic compound of one embodiment of the present invention.

The present invention includes, in its scope, not only a light-emitting device including the light-emitting element but also a lighting device including the light-emitting device. The light-emitting device in this specification refers to an image display device and a light source (e.g., a lighting device). In addition, the light-emitting device includes, in its category, all of a module in which a connector such as a flexible printed circuit (FPC) or a tape carrier package (TCP) is connected to a light-emitting device, a module in which a printed wiring board is provided on the tip of a TCP, and a module in which an integrated circuit (IC) is directly mounted on a light-emitting element by a chip on glass (COG) method.

With one embodiment of the present invention, a novel heterocyclic compound can be provided. In particular, a novel heterocyclic compound which can serve as a host material capable of being used in combination with a phosphorescent material (dopant) that emits blue light can be provided. With one embodiment of the present invention, a novel heterocyclic compound with high emission efficiency can be provided. With one embodiment of the present invention, a novel heterocyclic compound with long emission life can be provided. With one embodiment of the present invention, a novel heterocyclic compound that can be used in a light-emitting element can be provided. With one embodiment of the present invention, a novel heterocyclic compound that can be used in an EL layer of a light-emitting element can be provided. With one embodiment of the present invention, a novel light-emitting element can be provided. With one embodiment of the present invention, an efficient light-emitting element can be provided. With one embodiment of the present invention, a reliable light-emitting element can be provided. With one embodiment of the present invention, a novel light-emitting device, a novel electronic device, or a novel lighting device can be provided. Note that the descriptions of these effects do not disturb the existence of other effects. One embodiment of the present invention does not necessarily have all of these effects. Other effects will be apparent from and can be derived from the description of the specification, the drawings, the claims, and the like.

BRIEF DESCRIPTION OF THE DRAWINGS

In the accompanying drawings:

FIGS. 5A to 5D, 5D'-1, and 5D'-2 illustrate electronic devices;

DETAILED DESCRIPTION OF THE INVENTION

Figure 1A:
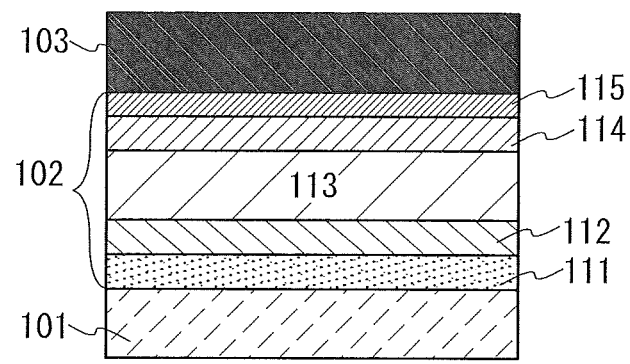
FIGS. 1A and 1B illustrate structures of light-emitting elements.

Hereinafter, embodiments of the present invention will be described with reference to the accompanying drawings. Note that the present invention is not limited to the following description, and modes and details thereof can be variously changed without departing from the spirit and scope of the present invention. Therefore, the present invention should not be construed as being limited to the description in the following embodiments.

Note that the terms "film" and "layer" can be interchanged with each other according to circumstances. For example, in some cases, the term "conductive film" can be used instead of the term "conductive layer," and the term "insulating layer" can be used instead of the term "insulating film."

Embodiment 1

In this embodiment, a heterocyclic compound which is one embodiment of the present invention is described.

In the heterocyclic compound described in this embodiment, a ring structure including nitrogen is bonded to a heterocyclic group including a carbazole skeleton via an arylene group. The heterocyclic compound described in this embodiment has a structure represented by the following general formula (G1).

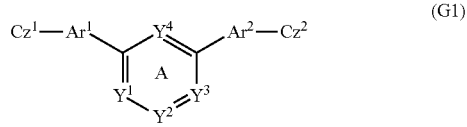

(G1)

In the general formula (G1), any one, two, or three of $Y^1$ to $Y^4$ in a ring A represent N, and the rest thereof represents CH. In the case where any two or three of $Y^1$ to $Y^4$ are N atoms, the N atoms are not next to each other. Each of $Ar^1$ and $Ar^2$ independently represents a substituted or unsubstituted biphenyldiyl group; in other words, $Ar^1$ represents a substituted or unsubstituted biphenyldiyl group and $Ar^2$ represents a substituted or unsubstituted biphenyldiyl group. Further, each of $Cz^1$ and $Cz^2$ independently represents a substituted or unsubstituted heterocyclic group including a carbazole skeleton which is directly bonded to $Ar^1$ or $Ar^2$. In other words, $Cz^1$ represents a substituted or unsubstituted heterocyclic group including a carbazole skeleton, $Cz^2$ represents a substituted or unsubstituted heterocyclic group including a carbazole skeleton, the carbazole skeleton included in $Cz^1$ is directly bonded to $Ar^1$, and the carbazole skeleton included in $Cz^2$ is directly bonded to $Ar^2$.

In the case where any one, two, or three of $Y^1$ to $Y^4$ in the ring A are N in the above-described structure represented by the general formula (G1), specific examples of the ring A are pyridine, pyrimidine, pyrazine, and triazine.

In another structure of the heterocyclic compound represented by the general formula (G1), any one or two of $Y^1$ to $Y^4$ in the ring A represent N, and the rest thereof represents CH. In the case where two of $Y^1$ to $Y^4$ are N, $Y^1$ and $Y^3$ are N. Each of $Ar^1$ and $Ar^2$ independently represents a substituted or unsubstituted biphenyldiyl group; in other words, $Ar^1$ represents a substituted or unsubstituted biphenyldiyl group and $Ar^2$ represents a substituted or unsubstituted biphenyldiyl group. Further, each of $Cz^1$ and $Cz^2$ independently represents a substituted or unsubstituted heterocyclic group including a carbazole skeleton which is directly bonded to $Ar^1$ or $Ar^2$. In other words, $Cz^1$ represents a substituted or unsubstituted heterocyclic group including a carbazole skeleton, $Cz^2$ represents a substituted or unsubstituted heterocyclic group including a carbazole skeleton, the carbazole skeleton included in $Cz^1$ is directly bonded to $Ar^1$, and the carbazole skeleton included in $Cz^2$ is directly bonded to $Ar^2$.

In the case where any one or two of $Y^1$ to $Y^4$ in the ring A are N and the rest thereof represents CH in the above-described structure represented by the general formula (G1), specific examples of the ring A are pyridine, pyrimidine, and pyrazine.

Another structure of the heterocyclic compound of one embodiment of the present invention is represented by the following general formula (G2).

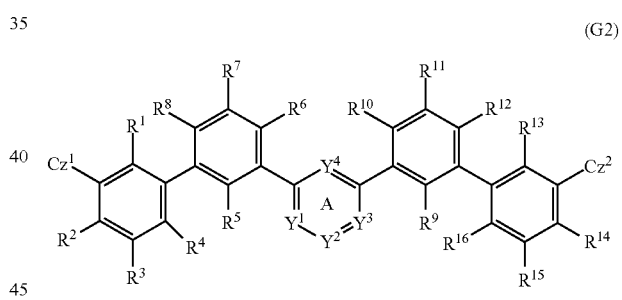

(G2)

In the general formula (G2), any one, two, or three of $Y^1$ to $Y^4$ in a ring A represent N, and the rest thereof represents CH. In the case where any two or three of $Y^1$ to $Y^4$ are N atoms, the N atoms are not next to each other. Further, each of $Cz^1$ and $Cz^2$ independently represents a substituted or unsubstituted heterocyclic group including a carbazole skeleton which is directly bonded to a phenyl group. In other words, $Cz^1$ represents a substituted or unsubstituted heterocyclic group including a carbazole skeleton, $Cz^2$ represents a substituted or unsubstituted heterocyclic group including a carbazole skeleton, the carbazole skeleton included in $Cz^1$ and the carbazole skeleton included in $Cz^2$ are directly bonded to different phenyl groups from each other. Each of $R^1$ to $R^{16}$ independently represents any one of hydrogen, an alkyl group having 1 to 6 carbon atoms, an alkoxy group having 1 to 6 carbon atoms, and an aryl group having 6 to 12 carbon atoms.

In the case where any one, two, or three of $Y^1$ to $Y^4$ in the ring A are N in the above-described structure represented by the general formula (G2), specific examples of the ring A are pyridine, pyrimidine, pyrazine, and triazine.

In another structure of the heterocyclic compound represented by the general formula (G2), any one or two of $Y^1$ to $Y^4$ in the ring A represent N, and the rest thereof represents CH. In the case where two of $Y^1$ to $Y^4$ are N, $Y^1$ and $Y^3$ are N. Further, each of $Cz^1$ and $Cz^2$ independently represents a substituted or unsubstituted heterocyclic group including a carbazole skeleton which is directly bonded to a phenyl group. In other words, $Cz^1$ represents a substituted or unsubstituted heterocyclic group including a carbazole skeleton, $Cz^2$ represents a substituted or unsubstituted heterocyclic group including a carbazole skeleton, the carbazole skeleton included in $Cz^1$ and the carbazole skeleton included in $Cz^2$ are directly bonded to different phenyl groups from each other. Each of $R^1$ to $R^{16}$ independently represents any one of hydrogen, an alkyl group having 1 to 6 carbon atoms, an alkoxy group having 1 to 6 carbon atoms, and an aryl group having 6 to 12 carbon atoms.

In the case where any one or two of $Y^1$ to $Y^4$ in the ring A are N and the rest thereof represents CH in the above-described structure represented by the general formula (G2), specific examples of the ring A are pyridine, pyrimidine, and pyrazine.

Another structure of the heterocyclic compound of one embodiment of the present invention is represented by the following general formula (G3).

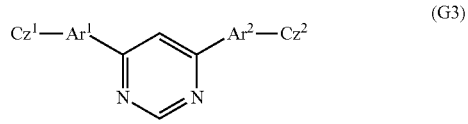
(G3)

In the general formula (G3), each of $Ar^1$ and $Ar^2$ independently represents a substituted or unsubstituted biphenyldiyl group, and each of $Cz^1$ and $Cz^2$ independently represents a substituted or unsubstituted heterocyclic group including a carbazole skeleton which is directly bonded to $Ar^1$ or $Ar^2$. In other words, $Ar^1$ represents a substituted or unsubstituted biphenyldiyl group, $Ar^2$ represents a substituted or unsubstituted biphenyldiyl group, $Cz^1$ represents a substituted or unsubstituted heterocyclic group including a carbazole skeleton, $Cz^2$ represents a substituted or unsubstituted heterocyclic group including a carbazole skeleton, the carbazole skeleton included in $Cz^1$ is directly bonded to $Ar^1$, and the carbazole skeleton included in $Cz^2$ is directly bonded to $Ar^2$.

Another structure of the heterocyclic compound of one embodiment of the present invention is represented by the following general formula (G4).

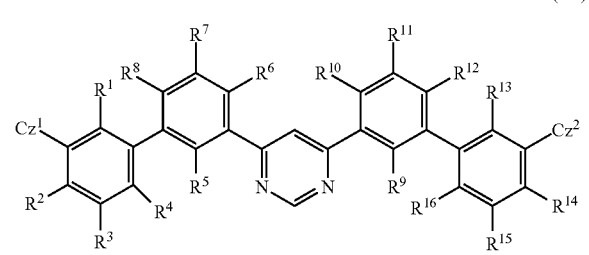
(G4)

In the general formula (G4), each of $Cz^1$ and $Cz^2$ independently represents a substituted or unsubstituted heterocyclic group including a carbazole skeleton which is directly bonded to a phenyl group. In other words, $Cz^1$ represents a substituted or unsubstituted heterocyclic group including a carbazole skeleton, $Cz^2$ represents a substituted or unsubstituted heterocyclic group including a carbazole skeleton, the carbazole skeleton included in $Cz^1$ and the carbazole skeleton included in $Cz^2$ are directly bonded to different phenyl groups from each other. Each of $R^1$ to $R^{16}$ independently represents any one of hydrogen, an alkyl group having 1 to 6 carbon atoms, an alkoxy group having 1 to 6 carbon atoms, and an aryl group having 6 to 12 carbon atoms.

Another structure of the heterocyclic compound of one embodiment of the present invention is represented by the following general formula (G5).

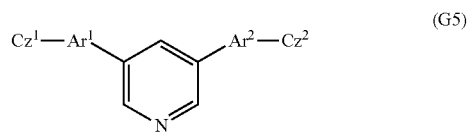
(G5)

In the general formula (G5), each of $Ar^1$ and $Ar^2$ independently represents a substituted or unsubstituted biphenyldiyl group; in other words, $Ar^1$ represents a substituted or unsubstituted biphenyldiyl group and $Ar^2$ represents a substituted or unsubstituted biphenyldiyl group. Further, each of $Cz^1$ and $Cz^2$ independently represents a substituted or unsubstituted heterocyclic group including a carbazole skeleton which is directly bonded to $Ar^1$ or $Ar^2$. In other words, $Cz^1$ represents a substituted or unsubstituted heterocyclic group including a carbazole skeleton, $Cz^2$ represents a substituted or unsubstituted heterocyclic group including a carbazole skeleton, the carbazole skeleton included in $Cz^1$ is directly bonded to $Ar^1$, and the carbazole skeleton included in $Cz^2$ is directly bonded to $Ar^2$.

Another structure of the heterocyclic compound of one embodiment of the present invention is represented by the following general formula (G6).

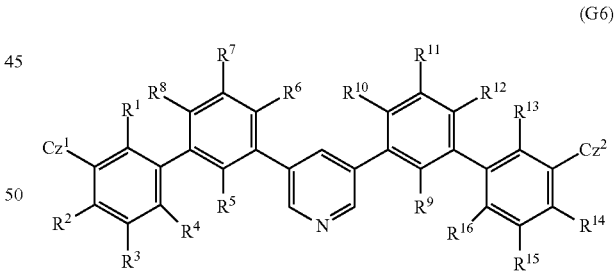
(G6)

In the general formula (G6), each of $Cz^1$ and $Cz^2$ independently represents a substituted or unsubstituted heterocyclic group including a carbazole skeleton which is directly bonded to a phenyl group. In other words, $Cz^1$ represents a substituted or unsubstituted heterocyclic group including a carbazole skeleton, $Cz^2$ represents a substituted or unsubstituted heterocyclic group including a carbazole skeleton, the carbazole skeleton included in $Cz^1$ and the carbazole skeleton included in $Cz^2$ are directly bonded to different phenyl groups from each other. Each of $R^1$ to $R^{16}$ independently represents any one of hydrogen, an alkyl group having 1 to 6 carbon atoms, an alkoxy group having 1 to 6 carbon atoms, and an aryl group having 6 to 12 carbon atoms.

Specific examples of the biphenyldiyl group in each of the above-described structures represented by the general formulae (G1), (G3), and (G5) are a biphenyl-3,3'-diyl group, a biphenyl-4,4'-diyl group, and a biphenyl-3,4'-diyl group.

In each of the above-described structures of the general formulae (G1) to (G6), the substituted or unsubstituted heterocyclic group including a carbazole skeleton preferably has a structure represented by the following general formula (α).

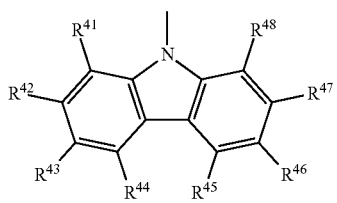

(α)

In the general formula (α), each of $R^{41}$ to $R^{48}$ independently represents any one of hydrogen, an alkyl group having 1 to 6 carbon atoms, an alkoxy group having 1 to 6 carbon atoms, a hydroxyl group, a sulfanyl group, an arylamino group having 6 to 12 carbon atoms, a vinyl group, and an aryl group having 6 to 12 carbon atoms. Any adjacent substituents among $R^{41}$ to $R^{48}$ may be bonded to each other to form a ring.

In each of the above-described structures of the general formulae (G1) to (G6), a specific example of the substituted or unsubstituted heterocyclic group including a carbazole skeleton is a substituted or unsubstituted carbazolyl group. Specific examples of the carbazolyl group are a N-carbazolyl group, a 9-phenyl-9H-carbazol-3-yl group, and a 9-phenyl-9H-carbazol-2-yl group, among which a N-carbazolyl group is especially preferable.

In the case where the heterocyclic group has a substituent in each of the above-described structures represented by the general formulae (G1) to (G6), examples of the substituent are hydrogen, an alkyl group having 1 to 6 carbon atoms, an alkoxy group having 1 to 6 carbon atoms, a hydroxyl group, a sulfanyl group, an arylamino group having 6 to 12 carbon atoms, a vinyl group, and an aryl group having 6 to 12 carbon atoms. Any adjacent substituents among these substituents may be bonded to each other to form a ring.

Examples of $R^1$ to $R^{16}$ in each of the above-described structures represented by the general formulae (G2), (G4), and (G6) are hydrogen, an alkyl group having 1 to 6 carbon atoms, an alkoxy group having 1 to 6 carbon atoms, a hydroxyl group, a sulfanyl group, an arylamino group having 6 to 12 carbon atoms, a vinyl group, and an aryl group having 6 to 12 carbon atoms.

Specific examples of the alkyl group having 1 to 6 carbon atoms are a methyl group, an ethyl group, a propyl group, an isopropyl group, a butyl group, a sec-butyl group, an isobutyl group, a tert-butyl group, a pentyl group, an isopentyl group, a sec-pentyl group, a tert-pentyl group, a neopentyl group, a 1-methylpentyl group, a hexyl group, and an isohexyl group.

Specific examples of the alkoxy group having 1 to 6 carbon atoms are a methoxy group, an ethoxy group, a propoxy group, an isopropoxy group, a butoxy group, a sec-butoxy group, an isobutoxy group, and a tert-butoxy group.

Specific examples of the arylamino group having 6 to 12 carbon atoms are a phenylamino group, an o-tolylamino group, an m-tolylamino group, a p-tolylamino group, a 1-naphthylamino group, a 2-naphthylamino group, a biphenyl-2-ylamino group, a biphenyl-3-ylamino group, and a biphenyl-4-ylamino group.

Specific examples of the aryl group having 6 to 12 carbon atoms are a phenyl group, an o-tolyl group, an m-tolyl group, a p-tolyl group, a 1-naphthyl group, a 2-naphthyl group, a biphenyl-2-yl group, a biphenyl-3-yl group, and a biphenyl-4-yl group. For example, in the case where the aryl group is a 2-fluorenyl group having two phenyl groups at the 9-position as a substituent, the phenyl groups may be bonded to each other to become a spiro-9,9'-bifluoren-2-yl group. More specifically, a phenyl group, a tolyl group, a xylyl group, a biphenyl group, an indenyl group, a naphthyl group, a fluorenyl group, and the like can be given.

Examples of $R^{41}$ to $R^{48}$ in the general formula (α) in each of the above-described structures are hydrogen, an alkyl group having 1 to 6 carbon atoms, an alkoxy group having 1 to 6 carbon atoms, a hydroxyl group, a sulfanyl group, an arylamino group having 6 to 12 carbon atoms, a vinyl group, and an aryl group having 6 to 12 carbon atoms. Any adjacent groups among these groups may be bonded to each other to form a ring.

Next, specific structural formulae (100) to (110), (200) to (205), and (300) to (301) of the above-described heterocyclic compounds, each of which is one embodiment of the present invention, are shown below. Note that the present invention is not limited thereto.

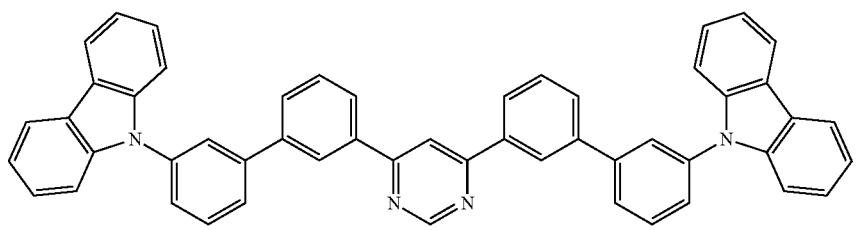

(100)

-continued
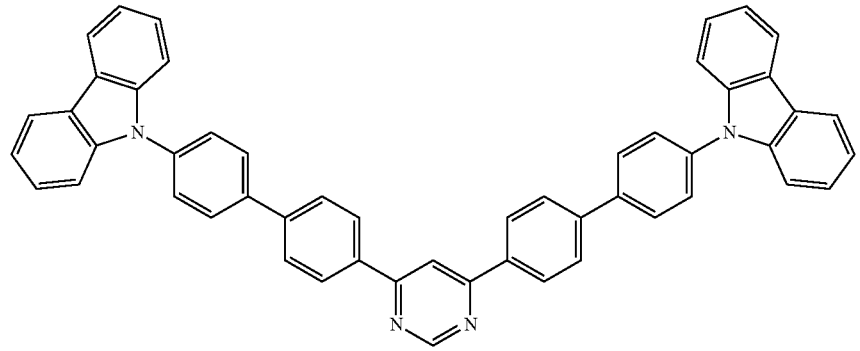
(101)
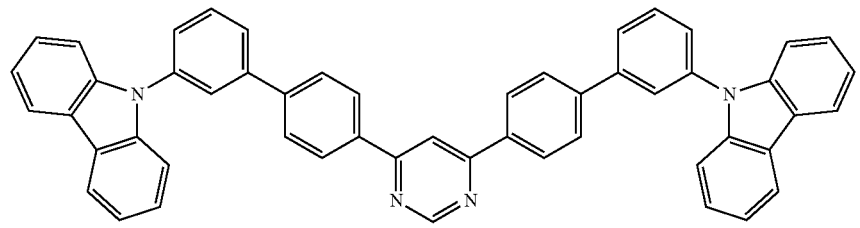
(102)
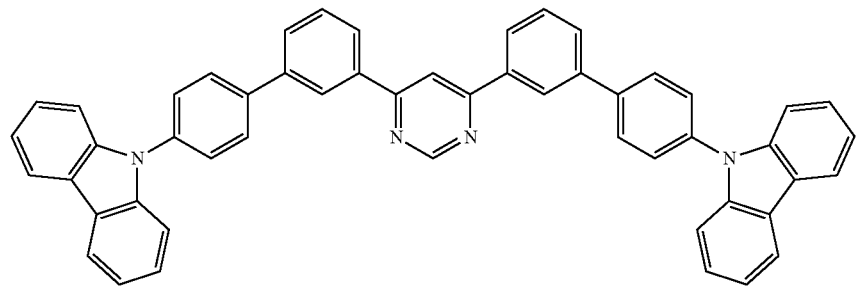
(103)
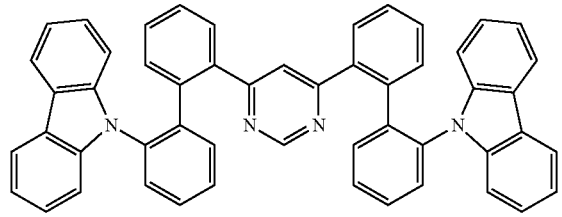
(104)
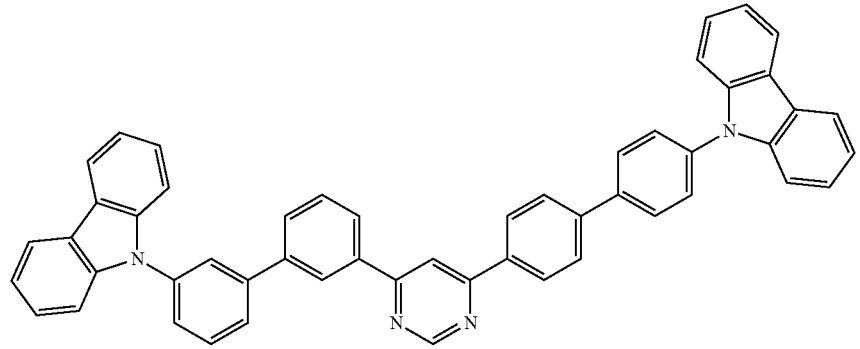
(105)

-continued
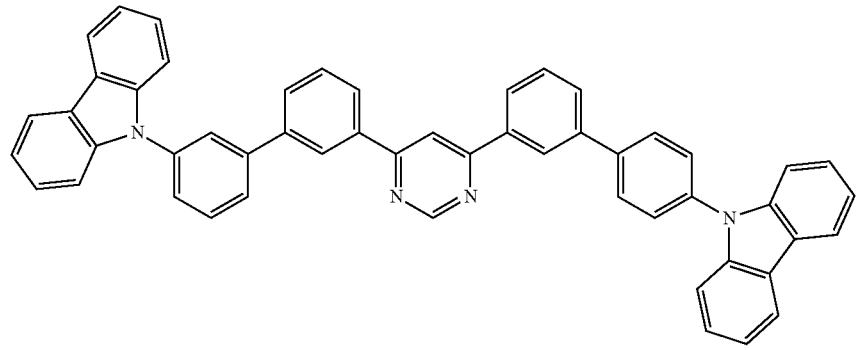
(106)
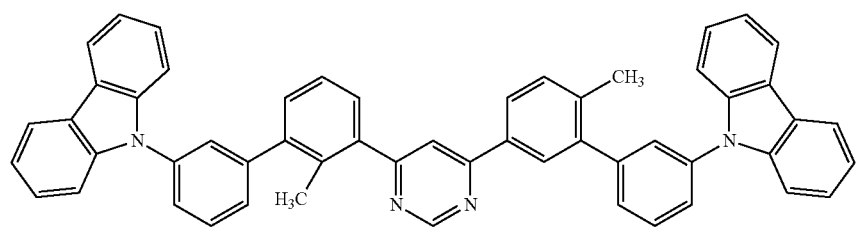
(107)
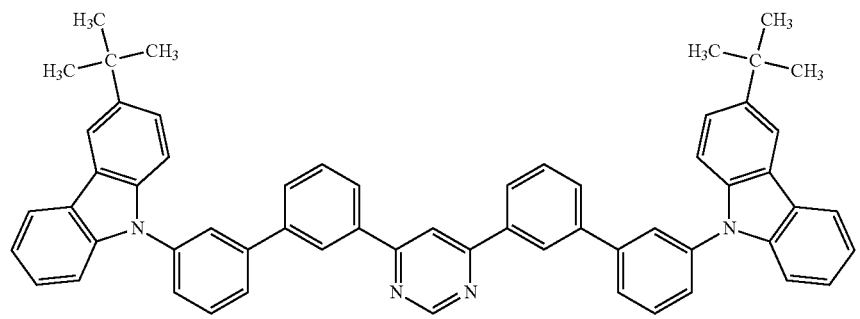
(108)
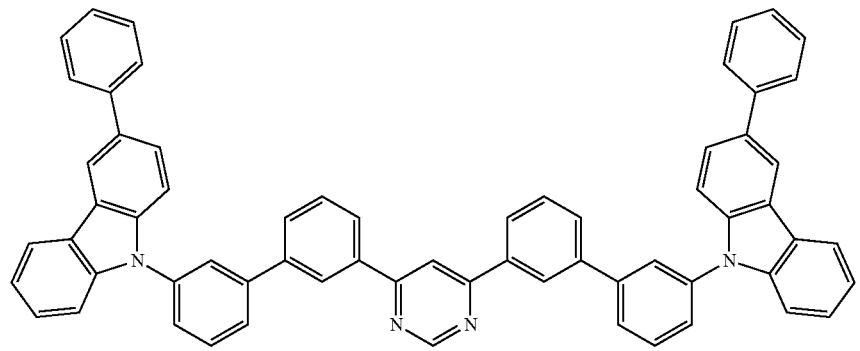
(109)
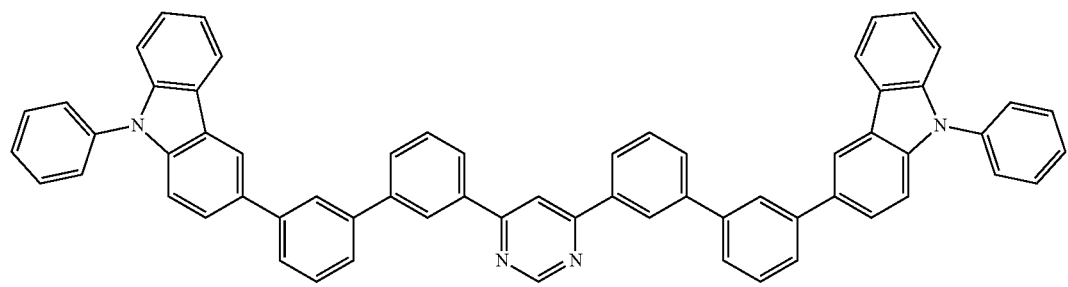
(110)

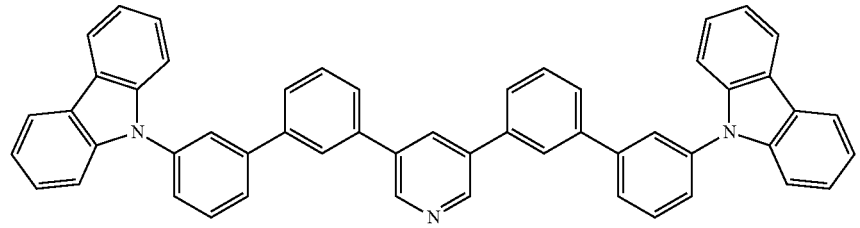
(200)
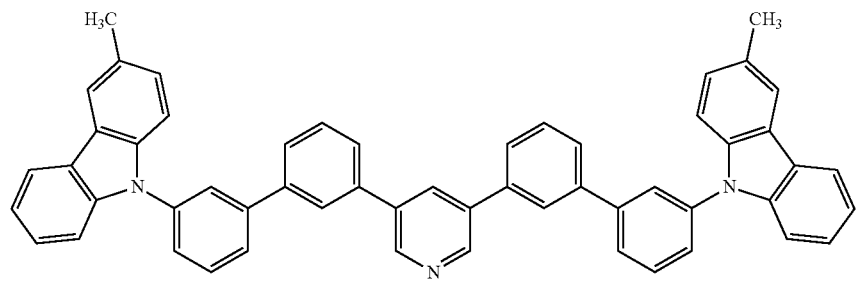
(201)
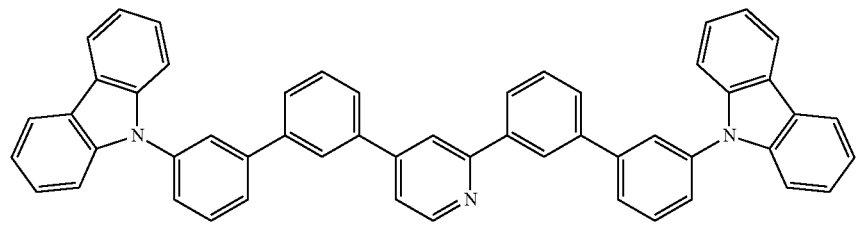
(202)
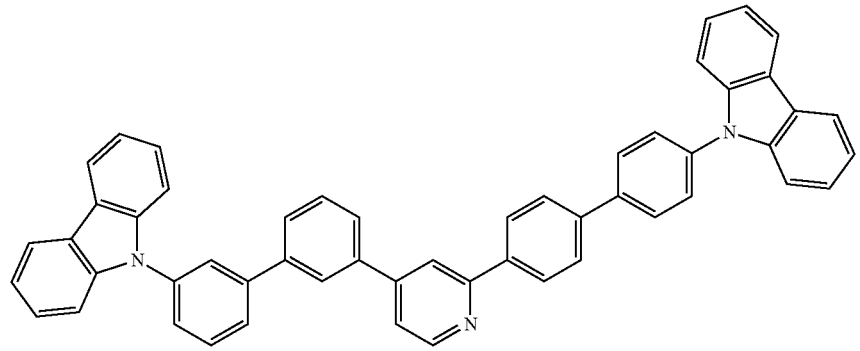
(203)
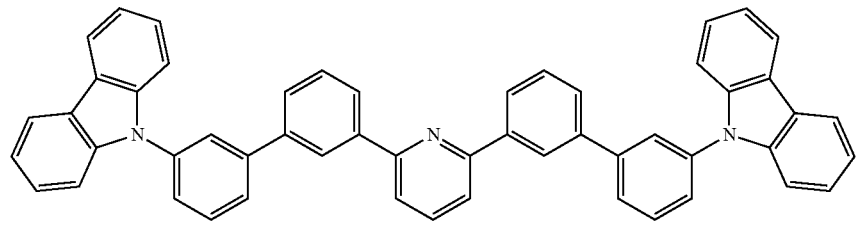
(204)
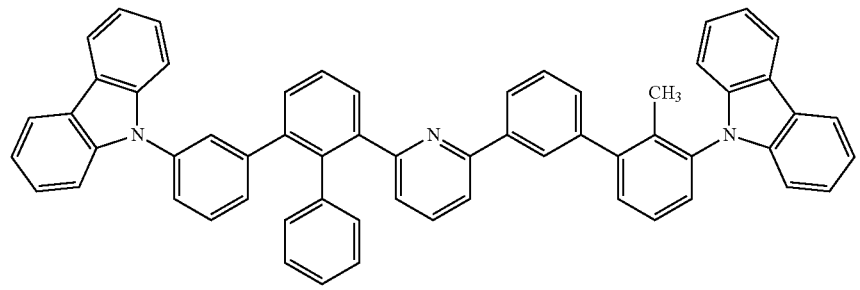
(205)

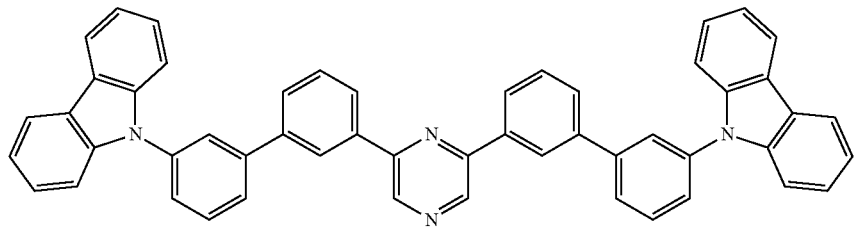

(300)

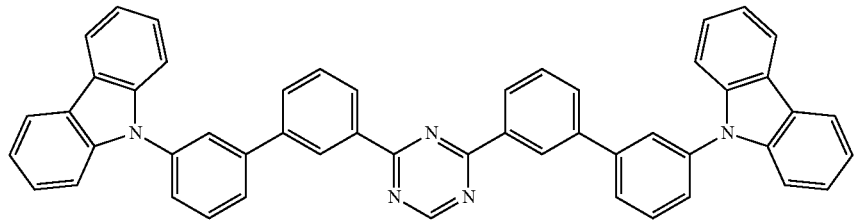

(301)

Next, an example of a method of synthesizing the heterocyclic compound which is one embodiment of the present invention represented by the following general formula (G1) is described.

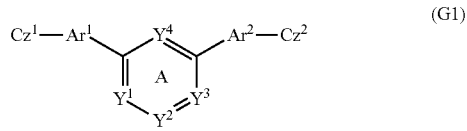

(G1)

Note that in the general formula (G1), any one, two, or three of $Y^1$ to $Y^4$ in a ring A represent N, and the rest thereof represents CH. In the case where any two or three of $Y^1$ to $Y^4$ are N atoms, the N atoms are not next to each other. Further, $Ar^1$ represents a substituted or unsubstituted biphenyldiyl group, $Ar^2$ represents a substituted or unsubstituted biphenyldiyl group, $Cz^1$ represents a substituted or unsubstituted carbazolyl group, and $Cz^2$ represents a substituted or unsubstituted carbazolyl group.

A synthesis scheme (A) of the heterocyclic compound represented by the general formula (G1) is shown below. In the synthesis scheme (A), the heterocyclic compound represented by the general formula (G1) can be obtained by coupling a compound 1 which is a cyclic compound, a compound 2 including a carbazole skeleton, and a compound 3 including a carbazole skeleton by a Suzuki-Miyaura reaction.

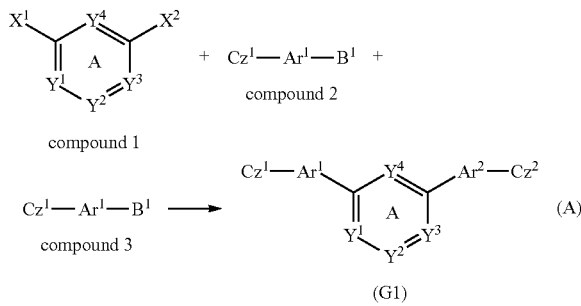

Note that in the synthesis scheme (A), any one, two, or three of $Y^1$ to $Y^4$ in a ring A represent N, and the rest thereof represents CH. In the case where any two or three of $Y^1$ to $Y^4$ are N atoms, the N atoms are not next to each other. Further, $Ar^1$ represents a substituted or unsubstituted biphenyldiyl group, $Ar^2$ represents a substituted or unsubstituted biphenyldiyl group, $Cz^1$ represents a substituted or unsubstituted carbazolyl group, and $Cz^2$ represents a substituted or unsubstituted carbazolyl group. Further, each of $B^1$ and $B^2$ independently represents either a boronic acid or boronic ester. In addition, each of $X^1$ and $X^2$ represents either halogen or a triflate group.

In the above synthesis scheme (A), when the compound 2 and the compound 3 are different compounds, the compound 1 and the compound 2 are coupled and then the resulting substance and the compound 3 are coupled, so that the target compound of the synthesis can be obtained with high purity in a high yield.

Examples of a palladium catalyst that can be used in the synthesis scheme (A) include, but are not limited to, palladium(II) acetate, tetrakis(triphenylphosphine)palladium(0), and bis(triphenylphosphine)palladium(II) dichloride. Examples of a ligand of the palladium catalyst include, but are not limited to, tri(ortho-tolyl)phosphine, triphenylphosphine, and tricyclohexylphosphine.

Examples of a base which can be used in the synthesis scheme (A) include, but are not limited to, an organic base such as sodium tert-butoxide and inorganic bases such as potassium carbonate and sodium carbonate. Examples of a solvent that can be used in the synthesis scheme (A) include, but are not limited to, a mixed solvent of toluene and water; a mixed solvent of toluene, alcohol such as ethanol, and water; a mixed solvent of xylene and water; a mixed solvent of xylene, alcohol such as ethanol, and water; a mixed solvent of benzene and water; a mixed solvent of benzene, alcohol such as ethanol, and water; a mixed solvent of water and an ether such as ethylene glycol dimethyl ether; and a mixed solvent of an ether such as ethylene glycol dimethyl ether and alcohol such as t-butyl alcohol. In particular, the mixed solvent of toluene and water, the mixed solvent of toluene, ethanol, and water, the mixed solvent of water and an ether such as ethylene glycol dimethyl ether, and the mixed solvent of an ether such as ethylene glycol dimethyl ether and alcohol such as t-butyl alcohol are preferable.

In the above synthesis scheme (A), the compound 2 and the compound 3 are organic boron compounds and hence the Suzuki-Miyaura coupling reaction is employed to cause a reaction. Alternatively, in the case where the compound 2 and the compound 3 are organoaluminum compounds, organozirconium compounds, organozinc compounds, organotin compounds, or the like, a cross coupling reaction can be employed to give the target compound of the synthesis. However, the present invention is not limited thereto.

Alternatively, in the synthesis scheme (A), a reaction may be caused using a diboronic acid compound as the compound 1 (where each of $X^1$ and $X^2$ independently represents a boronic acid or boronic ester) and halogen compounds or triflate compounds as the compound 2 and the compound 3 (where each of $B^1$ and $B^2$ independently represents a halogen or a triflate group).

The example of a method of synthesizing a heterocyclic compound which is one embodiment of the present invention has been described so far; however, the present invention is not limited thereto and the heterocyclic compound may be synthesized using any other synthesis method.

Each of the above-described heterocyclic compounds, which is one embodiment of the present invention, can be used alone or in combination with a light-emitting substance (guest), another organic compound, or the like in a light-emitting element.

By using a heterocyclic compound of one embodiment of the present invention, a light-emitting element with high emission efficiency or a light-emitting element with long emission life can be provided. Furthermore, an efficient light-emitting device, an efficient electronic device, or an efficient lighting device can be provided. Moreover, a light-emitting element, a light-emitting device, an electronic device, or a lighting device with low power consumption can be obtained.

Note that embodiments of the present invention have been described in Embodiment 1. Other embodiments of the present invention are described in Embodiments 2 to 8. However, embodiments of the present invention are not limited to these embodiments. That is, since various embodiments of the present invention are disclosed in Embodiments 1 to 8, one embodiment of the present invention is not limited to a specific embodiment. Although an example in which one embodiment of the present invention is used in a light-emitting element is described, one embodiment of the present invention is not limited thereto. Depending on circumstances or conditions, one embodiment of the present invention may be used in objects other than a light-emitting element. Furthermore, depending on circumstances or conditions, one embodiment of the present invention need not be used in a light-emitting element. Although an example of using a heterocyclic compound has been described as one embodiment of the present invention, one embodiment of the present invention is not limited thereto.

The structure described in this embodiment can be used in appropriate combination with any of the structures described in the other embodiments.

Embodiment 2

In this embodiment, a light-emitting element which is one embodiment of the present invention will be described with reference to FIGS. 1A and 1B.

In the light-emitting element described in this embodiment, an EL layer 102 including a light-emitting layer 113 is interposed between a pair of electrodes (a first electrode (anode) 101 and a second electrode (cathode) 103), and the EL layer 102 includes a hole-injection layer 111, a hole-transport layer 112, an electron-transport layer 114, an electron-injection layer 115, and the like in addition to the light-emitting layer 113.

When a voltage is applied to the light-emitting element, holes injected from the first electrode 101 side and electrons injected from the second electrode 103 side recombine in the light-emitting layer 113; with energy generated by the recombination, a light-emitting substance such as the organometallic complex that is contained in the light-emitting layer 113 emits light.

The hole-injection layer 111 in the EL layer 102 can inject holes into the hole-transport layer 112 or the light-emitting layer 113 and can be formed of, for example, a substance having a high hole-transport property and a substance having an acceptor property, in which case electrons are extracted from the substance having a high hole-transport property by the substance having an acceptor property to generate holes. Thus, holes are injected from the hole-injection layer 111 into the light-emitting layer 113 through the hole-transport layer 112. For the hole-injection layer 111, a substance having a high hole-injection property can also be used. For example, molybdenum oxide, vanadium oxide, ruthenium oxide, tungsten oxide, manganese oxide, or the like can be used. Alternatively, the hole-injection layer 111 can be formed using a phthalocyanine-based compound such as phthalocyanine (abbreviation: $H_2Pc$) and copper phthalocyanine (CuPc), an aromatic amine compound such as 4,4'-bis[N-(4-diphenylaminophenyl)-N-phenylamino]biphenyl (abbreviation: DPAB) and N,N'-bis{4-[bis(3-methylphenyl)amino]phenyl}-N,N'-diphenyl-(1,1'-biphenyl)-4,4'-diamine (abbreviation: DNTPD), or a high molecular compound such as poly(3,4-ethylenedioxythiophene)/poly (styrenesulfonic acid) (PEDOT/PSS).

A specific example in which the light-emitting element described in this embodiment is fabricated is described below.

For the first electrode (anode) 101 and the second electrode (cathode) 103, a metal, an alloy, an electrically conductive compound, a mixture thereof, and the like can be used. Specific examples are indium oxide-tin oxide (indium tin oxide), indium oxide-tin oxide containing silicon or silicon oxide, indium oxide-zinc oxide (indium zinc oxide), indium oxide containing tungsten oxide and zinc oxide, gold (Au), platinum (Pt), nickel (Ni), tungsten (W), chromium (Cr), molybdenum (Mo), iron (Fe), cobalt (Co), copper (Cu), palladium (Pd), and titanium (Ti). In addition, an element belonging to Group 1 or Group 2 of the periodic table, for example, an alkali metal such as lithium (Li) or cesium (Cs), an alkaline earth metal such as calcium (Ca) or strontium (Sr), magnesium (Mg), an alloy containing such an element (MgAg or AlLi), a rare earth metal such as europium (Eu) or ytterbium (Yb), an alloy containing such an element, graphene, and the like can be used. The first electrode (anode) 101 and the second electrode (cathode) 103 can be formed by, for example, a sputtering method or an evaporation method (including a vacuum evaporation method).

As the substance having a high hole-transport property which is used for the hole-injection layer 111 and the hole-transport layer 112, any of a variety of organic compounds such as aromatic amine compounds, carbazole derivatives, aromatic hydrocarbons, and high molecular compounds (e.g., oligomers, dendrimers, or polymers) can be used. Specifically, a substance having a hole mobility of $10^{-6}$ $cm^2/Vs$ or more is preferably used. The layer formed using the substance having a high hole-transport property is not limited to a single layer and may be formed by stacking two or more layers. Organic compounds that can be used as the substance having a hole-transport property are specifically given below.

Examples of the aromatic amine compounds are N,N'-di(p-tolyl)-N,N'-diphenyl-p-phenylenediamine (abbreviation: DTDPPA), 4,4'-bis[N-(4-diphenylaminophenyl)-N-phenylamino]biphenyl (abbreviation: DPAB), DNTPD, 1,3,5-tris[N-(4-diphenylaminophenyl)-N-phenylamino]benzene (abbreviation: DPA3B), 4,4'-bis[N-(1-naphthyl)-N-phenylamino]biphenyl (abbreviation: NPB or α-NPD), N,N'-bis(3-methylphenyl)-N,N'-diphenyl-[1,1'-biphenyl]-4,4'-diamine (abbreviation: TPD), 4,4',4"-tris(carbazol-9-yl)triphenylamine (abbreviation: TCTA), 4,4',4"-tris(N,N-diphenylamino)triphenylamine (abbreviation: TDATA), 4,4',4"-tris[N-(3-methylphenyl)-N-phenylamino]triphenylamine (abbreviation: MTDATA), and 4,4'-bis[N-(spiro-9,9'-bifluoren-2-yl)-N-phenylamino]biphenyl (abbreviation: BSPB), and the like.

Specific examples of carbazole derivatives are 3-[N-(9-phenylcarbazol-3-yl)-N-phenylamino]-9-phenylcarbazole (abbreviation: PCzPCA1), 3,6-bis[N-(9-phenylcarbazol-3-yl)-N-phenylamino]-9-phenylcarbazole (abbreviation: PCzPCA2), 3-[N-(1-naphthyl)-N-(9-phenylcarbazol-3-yl)amino]-9-phenylcarbazole (abbreviation: PCzPCN1), and the like. Other examples are 4,4'-di(N-carbazolyl)biphenyl (abbreviation: CBP), 1,3,5-tris[4-(N-carbazolyl)phenyl]benzene (abbreviation: TCPB), 9-[4-(10-phenyl-9-anthracenyl)phenyl]-9H-carbazole (abbreviation: CzPA), 1,4-bis[4-(N-carbazolyl)phenyl]-2,3,5,6-tetraphenylbenzene, and the like.

Examples of aromatic hydrocarbons are 2-tert-butyl-9,10-di(2-naphthyl)anthracene (abbreviation: t-BuDNA), 2-tert-butyl-9,10-di(1-naphthyl)anthracene, 9,10-bis(3,5-diphenylphenyl)anthracene (abbreviation: DPPA), 2-tert-butyl-9,10-bis(4-phenylphenyl)anthracene (abbreviation: t-BuDBA), 9,10-di(2-naphthyl)anthracene (abbreviation: DNA), 9,10-diphenylanthracene (abbreviation: DPAnth), 2-tert-butylanthracene (abbreviation: t-BuAnth), 9,10-bis(4-methyl-1-naphthyl)anthracene (abbreviation: DMNA), 2-tert-butyl-9,10-bis[2-(1-naphthyl)phenyl]anthracene, 9,10-bis[2-(1-naphthyl)phenyl]anthracene, 2,3,6,7-tetramethyl-9,10-di(1-naphthyl)anthracene, 2,3,6,7-tetramethyl-9,10-di(2-naphthyl)anthracene, 9,9'-bianthryl, 10,10'-diphenyl-9,9'-bianthryl, 10,10'-bis(2-phenylphenyl)-9,9'-bianthryl, 10,10'-bis[(2,3,4,5,6-pentaphenyl)phenyl]-9,9'-bianthryl, anthracene, tetracene, rubrene, perylene, 2,5,8,11-tetra(tert-butyl)perylene, and the like. Besides, pentacene, coronene, or the like can also be used. The aromatic hydrocarbon which has a hole mobility of $1 \times 10^{-6}$ cm$^2$/Vs or more and which has 14 to 42 carbon atoms is particularly preferable. The aromatic hydrocarbons may have a vinyl skeleton. Examples of the aromatic hydrocarbon having a vinyl group are 4,4'-bis(2,2-diphenylvinyl)biphenyl (abbreviation: DPVBi) and 9,10-bis[4-(2,2-diphenylvinyl)phenyl]anthracene (abbreviation: DPVPA).

A high molecular compound such as poly(N-vinylcarbazole) (abbreviation: PVK), poly(4-vinyltriphenylamine) (abbreviation: PVTPA), poly[N-(4-{N'-[4-(4-diphenylamino)phenyl]phenyl-N'-phenylamino}phenyl)methacrylamide] (abbreviation: PTPDMA), or poly[N,N'-bis(4-butylphenyl)-N,N'-bis(phenyl)benzidine] (abbreviation: Poly-TPD) can also be used.

Examples of the substance having an acceptor property which is used for the hole-injection layer 111 and the hole-transport layer 112 are compounds having an electron-withdrawing group (a halogen group or a cyano group) such as 7,7,8,8-tetracyano-2,3,5,6-tetrafluoroquinodimethane (abbreviation: F$_4$-TCNQ), chloranil, and 2,3,6,7,10,11-hexacyano-1,4,5,8,9,12-hexaazatriphenylene (HAT-CN). In particular, a compound in which electron-withdrawing groups are bonded to a condensed aromatic ring having a plurality of heteroatoms, like HAT-CN, is thermally stable and preferable. Oxides of metals belonging to Groups 4 to 8 of the periodic table can be given. Specifically, vanadium oxide, niobium oxide, tantalum oxide, chromium oxide, molybdenum oxide, tungsten oxide, manganese oxide, and rhenium oxide are preferable because of their high electron-accepting properties. Among these, molybdenum oxide is especially preferable because it is stable in the air, has a low hygroscopic property, and is easy to handle.

The light-emitting layer 113 contains a light-emitting substance, which may be a fluorescent substance or a phosphorescent substance. As the phosphorescent substance, an organometallic complex is used specifically. In the case where an organometallic complex (guest material) is used in the light-emitting layer 113, it is preferable that a substance having higher triplet excitation energy than this organometallic complex be contained as a host material. Alternatively, the light-emitting layer 113 may contain, in addition to the light-emitting substance, two kinds of organic compounds that can form an excited complex (also called an exciplex) at the time of recombination of carriers (electrons and holes) in the light-emitting layer 113 (the two kinds of organic compounds may be any of host materials as described above). In order to form an exciplex efficiently, it is particularly preferable to combine a compound which easily accepts electrons (a material having an electron-transport property) and a compound which easily accepts holes (a material having a hole-transport property). In the case where the combination of a material having an electron-transport property and a material having a hole-transport property which form an exciplex is used as a host material as described above, the carrier balance between holes and electrons in the light-emitting layer can be easily optimized by adjustment of the mixture ratio of the material having an electron-transport property and the material having a hole-transport property. The optimization of the carrier balance between holes and electrons in the light-emitting layer can prevent a region in which electrons and holes are recombined from existing on one side in the light-emitting layer. By preventing the region in which electrons and holes are recombined from existing on one side, the reliability of the light-emitting element can be improved.

As the compound that is preferably used to form the above exciplex and easily accepts electrons (material having an electron-transport property), a π-electron deficient heteroaromatic compound such as a nitrogen-containing heteroaromatic compound, a metal complex, or the like can be used. Specific examples include metal complexes such as bis(10-hydroxybenzo[h]quinolinato)beryllium(II) (abbreviation: BeBq$_2$), bis(2-methyl-8-quinolinolato)(4-phenylphenolato)aluminum(III) (abbreviation: BAlq), bis(8-quinolinolato)zinc(II) (abbreviation: Znq), bis[2-(2-benzoxazolyl)phenolato]zinc(II) (abbreviation: ZnPBO), and bis[2-(2-benzothiazolyl)phenolato]zinc(II) (abbreviation: ZnBTZ); heterocyclic compounds having polyazole skeletons, such as 2-(4-biphenylyl)-5-(4-tert-butylphenyl)-1,3,4-oxadiazole (abbreviation: PBD), 3-(4-biphenylyl)-4-phenyl-5-(4-tert-butylphenyl)-1,2,4-triazole (abbreviation: TAZ), 1,3-bis[5-(p-tert-butylphenyl)-1,3,4-oxadiazol-2-yl]benzene (abbreviation: OXD-7), 9-[4-(5-phenyl-1,3,4-oxadiazol-2-yl)phenyl]-9H-carbazole (abbreviation: CO11), 2,2',2"-(1,3,5-benzenetriyl)tris(1-phenyl-1H-benzimidazole) (abbreviation: TPBI), and 2-[3-(dibenzothiophen-4-yl)phenyl]-1-phenyl-1H-benzimidazole (abbreviation: mDBT-BIm-II); heterocyclic compounds having diazine skeletons, such as 2-[3-(dibenzothiophen-4-yl)phenyl]dibenzo[f,h]quinoxaline (abbreviation: 2mDBTPDBq-II), 2-[3'-(dibenzothiophen-4-yl)biphenyl-3-yl]dibenzo[f,h]quinoxaline (abbreviation: 2mDBTBPDBq-II), 2-[3'-(9H-carbazol-9-yl)biphenyl-3-yl]dibenzo[f,h]quinoxaline (abbreviation: 2mCzBPDBq), 2-[4-(3,6-diphenyl-9H-carbazol-9-yl)phenyl]dibenzo[f,h]quinoxaline (abbreviation: 2CzPDBq-III), 7-[3-(dibenzothiophen-4-yl)phenyl]dibenzo[f,h]quinoxaline (abbreviation: 7mDBTPDBq-II), 6-[3-(dibenzothiophen-4-yl)phenyl]dibenzo[f,h]quinoxaline (abbreviation: 6mDBTPDBq-II), 4,6-bis[3-(phenanthren-9-yl)phenyl]pyrimidine (abbreviation: 4,6mPnP2Pm), 4,6-bis[3-(4-dibenzothienyl)phenyl]pyrimidine (abbreviation: 4,6mDBTP2Pm-II), and 4,6-bis[3-(9H-carbazol-9-yl)-phenyl]pyrimidine (abbreviation: 4,6mCzP2Pm); a heterocyclic compound having a triazine skeleton such as 2-{4-[3-(N-phenyl-9H-carbazol-3-yl)-9H-carbazol-9-yl]phenyl}-4,6-diphenyl-1,3,5-triazine (abbreviation: PCCzPTzn); and heterocyclic compounds having pyridine skeletons, such as 3,5-bis[3-(9H-carbazol-9-yl)phenyl]pyridine (abbreviation: 35DCzPPy) and 1,3,5-tri[3-(3-pyridyl)phenyl]benzene (abbreviation: TmPyPB). Among the above materials, the heterocyclic compounds having diazine skeletons, those having triazine skeletons, and those having pyridine skeletons are highly reliable and preferred. In particular, the heterocyclic compounds having diazine (pyrimidine or pyrazine) skeletons and those having triazine skeletons have a high electron-transport property and contribute to a decrease in drive voltage.

As the compound that is preferably used to form the above exciplex and easily accepts holes (the material having a hole-transport property), a π-electron rich heteroaromatic compound (e.g., a carbazole derivative or an indole derivative), an aromatic amine compound, or the like can be favorably used. Specific examples include compounds having aromatic amine skeletons, such as 2-[N-(9-phenylcarbazol-3-yl)-N-phenylamino]spiro-9,9'-bifluorene (abbreviation: PCASF), 4,4',4"-tris[N-(1-naphthyl)-N-phenylamino]triphenylamine (abbreviation: 1'-TNATA), 2,7-bis[N-(4-diphenylaminophenyl)-N-phenylamino]-spiro-9,9'-bifluorene (abbreviation: DPA2SF), N,N'-bis(9-phenylcarbazol-3-yl)-N,N-diphenylbenzene-1,3-diamine (abbreviation: PCA2B), N-(9,9-dimethyl-2-diphenylamino-9H-fluoren-7-yl)diphenylamine (abbreviation: DPNF), N,N',N"-triphenyl-N,N',N"-tris(9-phenylcarbazol-3 -yl)benzene-1,3,5-triamine (abbreviation: PCA3B), 2-[N-(4-diphenylaminophenyl)-N-phenylamino]spiro-9,9'-bifluorene (abbreviation: DPASF), N,N'-bis[4-(carbazol-9-yl)phenyl]-N,N'-diphenyl-9,9-dimethylfluorene-2,7-diamine (abbreviation: YGA2F), NPB, N,N'-bis(3-methylphenyl)-N,N'-diphenyl-[1,1'-biphenyl]-4,4'-diamine (abbreviation: TPD), 4,4'-bis[N-(4-diphenylaminophenyl)-N-phenylamino]biphenyl (abbreviation: DPAB), BSPB, 4-phenyl-4'-(9-phenylfluoren-9-yl)triphenylamine (abbreviation: BPAFLP), 4-phenyl-3'-(9-phenylfluoren-9-yl)triphenylamine (abbreviation: mBPAFLP), N-(9,9-dimethyl-9H-fluoren-2-yl)-N-{9,9-dimethyl-2-[N'-phenyl-N'-(9,9-dimethyl-9H-fluoren-2-yl)amino]-9H-fluoren-7-yl}phenylamine (abbreviation: DFLADFL), PCzPCA1, 3-[N-(4-diphenylaminophenyl)-N-phenylamino]-9-phenylcarbazole (abbreviation: PCzDPA1), 3,6-bis[N-(4-diphenylaminophenyl)-N-phenylamino]-9-phenylcarbazole (abbreviation: PCzDPA2), DNTPD, 3,6-bis[N-(4-diphenylaminophenyl)-N-(1-naphthyl)amino]-9-phenylcarbazole (abbreviation: PCzTPN2), PCzPCA2, 4-phenyl-4'-(9-phenyl-9H-carbazol-3-yl)triphenylamine (abbreviation: PCBA1BP), 4,4'-diphenyl-4"-(9-phenyl-9H-carbazol-3-yl)triphenylamine (abbreviation: PCBBi1BP), 4-(1-naphthyl)-4'-(9-phenyl-9H-carbazol-3-yl)triphenylamine (abbreviation: PCBANB), 4,4'-di(1-naphthyl)-4"-(9-phenyl-9H-carbazol-3-yftriphenylamine (abbreviation: PCBNBB), 3-[N-(1-naphthyl)-N-(9-phenylcarbazol-3-yl)amino]-9-phenylcarbazole (abbreviation: PCzPCN1), 9,9-dimethyl-N-phenyl-N-[4-(9-phenyl-9H-carbazol-3-yl)phenyl]fluoren-2-amine (abbreviation: PCBAF), N-phenyl-N-[4-(9-phenyl-9H-carbazol-3-yl)phenyl]spiro-9,9'-bifluoren-2-amine (abbreviation: PCBASF), N-(4-biphenyl)-N-(9,9-dimethyl-9H-fluoren-2-yl)-9-phenyl-9H-carbazol-3 -amine (abbreviation: PCBiF), and N-(1,1'-biphenyl-4-yl)-N-[4-(9-phenyl-9H-carbazol-3-yl)phenyl]-9,9-dimethyl-9H-fluoren-2-amine (abbreviation: PCBBiF); compounds having carbazole skeletons, such as 1,3-bis(N-carbazolyl)benzene (abbreviation: mCP), CBP, 3,6-bis(3,5-diphenylphenyl)-9-phenylcarbazole (abbreviation: CzTP), and 9-phenyl-9H-3-(9-phenyl-9H-carbazol-3-yl)carbazole (abbreviation: PCCP); compounds having thiophene skeletons, such as 4,4',4"-(benzene-1,3,5-triyl)tri(dibenzothiophene) (abbreviation: DBT3P-II), 2,8-diphenyl-4-[4-(9-phenyl-9H-fluoren-9-yl)phenyl]dibenzothiophene (abbreviation: DBTFLP-III), and 4-[4-(9-phenyl-9H-fluoren-9-yl)phenyl]-6-phenyldibenzothiophene (abbreviation: DBTFLP-IV); and compounds having furan skeletons, such as 4,4',4"-(benzene-1,3,5-triyfltri(dibenzofuran) (abbreviation: DBF3P-II) and 4-{3-[3-(9-phenyl-9H-fluoren-9-yl)phenyl]phenyl}dibenzofuran (abbreviation: mmDBFFLBi-II). Among the above materials, the compounds having aromatic amine skeletons and the compounds having carbazole skeletons are preferred because these compounds are highly reliable and have a high hole-transport property and contribute to a reduction in drive voltage.

Note that in the case where the light-emitting layer 113 contains the above-described organometallic complex (guest material) and the host material, phosphorescence with high emission efficiency can be obtained from the light-emitting layer 113.

Figure 1B:
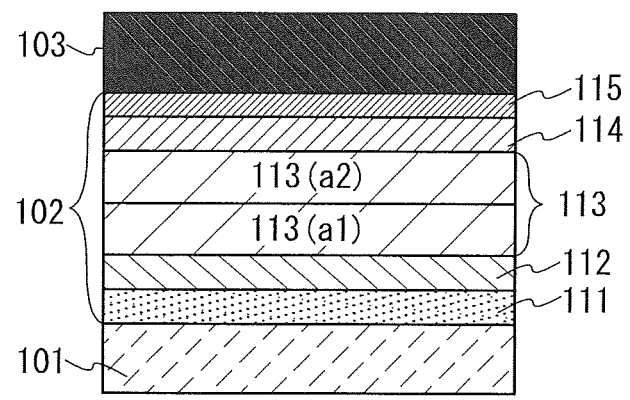

In the light-emitting element, the light-emitting layer 113 does not necessarily have the single-layer structure shown in FIG. 1A and may have a stacked-layer structure including two or more layers as shown in FIG. 1B. In that case, each layer in the stacked-layer structure emits light. For example, fluorescence is obtained from a first light-emitting layer 113(a1), and phosphorescence is obtained from a second light-emitting layer 113(a2) stacked over the first light-emitting layer. Note that the stacking order may be reversed. It is preferable that light emission due to energy transfer from an exciplex to a dopant be obtained from the layer that emits phosphorescence. The emission color of one layer and that of the other layer may be the same or different. In the case where the emission colors are different, a structure in which, for example, blue light from one layer and orange or yellow light or the like from the other layer can be obtained can be formed. Each layer may contain various kinds of dopants.

Note that in the case where the light-emitting layer 113 has a stacked-layer structure, a light-emitting substance converting singlet excitation energy into light emission or a light-emitting substance converting triplet excitation energy into light emission can be used alone or in combination, for example. In that case, the following substances can be used.

As an example of the light-emitting substance converting singlet excitation energy into light emission, a substance which emits fluorescence (a fluorescent compound) can be given.

Examples of the substance emitting fluorescence are N,N'-bis[4-(9H-carbazol-9-yl)phenyl]-N,N'-diphenylstilbene-4,4'-diamine (abbreviation: YGA2S), 4-(9H-carbazol-9-yl)-4'-(10-phenyl-9-anthryl)triphenylamine (abbreviation: YGAPA), 4-(9H-carbazol-9-yl)-4'-(9,10-diphenyl-2-anthryl)triphenylamine (abbreviation: 2YGAPPA), N,9-diphenyl-N-[4-(10-phenyl-9-anthryl)phenyl]-9H-carbazol-3-amine (abbreviation: PCAPA), perylene, 2,5,8,11-tetra(tert-butyl)perylene (abbreviation: TBP), 4-(10-phenyl-9-anthryl)-4'-(9-phenyl-9H-carbazol-3-yl)triphenylamine (abbreviation: PCBAPA), N,N''-(2-tert-butylanthracene-9,10-diyldi-4,1-phenylene)bis[N,N',N'-triphenyl-1,4-phenylenediamine] (abbreviation: DPABPA), N,9-diphenyl-N-[4-(9,10-diphenyl-2-anthryl)phenyl]-9H-carbazol-3-amine (abbreviation: 2PCAPPA), N-[4-(9,10-diphenyl-2-anthryl)phenyl]-N,N',N'-triphenyl-1,4-phenylenediamine (abbreviation: 2DPAPPA), N,N,N',N',N'',N'',N''',N'''-octaphenyldibenzo[g,p]chrysene-2,7,10,15-tetraamine (abbreviation: DBC1), coumarin 30, N-(9,10-diphenyl-2-anthryl)-N,9-diphenyl-9H-carbazol-3-amine (abbreviation: 2PCAPA), N-[9,10-bis(1,1'-biphenyl-2-yl)-2-anthryl]-N,9-diphenyl-9H-carbazol-3-amine (abbreviation: 2PCABPhA), N-(9,10-diphenyl-2-anthryl)-N,N',N'-triphenyl-1,4-phenylenediamine (abbreviation: 2DPAPA), N-[9,10-bis(1,1'-biphenyl-2-yl)-2-anthryl]-N,N',N'-triphenyl-1,4-phenylenediamine (abbreviation: 2DPABPhA), 9,10-bis(1,1'-biphenyl-2-yl)-N-[4-(9H-carbazol-9-yl)phenyl]-N-phenylanthracen-2-amine (abbreviation: 2YGABPhA), N,N,9-triphenylanthracen-9-amine (abbreviation: DPhAPhA), coumarin 545T, N,N'-diphenylquinacridone (abbreviation: DPQd), rubrene, 5,12-bis(1,1'-biphenyl-4-yl)-6,11-diphenyltetracene (abbreviation: BPT), 2-(2-{2-[4-(dimethylamino)phenyl]ethenyl}-6-methyl-4H-pyran-4-ylidene)propanedinitrile (abbreviation: DCM1), 2-{2-methyl-6-[2-(2,3,6,7-tetrahydro-1H,5H-benzo[ij]quinolizin-9-yl)ethenyl]-4H-pyran-4-ylidene}propanedinitrile (abbreviation: DCM2), N,N,N',N'-tetrakis(4-methylphenyl)tetracene-5,11-diamine (abbreviation: p-mPhTD), 7,14-diphenyl-N,N,N',N'-tetrakis(4-methylphenyl)acenaphtho[1,2-a]fluoranthene-3,10-diamine (abbreviation: p-mPhAFD), 2-{2-isopropyl-6-[2-(1,1,7,7-tetramethyl-2,3,6,7-tetrahydro-1H,5H-benzo [ij]quinolizin-9-yl)ethenyl]-4H-pyran-4-ylidene}propanedinitrile (abbreviation: DCJTI), 2-{2-tert-butyl-6-[2-(1,1,7,7-tetramethyl-2,3,6,7-tetrahydro-1H,5H-benzo[ij]quinolizin-9-yl)ethenyl]-4H-pyran-4-ylidene}propanedinitrile (abbreviation: DCJTB), 2-(2,6-bis{2-[4-(dimethylamino)phenyl]ethenyl}-4H-pyran-4-ylidene)propanedinitrile (abbreviation: BisDCM), 2-{2,6-bis[2-(8-methoxy-1,1,7,7-tetramethyl-2,3,6,7-tetrahydro-1H,5H-benzo[ij]quinolizin-9-yl)ethenyl]-4H-pyran-4-ylidene}propanedinitrile (abbreviation: BisDCJTM), and the like.

Examples of the light-emitting substance converting triplet excitation energy into light emission are a substance which emits phosphorescence (a phosphorescent compound) and a thermally activated delayed fluorescent (TADF) material which emits thermally activated delayed fluorescence. Note that "delayed fluorescence" exhibited by the TADF material refers to light emission having the same spectrum as normal fluorescence and an extremely long lifetime. The lifetime is $10^{-6}$ seconds or longer, preferably $10^{-3}$ seconds or longer.

Examples of the substance emitting phosphorescence are bis{2-[3',5'-bis(trifluoromethyl)phenyl]pyridinato-N,$C^{2'}$}iridium(III) picolinate (abbreviation: [Ir(CF$_3$ppy)$_2$(pic)], bis[2-(4',6'-difluorophenyl)pyridinato-N,$C^{2'}$]iridium(III) acetylacetonate (abbreviation: FIracac), tris(2-phenylpyridinato)iridium(III) (abbreviation: [Ir(ppy)$_3$]), bis(2-phenylpyridinato)iridium(III) acetylacetonate (abbreviation: [Ir(ppy)$_2$(acac)]), tris(acetylacetonato)(monophenanthroline)terbium(III) (abbreviation: [Tb(acac)$_3$(Phen)]), bis(benzo quinolinato)iridium(III) acetylacetonate (abbreviation: [Ir(bzq)$_2$(acac)]), bis(2,4-diphenyl-1,3-oxazolato-N,$C^{2'}$)iridium(III) acetylacetonate (abbreviation: [Ir(dpo)$_2$(acac)]), bis{2-[4'-(perfluorophenyl)phenyl]pyridinato-N,$C^{2'}$}iridium(III) acetylacetonate (abbreviation: [Ir(p-PF-ph)$_2$(acac)]), bis(2-phenylbenzothiazolato-N,$C^{2'}$)iridium(III) acetylacetonate (abbreviation: [Ir(bt)$_2$(acac)]), bis[2-(2'-benzo[4,5-a]thienyl)pyridinato-N,$C^{3'}$]iridium(III) acetylacetonate (abbreviation: [Ir(btp)$_2$(acac)]), bis(1-phenylisoquinolinato-N,$C^{2'}$)iridium(III) acetylacetonate (abbreviation: [Ir(piq)$_2$(acac)]), (acetylacetonato)bis[2,3-bis(4-fluorophenyl)quinoxalinato]iridium(III) (abbreviation: [Ir(Fdpq)$_2$(acac)]), (acetylacetonato)bis(3,5-dimethyl-2-phenylpyrazinato)iridium(III) (abbreviation: [Ir(mppr-Me)$_2$(acac)]), (acetylacetonato)bis(5-isopropyl-3-methyl-2-phenylpyrazinato)iridium(III) (abbreviation: [Ir(mppr-iPr)$_2$(acac)]), (acetylacetonato)bis(2,3,5-triphenylpyrazinato)iridium(III) (abbreviation: [Ir(tppr)$_2$(acac)]), bis(2,3,5-triphenylpyrazinato)(dipivaloylmethanato)iridium(III) (abbreviation: [Ir(tppr)$_2$(dpm)], (acetylacetonato)bis(6-tert-butyl-4-phenylpyrimidinato)iridium(III) (abbreviation: [Ir(tBuppm)$_2$(acac)]), (acetylacetonato)bis(4,6-diphenylpyrimidinato)iridium(III) (abbreviation: [Ir(dppm)$_2$(acac)]), 2,3,7,8,12,13,17,18-octaethyl-21H,23H-porphyrin platinum (II) (abbreviation: PtOEP), tris(1,3-diphenyl-1,3-propanedionato)(monophenanthroline)europium(III) (abbreviation: [Eu(DBM)$_3$(Phen)]), tris[1-(2-thenoyl)-3,3,3-trifluoroacetonato](monophenanthroline)europium(III) (abbreviation: [Eu(TTA)$_3$(Phen)]), and the like.

Examples of the TADF material are fullerene, a derivative thereof, an acridine derivative such as proflavine, eosin, and the like. Other examples are a metal-containing porphyrin, such as a porphyrin containing magnesium (Mg), zinc (Zn), cadmium (Cd), tin (Sn), platinum (Pt), indium (In), or palladium (Pd). Examples of the metal-containing porphyrin are a protoporphyrin-tin fluoride complex (SnF$_2$(Proto IX)), a mesoporphyrin-tin fluoride complex (SnF$_2$(Meso IX)), a hematoporphyrin-tin fluoride complex (SnF$_2$(Hemato IX)), a coproporphyrin tetramethyl ester-tin fluoride complex (SnF$_2$(Copro III-4Me)), an octaethylporphyrin-tin fluoride complex (SnF$_2$(OEP)), an etioporphyrin-tin fluoride complex (SnF$_2$(Etio I)), an octaethylporphyrin-platinum chloride complex (PtCl$_2$OEP), and the like. Alternatively, a heterocyclic compound including a π-electron rich heteroaromatic ring and a π-electron deficient heteroaromatic ring can be used, such as 2-(biphenyl-4-yl)-4,6-bis(12-phenylindolo[2,3-a]carbazol-11-yl)-1,3,5-triazine (PIC-TRZ). Note that a material in which the π-electron rich heteroaromatic ring is directly bonded to the π-electron deficient heteroaromatic ring is particularly preferably used because both the donor property of the π-electron rich heteroaromatic ring and the acceptor property of the π-electron deficient heteroaromatic ring are increased and the energy difference between the S1 level and the T1 level becomes small.

The electron-transport layer 114 is a layer containing a substance having a high electron-transport property (also referred to as an electron-transport compound). For the electron-transport layer 114, a metal complex such as tris (8-quinolinolato)aluminum (abbreviation: Alq$_3$), tris(4-methyl-8-quinolinolato)aluminum (abbreviation: Almq$_3$), BeBq$_2$, BAlq, bis[2-(2-hydroxyphenyl)benzoxazolato] zinc (abbreviation: Zn(BOX)$_2$), or bis[2-(2-hydroxyphenyl)benzothiazolato]zinc (abbreviation: Zn(BTZ)$_2$) can be used. Alternatively, a heteroaromatic compound such as PBD, 1,3-bis[5-(p-tert-butylphenyl)-1,3,4-oxadiazol-2-yl]benzene (abbreviation: OXD-7), TAZ, 3-(4-tert-butylphenyl)-4-(4-ethylphenyl)-5-(4-biphenylyl)-1,2,4-triazole (abbreviation: p-EtTAZ), bathophenanthroline (abbreviation: BPhen), bathocuproine (abbreviation: BCP), or 4,4'-bis(5-methylbenzoxazol-2-yl)stilbene (abbreviation: BzOs) can also be used. A high molecular compound such as poly(2,5-pyridinediyl) (abbreviation: PPy), poly[(9,9-dihexylfluorene-2,7-diyl)-co-(pyridine-3,5-diyl)] (abbreviation: PF-Py), or poly[(9,9-dioctylfluorene-2,7-diyl)-co-(2,2'-bipyridine-6,6'-diyl)] (abbreviation: PF-BPy) can also be used. The substances listed here are mainly ones that have an electron mobility of $10^{-6}$ cm$^2$/Vs or higher. Note that any substance other than the substances listed here may be used for the electron-transport layer 114 as long as the electron-transport property is higher than the hole-transport property.

The electron-transport layer 114 is not limited to a single layer, but may be a stack of two or more layers each containing any of the substances listed above.

The electron-injection layer 115 is a layer containing a substance having a high electron-injection property. For the electron-injection layer 115, an alkali metal, an alkaline earth metal, or a compound thereof, such as lithium fluoride (LiF), cesium fluoride (CsF), calcium fluoride (CaF$_2$), or lithium oxide (LiO$_x$) can be used. A rare earth metal compound like erbium fluoride (ErF$_3$) can also be used. An electride may also be used for the electron-injection layer 115. Examples of the electride include a substance in which electrons are added at high concentration to calcium oxide-aluminum oxide. Any of the substances for forming the electron-transport layer 114, which are given above, can be used.

A composite material in which an organic compound and an electron donor (donor) are mixed may also be used for the electron-injection layer 115. Such a composite material is excellent in an electron-injection property and an electron-transport property because electrons are generated in the organic compound by the electron donor. In this case, the organic compound is preferably a material that is excellent in transporting the generated electrons. Specifically, for example, the substances for forming the electron-transport layer 114 (e.g., a metal complex or a heteroaromatic compound), which are given above, can be used. As the electron donor, a substance showing an electron-donating property with respect to the organic compound may be used. Specifically, an alkali metal, an alkaline earth metal, and a rare earth metal are preferable, and lithium, cesium, magnesium, calcium, erbium, ytterbium, and the like are given. In addition, an alkali metal oxide or an alkaline earth metal oxide is preferable, and lithium oxide, calcium oxide, barium oxide, and the like are given. A Lewis base such as magnesium oxide can also be used. An organic compound such as tetrathiafulvalene (abbreviation: TTF) can also be used.

Note that each of the hole-injection layer 111, the hole-transport layer 112, the light-emitting layer 113, the electron-transport layer 114, the electron-injection layer 115 can be formed by any one or any combination of the following methods: an evaporation method (including a vacuum evaporation method), a printing method (such as relief printing, intaglio printing, gravure printing, planography printing, and stencil printing), an ink-jet method, a coating method, and the like. Besides the above-mentioned materials, an inorganic compound such as a quantum dot or a high molecular compound (e.g., an oligomer, a dendrimer, or a polymer) may be used for the hole-injection layer 111, the hole-transport layer 112, the light-emitting layer 113, the electron-transport layer 114, and the electron-injection layer 115, which are described above.

In the above-described manner, a light-emitting element in which an EL layer is sandwiched between a pair of electrodes can be manufactured.

The structure described in this embodiment can be used in appropriate combination with any of the structures described in the other embodiments.

Embodiment 3

In this embodiment, a light-emitting element (hereinafter referred to as a tandem light-emitting element) which is one embodiment of the present invention and includes a plurality of EL layers is described.

Figure 2A:
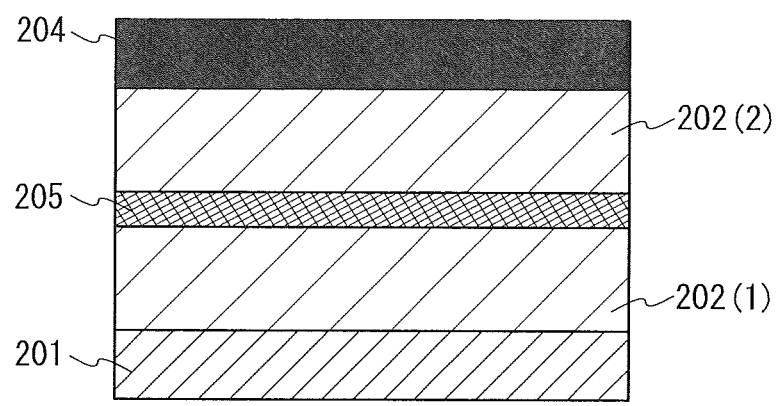
FIGS. 2A and 2B illustrate structures of light-emitting elements.

A light-emitting element described in this embodiment is a tandem light-emitting element including, between a pair of electrodes (a first electrode 201 and a second electrode 204), a plurality of EL layers (a first EL layer 202(1) and a second EL layer 202(2)) and a charge-generation layer 205 provided therebetween, as illustrated in FIG. 2A.

In this embodiment, the first electrode 201 functions as an anode, and the second electrode 204 functions as a cathode. Note that the first electrode 201 and the second electrode 204 can have structures similar to those described in Embodiment 2. In addition, either or both of the EL layers (the first EL layer 202(1) and the second EL layer 202(2)) may have structures similar to those described in Embodiment 2. In other words, the structures of the first EL layer 202(1) and the second EL layer 202(2) may be the same as or different from each other. When the structures are the same, Embodiment 2 can be referred to.

The charge-generation layer 205 provided between the plurality of EL layers (the first EL layer 202(1) and the second EL layer 202(2)) has a function of injecting electrons into one of the EL layers and injecting holes into the other of the EL layers when a voltage is applied between the first electrode 201 and the second electrode 204. In this embodiment, when a voltage is applied such that the potential of the first electrode 201 is higher than that of the second electrode 204, the charge-generation layer 205 injects electrons into the first EL layer 202(1) and injects holes into the second EL layer 202(2).

Note that in terms of light extraction efficiency, the charge-generation layer 205 preferably has a property of transmitting visible light (specifically, the charge-generation layer 205 has a visible light transmittance of 40% or more). The charge-generation layer 205 functions even when it has lower conductivity than the first electrode 201 or the second electrode 204.

The charge-generation layer 205 may have either a structure in which an electron acceptor (acceptor) is added to an organic compound having a high hole-transport property or a structure in which an electron donor (donor) is added to an organic compound having a high electron-transport property. Alternatively, both of these structures may be stacked.

In the case of the structure in which an electron acceptor is added to an organic compound having a high hole-transport property, as the organic compound having a high hole-transport property, the substances having a high hole-transport property which are given in Embodiment 2 as the substances used for the hole-injection layer 111 and the hole-transport layer 112 can be used. For example, an aromatic amine compound such as NPB, TPD, TDATA, MTDATA, or BSPB, or the like can be used. The substances listed here are mainly ones that have a hole mobility of $10^{-6}$ cm$^2$/Vs or higher. Note that any organic compound other than the compounds listed here may be used as long as the hole-transport property is higher than the electron-transport property.

As the electron acceptor, 7,7,8,8-tetracyano-2,3,5,6-tetrafluoroquinodimethane (abbreviation: F$_4$-TCNQ), chloranil, and the like can be given. Oxides of metals belonging to Groups 4 to 8 of the periodic table can also be given. Specifically, vanadium oxide, niobium oxide, tantalum oxide, chromium oxide, molybdenum oxide, tungsten oxide, manganese oxide, and rhenium oxide are preferable because of their high electron-accepting properties. Among these, molybdenum oxide is especially preferable because it is stable in the air, has a low hygroscopic property, and is easy to handle.

In the case of the structure in which an electron donor is added to an organic compound having a high electron-transport property, as the organic compound having a high electron-transport property, the substances having a high electron-transport property which are given in Embodiment 2 as the substances used for the electron-transport layer 114 can be used. For example, a metal complex having a quinoline skeleton or a benzoquinoline skeleton, such as Alq, Almq$_3$, BeBq$_2$, or BAlq, or the like can be used. Alternatively, a metal complex having an oxazole-based ligand or a thiazole-based ligand, such as Zn(BOX)$_2$ or Zn(BTZ)$_2$ can be used. Alternatively, in addition to such a metal complex, PBD, OXD-7, TAZ, Bphen, BCP, or the like can be used. The substances listed here are mainly ones that have an electron mobility of $10^{-6}$ cm$^2$/Vs or higher. Note that any organic compound other than the compounds listed here may be used as long as the electron-transport property is higher than the hole-transport property.

As the electron donor, it is possible to use an alkali metal, an alkaline earth metal, a rare earth metal, metals belonging to Groups 2 and 13 of the periodic table, or an oxide or carbonate thereof Specifically, lithium (Li), cesium (Cs), magnesium (Mg), calcium (Ca), ytterbium (Yb), indium (In), lithium oxide, cesium carbonate, or the like is preferably used. Alternatively, an organic compound such as tetrathianaphthacene may be used as the electron donor.

Note that forming the charge-generation layer 205 by using any of the above materials can suppress a drive voltage increase caused by the stack of the EL layers. The charge-generation layer 205 can be formed by any one or any combination of the following methods: an evaporation method (including a vacuum evaporation method), a printing method (such as relief printing, intaglio printing, gravure printing, planography printing, and stencil printing), an ink jet method, a coating method, and the like.

Figure 2B:
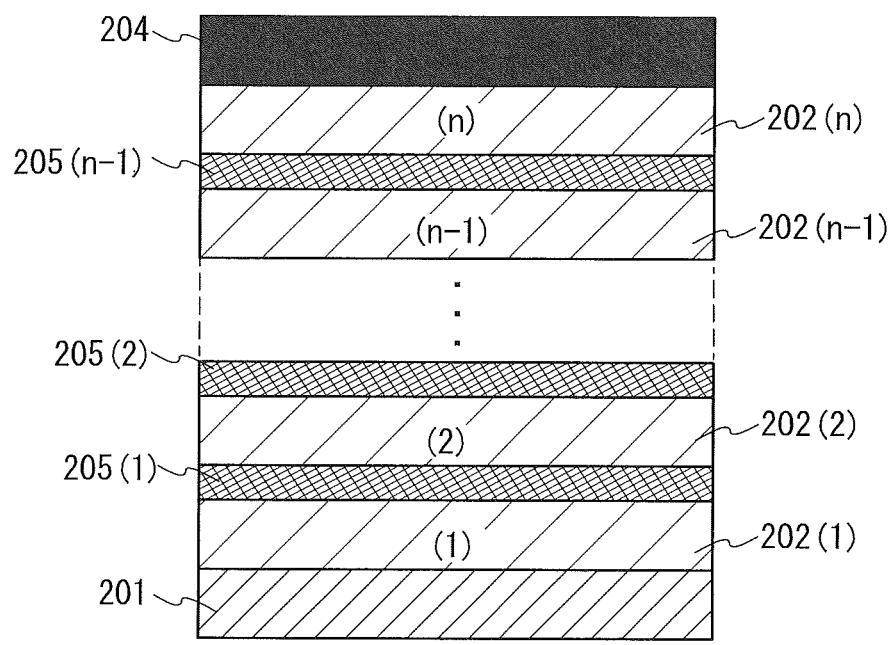

Although the light-emitting element including two EL layers is described in this embodiment, the present invention can be similarly applied to a light-emitting element in which n EL layers (202(1) to 202(n)) (n is three or more) are stacked as illustrated in FIG. 2B. In the case where a plurality of EL layers are included between a pair of electrodes as in the light-emitting element according to this embodiment, by providing charge-generation layers (205(1) to 205(n−1)) between the EL layers, light emission in a high luminance region can be obtained with current density kept low. Since the current density can be kept low, the element can have a long lifetime.

When the EL layers have different emission colors, a desired emission color can be obtained from the whole light-emitting element. For example, in a light-emitting element having two EL layers, when an emission color of the first EL layer and an emission color of the second EL layer are complementary colors, the light-emitting element can emit white light as a whole. Note that "complementary colors" refer to colors that can produce an achromatic color when mixed. In other words, mixing light of complementary colors allows white light emission to be obtained. Specifically, a combination in which blue light emission is obtained from the first EL layer and yellow or orange light emission is obtained from the second EL layer is given as an example. In that case, it is not necessary that both of blue light emission and yellow (or orange) light emission are fluorescence, and the both are not necessarily phosphorescence. For example, a combination in which blue light emission is fluorescence and yellow (or orange) light emission is phosphorescence or a combination in which blue light emission is phosphorescence and yellow (or orange) light emission is fluorescence may be employed.

The same can be applied to a light-emitting element having three EL layers. For example, the light-emitting element as a whole can provide white light emission when the emission color of the first EL layer is red, the emission color of the second EL layer is green, and the emission color of the third EL layer is blue.

The structure described in this embodiment can be used in appropriate combination with any of the structures described in the other embodiments.

Embodiment 4

In this embodiment, a light-emitting device which is one embodiment of the present invention is described.

The light-emitting device may be either a passive matrix light-emitting device or an active matrix light-emitting device. Any of the light-emitting elements described in other embodiments can be used in the light-emitting device described in this embodiment.

In this embodiment, first, an active matrix light-emitting device is described with reference to FIGS. 3A to 3C.

Figure 3A:
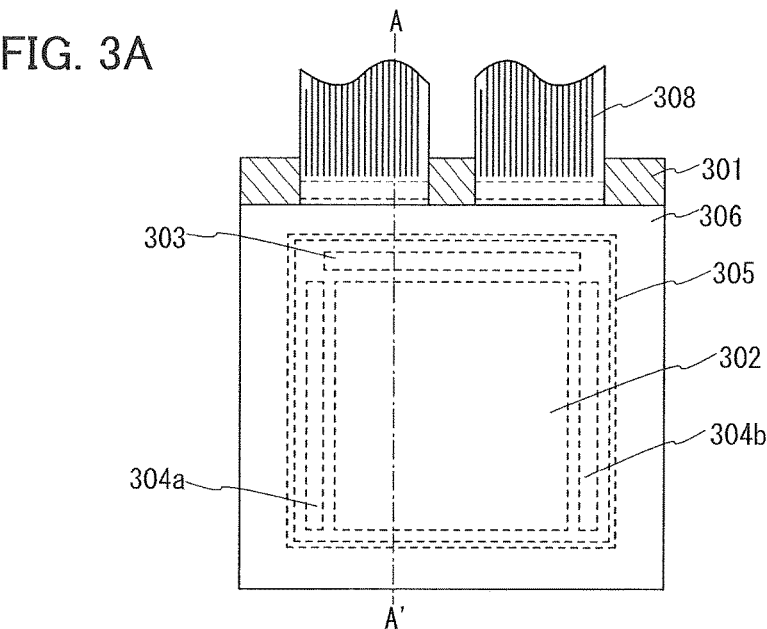
FIGS. 3A to 3C illustrate light-emitting devices.
Figure 3B:
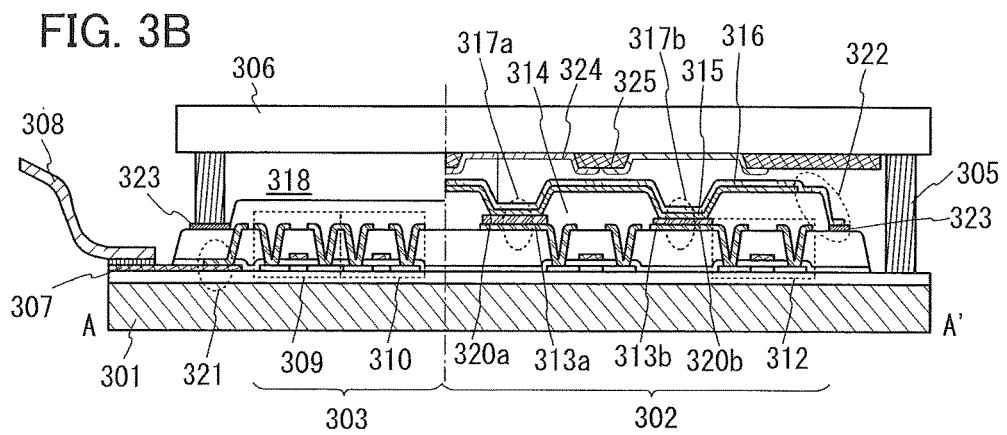
Figure 3C:
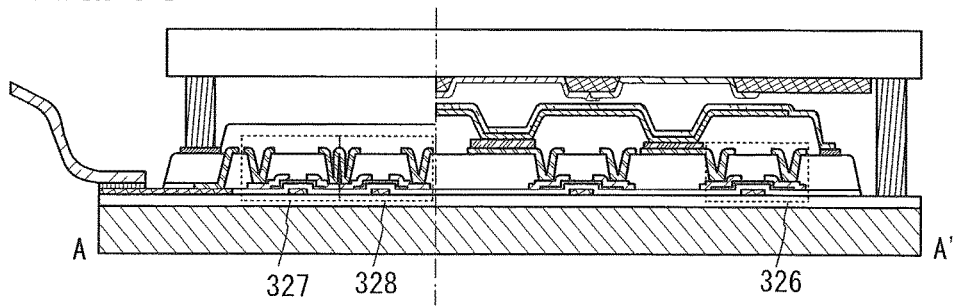

Note that FIG. 3A is a top view illustrating a light-emitting device and FIG. 3B is a cross-sectional view taken along the chain line A-A' in FIG. 3A. The active matrix light-emitting device of one embodiment of the present invention includes a pixel portion 302 provided over an element substrate 301, a driver circuit portion (a source line driver circuit) 303, and driver circuit portions (gate line driver circuits) 304a and 304b. The pixel portion 302, the driver circuit portion 303, and the driver circuit portions 304a and 304b are sealed between the element substrate 301 and a sealing substrate 306 with a sealant 305.

In addition, over the element substrate 301, a lead wiring 307 for connecting an external input terminal, through which a signal (e.g., a video signal, a clock signal, a start signal, or a reset signal) or an potential from the outside is transmitted to the driver circuit portion 303 and the driver circuit portions 304a and 304b, is provided. Here, an example is described in which a flexible printed circuit (FPC) 308 is provided as the external input terminal. Although only the FPC is illustrated here, the FPC may be provided with a printed wiring board (PWB). The light-emitting device in this specification includes, in its category, not only the light-emitting device itself but also the light-emitting device provided with the FPC or the PWB.

Next, a cross-sectional structure is described with reference to FIG. 3B. The driver circuit portions and the pixel portion are formed over the element substrate 301; the driver circuit portion 303 that is the source line driver circuit and the pixel portion 302 are illustrated here.

The driver circuit portion 303 is an example in which an FET 309 and an FET 310 are combined. Note that the driver circuit portion 303 may be formed with a circuit including transistors having the same conductivity type (either n-channel transistors or p-channel transistors) or a CMOS circuit including an n-channel transistor and a p-channel transistor. Although this embodiment shows a driver integrated type in which the driver circuit is formed over the substrate, the driver circuit is not necessarily formed over the substrate, and may be formed outside the substrate.

The pixel portion 302 includes a switching FET (not shown) and a current control FET 312, and a wiring of the current control FET 312 (a source electrode or a drain electrode) is electrically connected to first electrodes (anodes) (313a and 313b) of light-emitting elements 317a and 317b. Although the pixel portion 302 includes two FETs (the switching FET and the current control FET 312) in this embodiment, one embodiment of the present invention is not limited thereto. The pixel portion 302 may include, for example, three or more FETs and a capacitor in combination.

As the FETs 309, 310, and 312, for example, a staggered transistor or an inverted staggered transistor can be used. Examples of a semiconductor material that can be used for the FETs 309, 310, and 312 are a Group 13 semiconductor, a Group 14 semiconductor (e.g., silicon), a compound semiconductor, an oxide semiconductor, and an organic semiconductor material. In addition, there is no particular limitation on the crystallinity of the semiconductor material, and an amorphous semiconductor film or a crystalline semiconductor film can be used. In particular, an oxide semiconductor is preferably used for the FETs 309, 310, 311, and 312. Examples of the oxide semiconductor are In—Ga oxides, In-M-Zn oxides (M is Al, Ga, Y, Zr, La, Ce, Hf, or Nd), and the like. For example, an oxide semiconductor material that has an energy gap of 2 eV or more, preferably 2.5 eV or more, further preferably 3 eV or more is used, so that the off-state current of the transistors can be reduced.

In addition, conductive films (320a and 320b) for optical adjustment are stacked over the first electrodes 313a and 313b. For example, as illustrated in FIG. 3B, in the case where the wavelengths of light extracted from the light-emitting elements 317a and 317b are different from each other, the thicknesses of the conductive films 320a and 320b are different from each other. In addition, an insulator 314 is formed to cover end portions of the first electrodes (313a and 313b). In this embodiment, the insulator 314 is formed using a positive photosensitive acrylic resin. The first electrodes (313a and 313b) are used as anodes in this embodiment.

The insulator 314 preferably has a curved surface with curvature at an upper end portion or a lower end portion thereof. This enables favorable coverage by a film to be formed over the insulator 314. The insulator 314 can be formed using, for example, either a negative photosensitive resin or a positive photosensitive resin. The material for the insulator 314 is not limited to an organic compound and an inorganic compound such as silicon oxide, silicon oxynitride, or silicon nitride can also be used.

An EL layer 315 and a second electrode 316 are stacked over the first electrodes (313a and 313b). In the EL layer 315, at least a light-emitting layer is provided. In the light-emitting elements (317a and 317b) including the first electrodes (313a and 313b), the EL layer 315, and the second electrode 316, an end portion of the EL layer 315 is covered with the second electrode 316. The structure of the EL layer 315 may be the same as or different from the single-layer structure and the stacked layer structure described in Embodiments 2 and 3. Furthermore, the structure may differ between the light-emitting elements.

For the first electrode 313, the EL layer 315, and the second electrode 316, any of the materials given in Embodiment 2 can be used. The first electrodes (313a and 313b) of the light-emitting elements (317a and 317b) are electrically connected to a lead wiring 307 in a region 321, so that an external signal is input through the FPC 308. The second electrode 316 in the light-emitting elements (317a and 317b) is electrically connected to a lead wiring 323 in a region 322, so that an external signal is input through the FPC 308 although it is not shown.

Although the cross-sectional view in FIG. 3B illustrates only the two light-emitting elements 317, a plurality of light-emitting elements are arranged in a matrix in the pixel portion 302. Specifically, in the pixel portion 302, light-emitting elements that emit light of two kinds of colors (e.g., B and Y), light-emitting elements that emit light of three kinds of colors (e.g., R, G, and B), light-emitting elements that emit light of four kinds of colors (e.g. (R, G, B, and Y) or (R, G, B, and W)), or the like are formed so that a light-emitting device capable of full color display can be obtained. In such cases, full color display may be achieved as follows: materials different according to the emission colors or the like of the light-emitting elements are used to form light-emitting layers (so-called separate coloring formation); alternatively, the plurality of light-emitting elements share one light-emitting layer formed using the same material and further include color filters. Thus, the light-emitting elements that emit light of a plurality of kinds of colors are used in combination, so that effects such as an improvement in color purity and a reduction in power consumption can be achieved. Furthermore, the light-emitting device may have improved emission efficiency and reduced power consumption by combination with quantum dots.

The sealing substrate 306 is attached to the element substrate 301 with the sealant 305, whereby the light-emitting elements 317a and 317b are provided in a space 318 surrounded by the element substrate 301, the sealing substrate 306, and the sealant 305.

The sealing substrate 306 is provided with coloring layers (color filters) 324, and a black layer (black matrix) 325 is provided between adjacent coloring layers. Note that one or both of the adjacent coloring layers (color filters) 324 may be provided so as to partly overlap with the black layer (black matrix) 325. Light emission obtained from the light-emitting elements 317a and 317b is extracted through the coloring layers (color filters) 324.

Note that the space 318 may be filled with an inert gas (such as nitrogen or argon) or the sealant 305. In the case where the sealant is applied for attachment of the substrates, one or more of LTV treatment, heat treatment, and the like are preferably performed.

An epoxy-based resin or glass frit is preferably used for the sealant 305. The material preferably allows as little moisture and oxygen as possible to penetrate. As the sealing substrate 306, a glass substrate, a quartz substrate, or a plastic substrate formed of fiber-reinforced plastic (FRP), poly(vinyl fluoride) (PVF), polyester, acrylic, or the like can be used. In the case where glass frit is used as the sealant, the element substrate 301 and the sealing substrate 306 are preferably glass substrates for high adhesion.

Structures of the FETs electrically connected to the light-emitting elements may be different from those in FIG. 3B in the position of a gate electrode; that is, the structures of a FET 326, a FET 327, and a FET 328 as illustrated in FIG.

3C may be employed. The coloring layer (color filter) 324 with which the sealing substrate 306 is provided may be provided as illustrated in FIG. 3C such that, at a position where the coloring layer (color filter) 324 overlaps with the black layer (black matrix) 325, the coloring layer (color filter) 324 further overlaps with an adjacent coloring layer (color filter) 324.

As described above, the active matrix light-emitting device can be obtained.

The light-emitting device of one embodiment of the present invention may be of the passive matrix type, as well as the active matrix type described above.

Figure 4A:
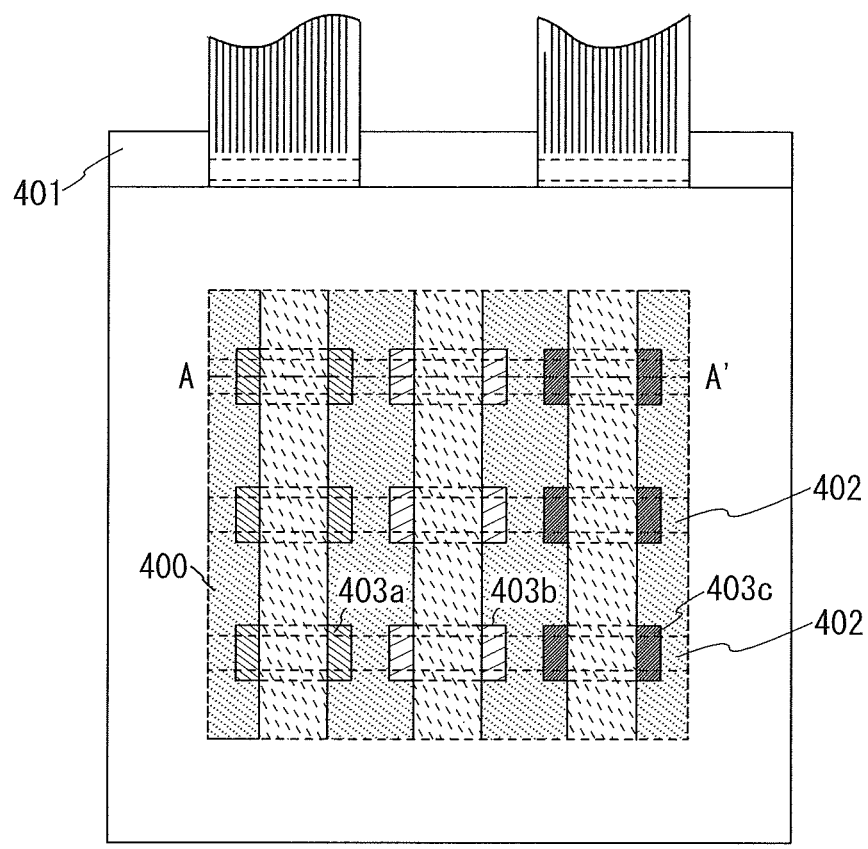
FIGS. 4A and 4B illustrate a light-emitting device.
Figure 4B:
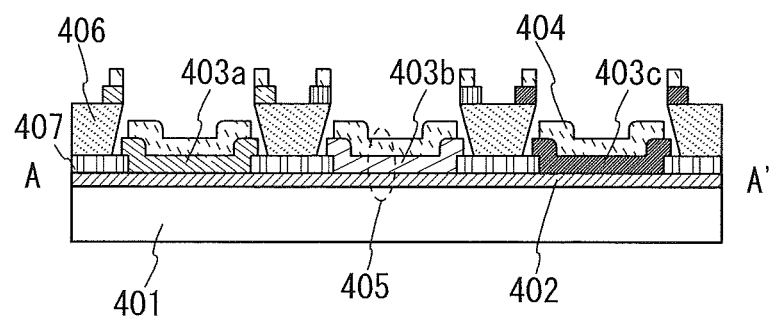

FIGS. 4A and 4B illustrate a passive-matrix light-emitting device. FIG. 4A is a top view of the passive-matrix light-emitting device, and FIG. 4B is a cross-sectional view thereof.

As illustrated in FIGS. 4A and 4B, light-emitting elements 405 including a first electrode 402, EL layers (403a, 403b, and 403c), and second electrodes 404 are formed over a substrate 401. Note that the first electrode 402 has an island-like shape, and a plurality of the first electrodes 402 are formed in one direction (the lateral direction in FIG. 4A) to form a striped pattern. An insulating film 407 is formed over part of the first electrode 402. A partition 406 formed using an insulating material is provided over the insulating film 407. The sidewalls of the partition 406 slope so that the distance between one sidewall and the other sidewall gradually decreases toward the surface of the substrate as illustrated in FIG. 4B.

Since the insulating film 407 is formed over the part of the first electrode 402, the EL layers (403a, 403b, and 403c) and second electrodes 404 which are divided as desired can be formed over the first electrode 402. In the example in FIGS. 4A and 4B, a mask such as a metal mask and the partition 406 over the insulating film 407 are employed to form the EL layers (403a, 403b, and 403c) and the second electrodes 404. In this example, the EL layer 403a, the EL layer 403b, and the EL layer 403c emit light of different colors (e.g., red, green, blue, yellow, orange, and white).

After the formation of the EL layers (403a, 403b, and 403c), the second electrodes 404 are formed. Thus, the second electrode 404 is formed over the EL layers (403a, 403b, and 403c) without contact with the first electrode 402.

Note that sealing can be performed by a method similar to that used for the active matrix light-emitting device, and description thereof is not made.

As described above, the passive matrix light-emitting device can be obtained.

Note that in this specification and the like, a transistor or a light-emitting element can be formed using any of a variety of substrates, for example. The type of a substrate is not limited to a certain type. As the substrate, a semiconductor substrate (e.g., a single crystal substrate or a silicon substrate), an SOI substrate, a glass substrate, a quartz substrate, a plastic substrate, a metal substrate, a stainless steel substrate, a substrate including stainless steel foil, a tungsten substrate, a substrate including tungsten foil, a flexible substrate, an attachment film, paper including a fibrous material, a base material film, or the like can be used, for example. As an example of a glass substrate, a barium borosilicate glass substrate, an aluminoborosilicate glass substrate, a soda lime glass substrate, or the like can be given. Examples of the flexible substrate, the attachment film, the base film, and the like are substrates of plastics typified by polyethylene terephthalate (PET), polyethylene naphthalate (PEN), polyether sulfone (PES), and polytetrafluoroethylene (PTFE). Another example is a synthetic resin such as acrylic. Alternatively, polypropylene, polyester, polyvinyl fluoride, polyvinyl chloride, or the like can be used. Alternatively, polyamide, polyimide, aramid, epoxy, an inorganic vapor deposition film, paper, or the like can be used. Specifically, the use of semiconductor substrates, single crystal substrates, SOI substrates, or the like enables the manufacture of small-sized transistors with a small variation in characteristics, size, shape, or the like and with high current supply capability. A circuit using such transistors achieves low power consumption of the circuit or high integration of the circuit.

Alternatively, a flexible substrate may be used as the substrate, and a transistor or a light-emitting element may be provided directly on the flexible substrate. Still alternatively, a separation layer may be provided between the substrate and the transistor or the light-emitting element. The separation layer can be used when part or the whole of a semiconductor device formed over the separation layer is separated from the substrate and transferred onto another substrate. In such a case, the transistor or the light-emitting element can be transferred to a substrate having low heat resistance or a flexible substrate. For the separation layer, a stack including inorganic films, which are a tungsten film and a silicon oxide film, or an organic resin film of polyimide or the like formed over a substrate can be used, for example.

In other words, a transistor or a light-emitting element may be formed using one substrate, and then transferred to another substrate. Examples of a substrate to which a transistor or a light-emitting element is transferred are, in addition to the above-described substrates over which a transistor or a light-emitting element can be formed, a paper substrate, a cellophane substrate, an aramid film substrate, a polyimide film substrate, a stone substrate, a wood substrate, a cloth substrate (including a natural fiber (e.g., silk, cotton, or hemp), a synthetic fiber (e.g., nylon, polyurethane, or polyester), a regenerated fiber (e.g., acetate, cupra, rayon, or regenerated polyester), or the like), a leather substrate, a rubber substrate, and the like. When such a substrate is used, a transistor with excellent characteristics or a transistor with low power consumption can be formed, a device with high durability or high heat resistance can be provided, or a reduction in weight or thickness can be achieved.

The structure described in this embodiment can be used in appropriate combination with any of the structures described in the other embodiments.

Embodiment 5

In this embodiment, examples of a variety of electronic devices and an automobile manufactured using a light-emitting device which is one embodiment of the present invention are described.

Examples of the electronic device including the light-emitting device are television devices (also referred to as TV or television receivers), monitors for computers and the like, digital cameras, digital video cameras, digital photo frames, cellular phones (also referred to as portable telephone devices), portable game consoles, portable information terminals, audio playback devices, large game machines such as pachinko machines, and the like. Specific examples of the electronic devices are illustrated in FIGS. 5A to 5D, 5D'-1, and 5D'-2.

FIG. 5A illustrates an example of a television device. In the television device 7100, a display portion 7103 is incorporated in a housing 7101. The display portion 7103 can display images and may be a touch panel (an input/output device) including a touch sensor (an input device). Note that the light-emitting device which is one embodiment of the present invention can be used for the display portion 7103. In addition, here, the housing 7101 is supported by a stand 7105.

The television device 7100 can be operated by an operation switch of the housing 7101 or a separate remote controller 7110. With operation keys 7109 of the remote controller 7110, channels and volume can be controlled and images displayed on the display portion 7103 can be controlled. Furthermore, the remote controller 7110 may be provided with a display portion 7107 for displaying data output from the remote controller 7110.

Note that the television device 7100 is provided with a receiver, a modem, and the like. With the use of the receiver, general television broadcasts can be received. Moreover, when the television device is connected to a communication network with or without wires via the modem, one-way (from a sender to a receiver) or two-way (between a sender and a receiver or between receivers) information communication can be performed.

FIG. 5B illustrates a computer, which includes a main body 7201, a housing 7202, a display portion 7203, a keyboard 7204, an external connection port 7205, a pointing device 7206, and the like. Note that this computer can be manufactured using the light-emitting device which is one embodiment of the present invention for the display portion 7203. The display portion 7203 may be a touch panel (an input/output device) including a touch sensor (an input device).

FIG. 5C illustrates a smart watch, which includes a housing 7302, a display portion 7304, operation buttons 7311 and 7312, a connection terminal 7313, a band 7321, a clasp 7322, and the like.

The display portion 7304 mounted in the housing 7302 serving as a bezel includes a non-rectangular display region. The display portion 7304 can display an icon 7305 indicating time, another icon 7306, and the like. The display portion 7304 may be a touch panel (an input/output device) including a touch sensor (an input device).

The smart watch illustrated in FIG. 5C can have a variety of functions, such as a function of displaying a variety of information (e.g., a still image, a moving image, and a text image) on a display portion, a touch panel function, a function of displaying a calendar, date, time, and the like, a function of controlling processing with a variety of software (programs), a wireless communication function, a function of being connected to a variety of computer networks with a wireless communication function, a function of transmitting and receiving a variety of data with a wireless communication function, and a function of reading program or data stored in a recording medium and displaying the program or data on a display portion.

The housing 7302 can include a speaker, a sensor (a sensor having a function of measuring force, displacement, position, speed, acceleration, angular velocity, rotational frequency, distance, light, liquid, magnetism, temperature, chemical substance, sound, time, hardness, electric field, current, voltage, electric power, radiation, flow rate, humidity, gradient, oscillation, odor, or infrared rays), a microphone, and the like. Note that the smart watch can be manufactured using the light-emitting device for the display portion 7304.

FIGS. 5D, 5D'-1, and 5D'-2 illustrate an example of a cellular phone (e.g., smartphone). A cellular phone 7400 includes a housing 7401 provided with a display portion 7402, a microphone 7406, a speaker 7405, a camera 7407, an external connection portion 7404, an operation button 7403, and the like. In the case where a light-emitting device is manufactured by forming a light-emitting element of one embodiment of the present invention over a flexible substrate, the light-emitting element can be used for the display portion 7402 having a curved surface as illustrated in FIG. 5D.

When the display portion 7402 of the cellular phone 7400 illustrated in FIG. 5D is touched with a finger or the like, data can be input to the cellular phone 7400. In addition, operations such as making a call and composing e-mail can be performed by touch on the display portion 7402 with a finger or the like.

There are mainly three screen modes of the display portion 7402. The first mode is a display mode mainly for displaying an image. The second mode is an input mode mainly for inputting data such as characters. The third mode is a display-and-input mode in which two modes of the display mode and the input mode are combined.

For example, in the case of making a call or creating e-mail, a character input mode mainly for inputting characters is selected for the display portion 7402 so that characters displayed on the screen can be input. In this case, it is preferable to display a keyboard or number buttons on almost the entire screen of the display portion 7402.

When a detection device such as a gyroscope or an acceleration sensor is provided inside the cellular phone 7400, display on the screen of the display portion 7402 can be automatically changed by determining the orientation of the cellular phone 7400 (whether the cellular phone is placed horizontally or vertically for a landscape mode or a portrait mode).

The screen modes are changed by touch on the display portion 7402 or operation with the operation button 7403 of the housing 7401. The screen modes can be switched depending on the kind of images displayed on the display portion 7402. For example, when a signal of an image displayed on the display portion is a signal of moving image data, the screen mode is switched to the display mode. When the signal is a signal of text data, the screen mode is switched to the input mode.

Moreover, in the input mode, if a signal detected by an optical sensor in the display portion 7402 is detected and the input by touch on the display portion 7402 is not performed for a certain period, the screen mode may be controlled so as to be changed from the input mode to the display mode.

The display portion 7402 may function as an image sensor. For example, an image of a palm print, a fingerprint, or the like is taken by touch on the display portion 7402 with the palm or the finger, whereby personal authentication can be performed. In addition, by providing a backlight or a sensing light source that emits near-infrared light in the display portion, an image of a finger vein, a palm vein, or the like can be taken.

The light-emitting device can be used for a cellular phone having a structure illustrated in FIG. 5D'-1 or FIG. 5D'-2, which is another structure of the cellular phone (e.g., a smartphone).

Note that in the case of the structure illustrated in FIG. 5D'-1 or FIG. 5D'-2, text data, image data, or the like can be displayed on second screens 7502(1) and 7502(2) of housings 7500(1) and 7500(2) as well as first screens 7501(1) and 7501(2). Such a structure enables a user to easily see text data, image data, or the like displayed on the second screens 7502(1) and 7502(2) while the cellular phone is placed in user's breast pocket.

Figure 6A:
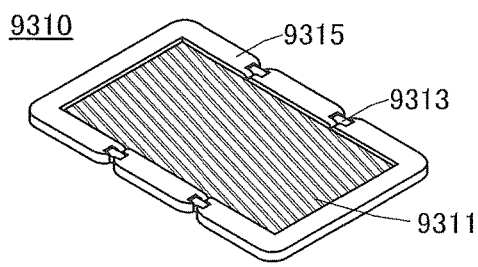
FIGS. 6A to 6C illustrate an electronic device.
Figure 6B:
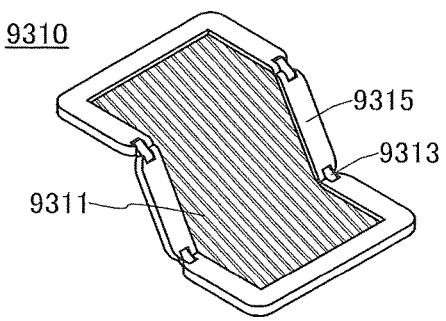
Figure 6C:
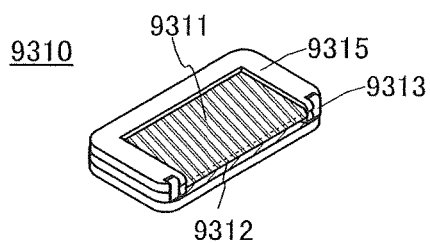

Another electronic device including a light-emitting device is a foldable portable information terminal illustrated in FIGS. 6A to 6C. FIG. 6A illustrates the portable information terminal 9310 which is opened. FIG. 6B illustrates the portable information terminal 9310 which is being opened or being folded. FIG. 6C illustrates the portable information terminal 9310 that is folded. The portable information terminal 9310 is highly portable when folded. The portable information terminal 9310 is highly browsable when opened because of a seamless large display region.

A display portion 9311 is supported by three housings 9315 joined together by hinges 9313. Note that the display portion 9311 may be a touch panel (an input/output device) including a touch sensor (an input device). By bending the display portion 9311 at a connection portion between two housings 9315 with the use of the hinges 9313, the portable information terminal 9310 can be reversibly changed in shape from an opened state to a folded state. A light-emitting device of one embodiment of the present invention can be used for the display portion 9311. A display region 9312 in the display portion 9311 is a display region that is positioned at a side surface of the portable information terminal 9310 that is folded. On the display region 9312, information icons, file shortcuts of frequently used applications or programs, and the like can be displayed, and confirmation of information and start of application can be smoothly performed.

Figure 7A:
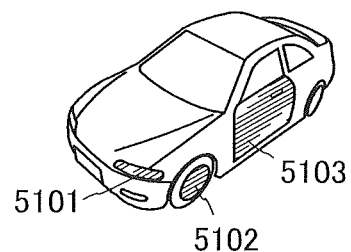
FIGS. 7A and 7B illustrate an automobile.
Figure 7B:
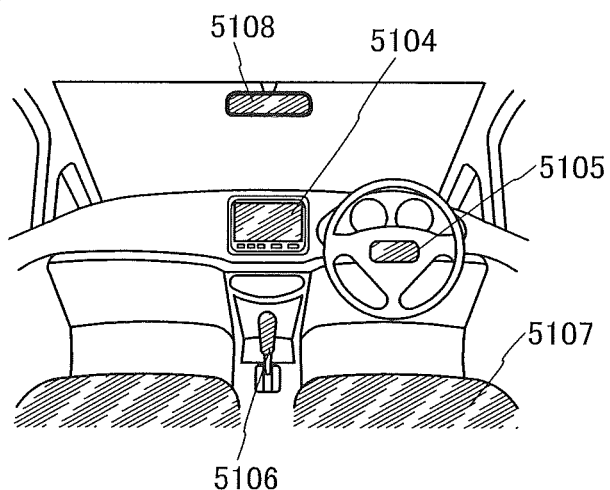

FIGS. 7A and 7B illustrate an automobile including a light-emitting device. The light-emitting device can be incorporated in the automobile, and specifically, can be included in lights 5101 (including lights of the rear part of the car), a wheel 5102 of a tire, a part or whole of a door 5103, or the like on the outer side of the automobile which is illustrated in FIG. 7A. The light-emitting device can also be included in a display portion 5104, a steering wheel 5105, a gear lever 5106, a sheet 5107, a rearview mirror 5108, or the like on the inner side of the automobile which is illustrated in FIG. 7B, or in a part of a glass window.

As described above, the electronic devices and automobiles can be obtained using the light-emitting device which is one embodiment of the present invention. Note that the light-emitting device can be used for electronic devices and automobiles in a variety of fields without being limited to the electronic devices described in this embodiment.

The structure described in this embodiment can be used in appropriate combination with any of the structures described in the other embodiments.

Embodiment 6

In this embodiment, a structure of a lighting device fabricated using the light-emitting element which is one embodiment of the present invention is described with reference to FIGS. 8A to 8D.

Figure 8A:
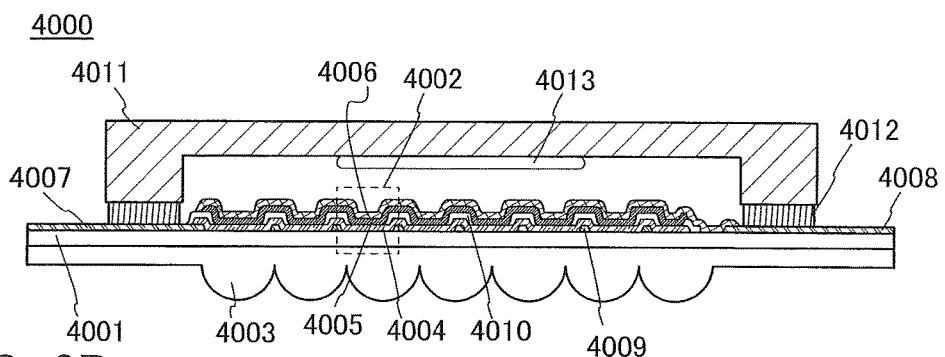
FIGS. 8A to 8D illustrate lighting devices.
Figure 8B:
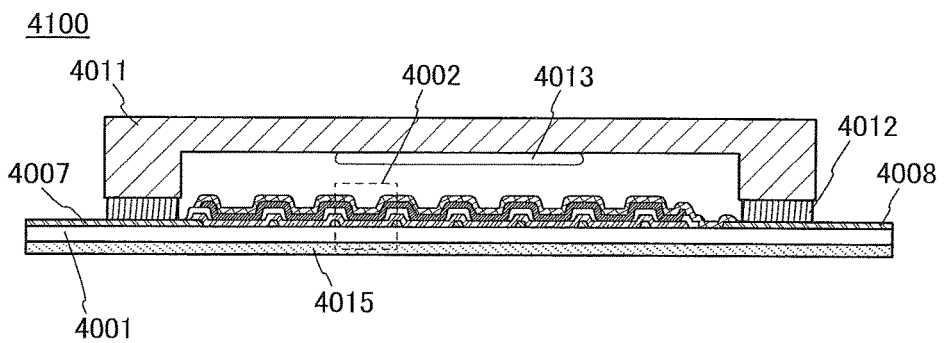
Figure 8C:
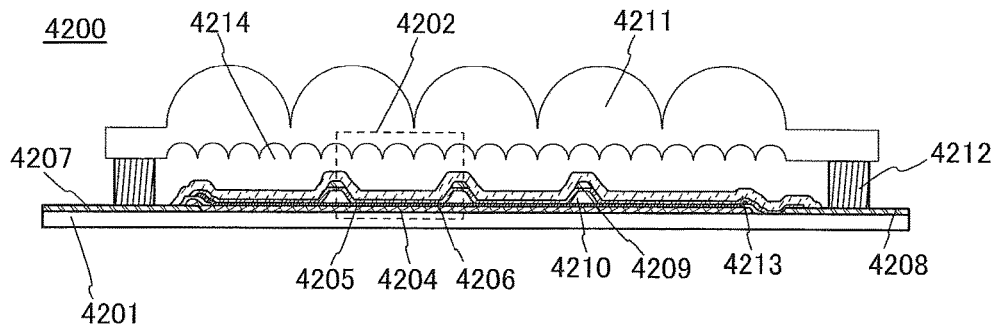
Figure 8D:
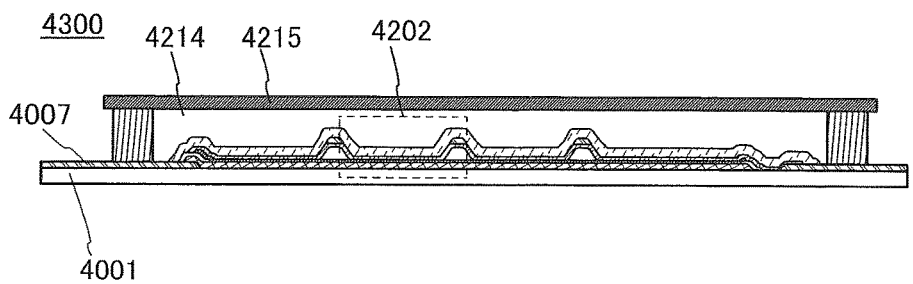

FIGS. 8A to 8D are examples of cross-sectional views of lighting devices. FIGS. 8A and 8B illustrate bottom-emission lighting devices in which light is extracted from the substrate side, and FIGS. 8C and 8D illustrate top-emission lighting devices in which light is extracted from the sealing substrate side.

A lighting device 4000 illustrated in FIG. 8A includes a light-emitting element 4002 over a substrate 4001. In addition, the lighting device 4000 includes a substrate 4003 with unevenness on the outside of the substrate 4001. The light-emitting element 4002 includes a first electrode 4004, an EL layer 4005, and a second electrode 4006.

The first electrode 4004 is electrically connected to an electrode 4007, and the second electrode 4006 is electrically connected to an electrode 4008. In addition, an auxiliary wiring 4009 electrically connected to the first electrode 4004 may be provided. Note that an insulating layer 4010 is formed over the auxiliary wiring 4009.

The substrate 4001 and a sealing substrate 4011 are bonded to each other by a sealant 4012. A desiccant 4013 is preferably provided between the sealing substrate 4011 and the light-emitting element 4002. The substrate 4003 has the unevenness illustrated in FIG. 8A, whereby the extraction efficiency of light emitted from the light-emitting element 4002 can be increased.

Instead of the substrate 4003, a diffusion plate 4015 may be provided on the outside of a substrate 4001 as in a lighting device 4100 illustrated in FIG. 8B.

A lighting device 4200 illustrated in FIG. 8C includes a light-emitting element 4202 over a substrate 4201. The light-emitting element 4202 includes a first electrode 4204, an EL layer 4205, and a second electrode 4206.

The first electrode 4204 is electrically connected to an electrode 4207, and the second electrode 4206 is electrically connected to an electrode 4208. An auxiliary wiring 4209 electrically connected to the second electrode 4206 may be provided. An insulating layer 4210 may be provided under the auxiliary wiring 4209.

The substrate 4201 and a sealing substrate 4211 with unevenness are bonded to each other by a sealant 4212. A barrier film 4213 and a planarization film 4214 may be provided between the sealing substrate 4211 and the light-emitting element 4202. The sealing substrate 4211 has the unevenness illustrated in FIG. 8C, whereby the extraction efficiency of light emitted from the light-emitting element 4202 can be increased.

Instead of the sealing substrate 4211, a diffusion plate 4215 may be provided over the light-emitting element 4202 as in a lighting device 4300 illustrated in FIG. 8D.

Note that the EL layers 4005 and 4205 in this embodiment can include the organometallic complex which is one embodiment of the present invention. In that case, a lighting device with low power consumption can be provided.

The structure described in this embodiment can be used in appropriate combination with any of the structures described in the other embodiments.

Embodiment 7

In this embodiment, examples of a lighting device which is an application of the light-emitting device of one embodiment of the present invention are described with reference to FIG. 9.

Figure 9:
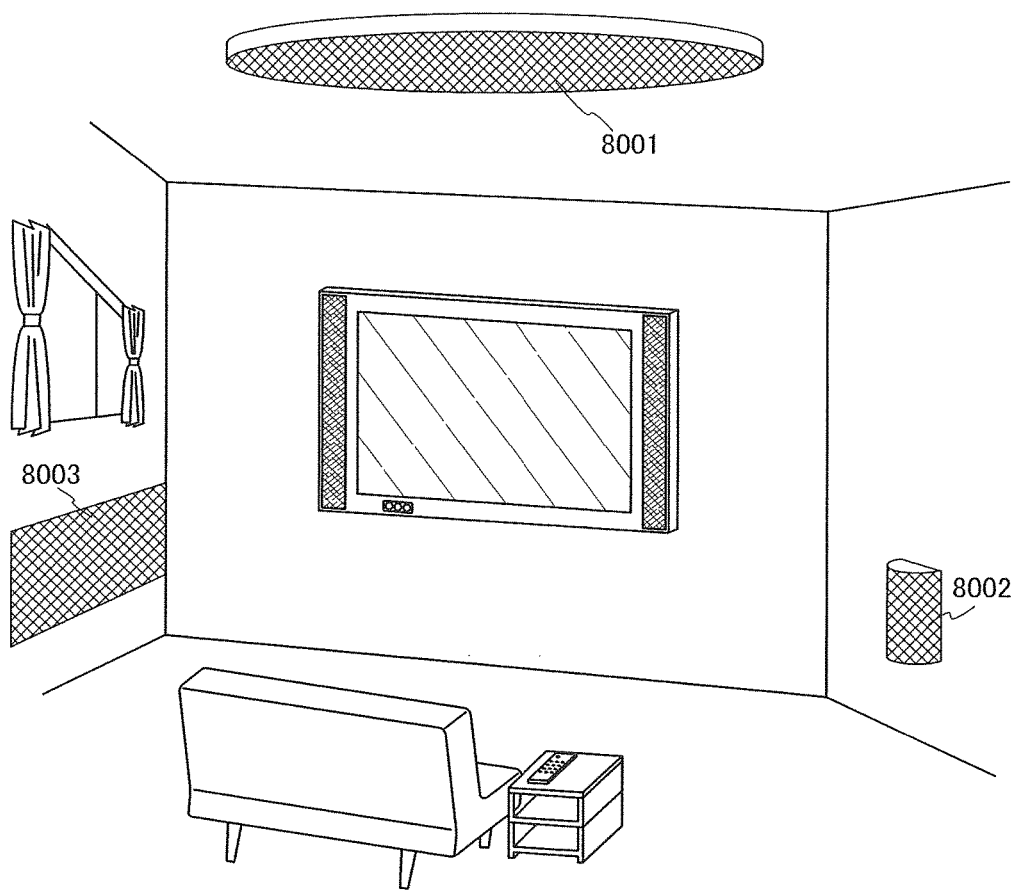
FIG. 9 illustrates lighting devices.

FIG. 9 illustrates an example in which the light-emitting device is used in an indoor lighting device 8001. Since the light-emitting device can have a large area, it can be used for a lighting device having a large area. In addition, with the use of a housing with a curved surface, a lighting device 8002 in which a light-emitting region has a curved surface can also be obtained. A light-emitting element included in the light-emitting device described in this embodiment is in a thin film form, which allows the housing to be designed more freely. Thus, the lighting device can be elaborately designed in a variety of ways. In addition, a wall of the room may be provided with a lighting device 8003.

Besides the above examples, when the light-emitting device is used as part of furniture in a room, a lighting device that functions as the furniture can be obtained.

As described above, a variety of lighting devices that include the light-emitting device can be obtained. Note that these lighting devices are also embodiments of the present invention.

The structure described in this embodiment can be used in appropriate combination with any of the structures described in the other embodiments.

Embodiment 8

In this embodiment, touch panels including a light-emitting element of one embodiment of the present invention or a light-emitting device of one embodiment of the present invention are described with reference to FIGS. 10A and 10B, FIGS. 11A and 11B, FIGS. 12A and 12B, FIGS. 13A and 13B, and FIG. 14.

Figure 10A:
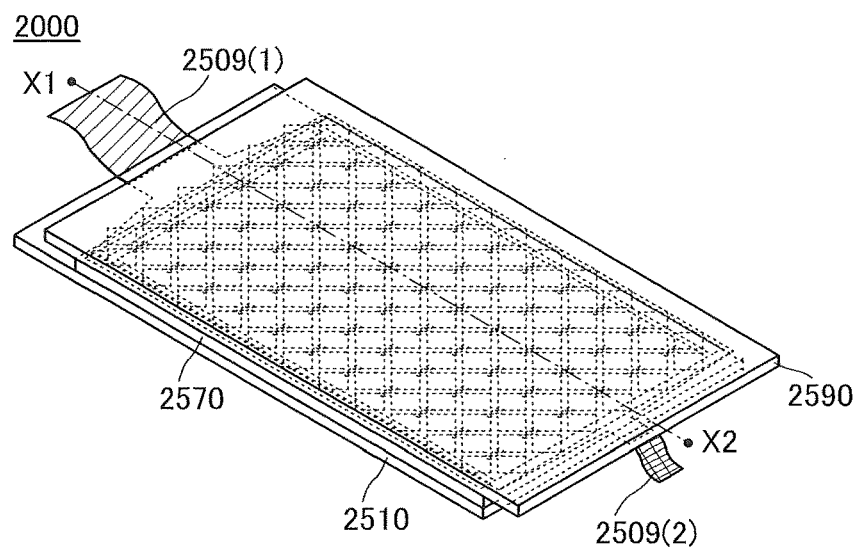
FIGS. 10A and 10B illustrate an example of a touch panel.
Figure 10B:
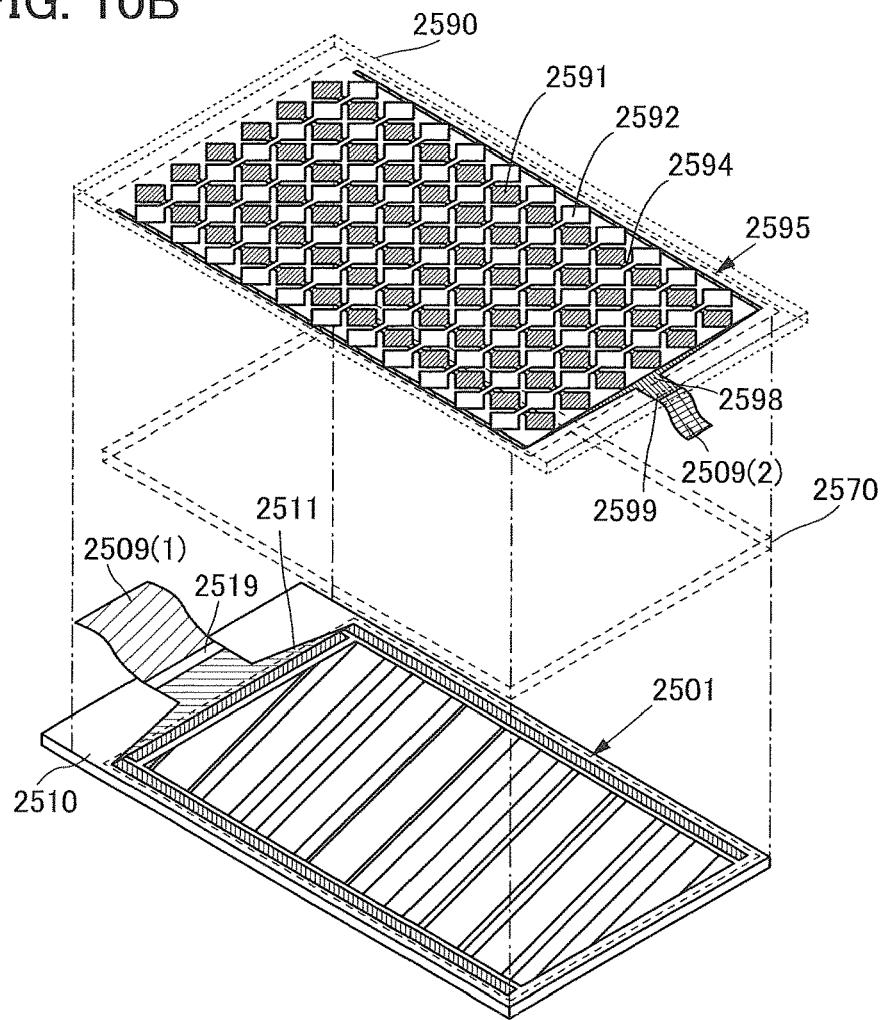

FIGS. 10A and 10B are perspective views of a touch panel 2000. Note that FIGS. 10A and 10B illustrate typical components of the touch panel 2000 for simplicity.

The touch panel 2000 includes a display panel 2501 and a touch sensor 2595 (see FIG. 10B). Furthermore, the touch panel 2000 includes a substrate 2510, a substrate 2570, and a substrate 2590.

The display panel 2501 includes a plurality of pixels over the substrate 2510, and a plurality of wirings 2511 through which signals are supplied to the pixels. The plurality of wirings 2511 are led to a peripheral portion of the substrate 2510, and part of the plurality of wirings 2511 forms a terminal 2519. The terminal 2519 is electrically connected to an FPC 2509(1).

The substrate 2590 includes the touch sensor 2595 and a plurality of wirings 2598 electrically connected to the touch sensor 2595. The plurality of wirings 2598 are led to a peripheral portion of the substrate 2590, and part of the plurality of wirings 2598 forms a terminal 2599. The terminal 2599 is electrically connected to an FPC 2509(2). Note that in FIG. 10B, electrodes, wirings, and the like of the touch sensor 2595 provided on the back side of the substrate 2590 (the side facing the substrate 2510) are indicated by solid lines for clarity.

As the touch sensor 2595, a capacitive touch sensor can be used, for example. Examples of the capacitive touch sensor are a surface capacitive touch sensor, a projected capacitive touch sensor, and the like.

Examples of the projected capacitive touch sensor are a self-capacitive touch sensor, a mutual capacitive touch sensor, and the like, which differ mainly in the driving method. The use of a mutual capacitive touch sensor is preferable because multiple points can be sensed simultaneously.

First, an example of using a projected capacitive touch sensor is described with reference to FIG. 10B. Note that in the case of a projected capacitive touch sensor, a variety of sensors that can sense the closeness or the contact of a sensing target such as a finger can be used.

The projected capacitive touch sensor 2595 includes electrodes 2591 and electrodes 2592. The electrodes 2591 are electrically connected to any of the plurality of wirings 2598, and the electrodes 2592 are electrically connected to any of the other wirings 2598. The electrodes 2592 each have a shape of a plurality of quadrangles arranged in one direction with one corner of a quadrangle connected to one corner of another quadrangle with a wiring 2594 in one direction, as illustrated in FIGS. 10A and 10B. In the same manner, the electrodes 2591 each have a shape of a plurality of quadrangles arranged with one corner of a quadrangle connected to one corner of another quadrangle; however, the direction in which the electrodes 2591 are connected is a direction crossing the direction in which the electrodes 2592 are connected. Note that the direction in which the electrodes 2591 are connected and the direction in which the electrodes 2592 are connected are not necessarily perpendicular to each other, and the electrodes 2591 may be arranged to intersect with the electrodes 2592 at an angle greater than 0° and less than 90°.

The intersecting area of the wiring 2594 and one of the electrodes 2592 is preferably as small as possible. Such a structure allows a reduction in the area of a region where the electrodes are not provided, reducing unevenness in transmittance. As a result, unevenness in the luminance of light from the touch sensor 2595 can be reduced.

Note that the shapes of the electrodes 2591 and the electrodes 2592 are not limited to the above-mentioned shapes and can be any of a variety of shapes. For example, the plurality of electrodes 2591 may be provided so that a space between the electrodes 2591 are reduced as much as possible, and the plurality of electrodes 2592 may be provided with an insulating layer sandwiched between the electrodes 2591 and the electrodes 2592. In that case, between two adjacent electrodes 2592, a dummy electrode which is electrically insulated from these electrodes is preferably provided, whereby the area of a region having a different transmittance can be reduced.

Figure 11A:
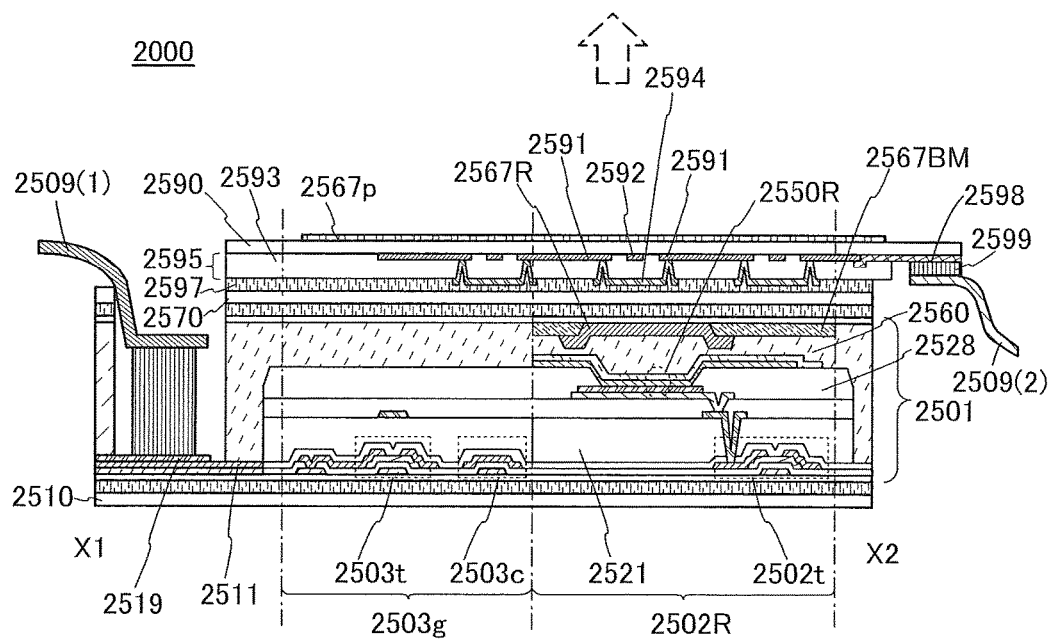
FIGS. 11A and 11B illustrate an example of a touch panel.
Figure 11B:
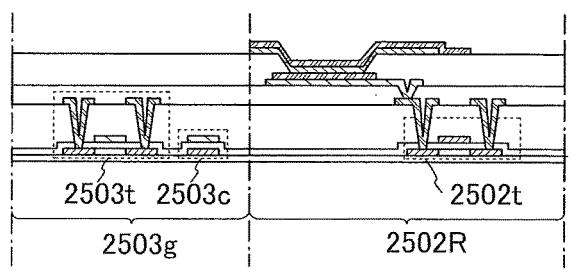

Next, the touch panel 2000 is described in detail with reference to FIGS. 11A and 11B. FIGS. 11A and 11B are cross-sectional views taken along the dashed-dotted line X1-X2 in FIG. 10A.

The touch panel 2000 includes the touch sensor 2595 and the display panel 2501.

The touch sensor 2595 includes the electrodes 2591 and the electrodes 2592 that are provided in a staggered arrangement and in contact with the substrate 2590, an insulating layer 2593 covering the electrodes 2591 and the electrodes 2592, and the wiring 2594 that electrically connects the adjacent electrodes 2591 to each other. Between the adjacent electrodes 2591, the electrode 2592 is provided.

The electrodes 2591 and the electrodes 2592 can be formed using a light-transmitting conductive material. As a light-transmitting conductive material, a conductive oxide such as indium oxide, indium tin oxide, indium zinc oxide, zinc oxide, or zinc oxide to which gallium is added can be used. A graphene compound may be used as well. When a graphene compound is used, it can be formed, for example, by reducing a graphene oxide film. As a reducing method, a method with application of heat, a method with laser irradiation, or the like can be employed.

For example, the electrodes 2591 and the electrodes 2592 can be formed by depositing a light-transmitting conductive material on the substrate 2590 by a sputtering method and then removing an unneeded portion by any of various patterning techniques such as photolithography.

Examples of a material for the insulating layer 2593 are a resin such as acrylic or epoxy resin, a resin having a siloxane bond, and an inorganic insulating material such as silicon oxide, silicon oxynitride, or aluminum oxide.

The adjacent electrodes 2591 are electrically connected to each other with a wiring 2594 formed in part of the insulating layer 2593. Note that a material for the wiring 2594 preferably has higher conductivity than materials for the electrode 2591 and the electrode 2592 to reduce electrical resistance.

One wiring 2598 is electrically connected to any of the electrodes 2591 and 2592. Part of the wiring 2598 serves as a terminal. For the wiring 2598, a metal material such as aluminum, gold, platinum, silver, nickel, titanium, tungsten, chromium, molybdenum, iron, cobalt, copper, or palladium or an alloy material containing any of these metal materials can be used.

Through the terminal 2599, the wiring 2598 and the FPC 2509(2) are electrically connected to each other. The terminal 2599 can be formed using any of various kinds of anisotropic conductive films (ACF), anisotropic conductive pastes (ACP), and the like.

An adhesive layer 2597 is provided in contact with the wiring 2594. That is, the touch sensor 2595 is attached to the display panel 2501 so that they overlap with each other with the adhesive layer 2597 provided therebetween. Note that the substrate 2570 as shown in FIG. 11A may be provided over the surface of the display panel 2501 that is adjacent to the adhesive layer 2597; however, the substrate 2570 is not always needed.

The adhesive layer 2597 has a light-transmitting property. For example, a thermosetting resin or an ultraviolet curable resin can be used; specifically, a resin such as an acrylic-based resin, a urethane-based resin, an epoxy-based resin, or a siloxane-based resin can be used.

The display panel 2501 in FIG. 11A includes, between the substrate 2510 and the substrate 2570, a plurality of pixels arranged in a matrix and a driver circuit. Each pixel includes a light-emitting element and a pixel circuit driving the light-emitting element.

In FIG. 11A, a pixel 2502R is shown as an example of the pixel of the display panel 2501, and a scan line driver circuit 2503g is shown as an example of the driver circuit.

The pixel 2502R includes a light-emitting element 2550R and a transistor 2502t that can supply electric power to the light-emitting element 2550R.

The transistor 2502t is covered with an insulating layer 2521. The insulating layer 2521 covers unevenness caused by the transistor and the like that have been already formed to provide a flat surface. The insulating layer 2521 may serve also as a layer for preventing diffusion of impurities. That is preferable because a reduction in the reliability of the transistor or the like due to diffusion of impurities can be prevented.

The light-emitting element 2550R is electrically connected to the transistor 2502t through a wiring. It is one electrode of the light-emitting element 2550R that is directly connected to the wiring. An end portion of the one electrode of the light-emitting element 2550R is covered with an insulator 2528.

The light-emitting element 2550R includes an EL layer between a pair of electrodes. A coloring layer 2567R is provided to overlap with the light-emitting element 2550R, and part of light emitted from the light-emitting element 2550R is transmitted through the coloring layer 2567R and extracted in the direction indicated by an arrow in the drawing. A light-blocking layer 2567BM is provided at an end portion of the coloring layer, and a sealing layer 2560 is provided between the light-emitting element 2550R and the coloring layer 2567R.

Note that when the sealing layer 2560 is provided on the side from which light from the light-emitting element 2550R is extracted, the sealing layer 2560 preferably has a light-transmitting property. The sealing layer 2560 preferably has a higher refractive index than the air.

A scan line driver circuit 2503g includes a transistor 2503t and a capacitor 2503c. Note that the driver circuit and the pixel circuits can be formed in the same process over the same substrate. Thus, in a similar manner to that of the transistor 2502t in the pixel circuit, the transistor 2503t in the driver circuit (scan line driver circuit 2503g) is also covered with the insulating layer 2521.

The wirings 2511 through which a signal can be supplied to the transistor 2503t are provided. The terminal 2519 is provided in contact with the wiring 2511. The terminal 2519 is electrically connected to the FPC 2509(1), and the FPC 2509(1) has a function of supplying signals such as an image signal and a synchronization signal. Note that a printed wiring board (PWB) may be attached to the FPC 2509(1).

Although the case where the display panel 2501 shown in FIG. 11A includes a bottom-gate transistor is described, the structure of the transistor is not limited thereto, and any of transistors with various structures can be used. In each of the transistor 2502t and the transistor 2503t illustrated in FIG. 11A, a semiconductor layer including an oxide semiconductor can be used for a channel region. Alternatively, a semiconductor layer containing amorphous silicon or a semiconductor layer containing polycrystalline silicon that is obtained by crystallization process such as laser annealing can be used for a channel region.

FIG. 11B illustrates the structure of the display panel 2501 that includes a top-gate transistor instead of the bottom-gate transistor illustrated in FIG. 11A. The kind of the semiconductor layer that can be used for the channel region does not depend on the structure of the transistor.

In the touch panel 2000 shown in FIG. 11A, an anti-reflection layer 2567p overlapping with at least the pixel is preferably provided on a surface of the touch panel on the side from which light from the pixel is extracted, as shown in FIG. 11A. As the anti-reflection layer 2567p, a circular polarizing plate or the like can be used.

For the substrate 2510, the substrate 2570, and the substrate 2590 in FIG. 11A, for example, a flexible material having a vapor permeability of $1 \times 10^{-5}$ g/(m$^2$·day) or lower, preferably $1 \times 10^{-6}$ g/(m$^2$·day) or lower can be favorably used. Alternatively, it is preferable to use the materials that make these substrates have substantially the same coefficient of thermal expansion. For example, the coefficients of linear expansion of the materials are $1 \times 10^{-3}$/K or lower, preferably $5 \times 10^{-5}$/K or lower, and further preferably $1 \times 10^{-5}$/K or lower.

Next, a touch panel 2000' having a structure different from that of the touch panel 2000 shown in FIGS. 11A and 11B is described with reference to FIGS. 12A and 12B. Note that the touch panel 2000' can be used for an application similar to that of the touch panel 2000.

Figure 12A:
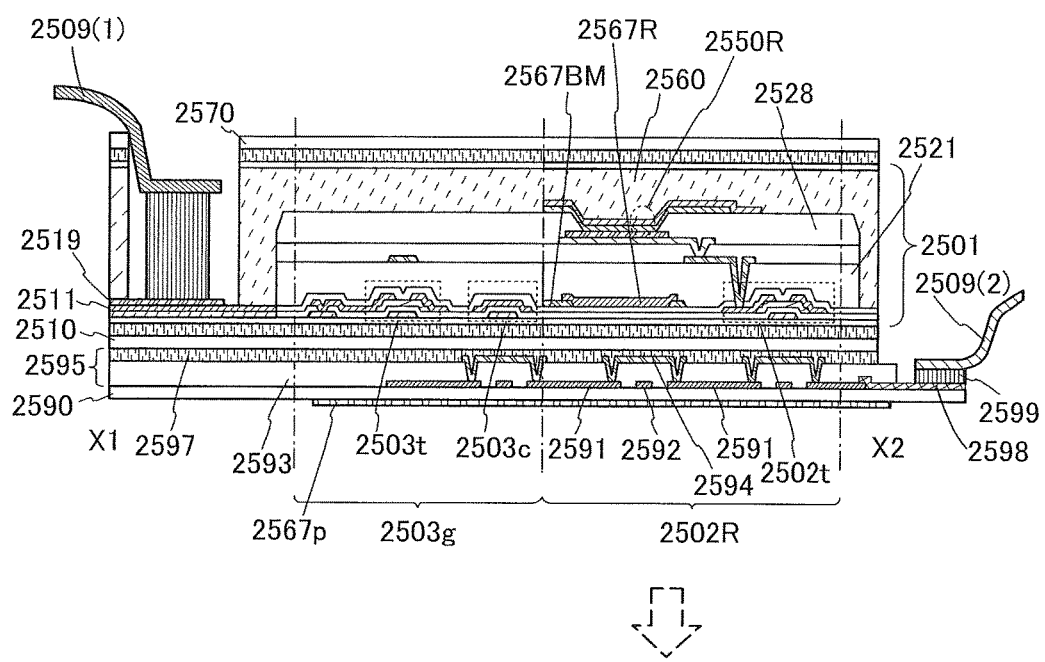
FIGS. 12A and 12B illustrate an example of a touch panel.
Figure 12B:
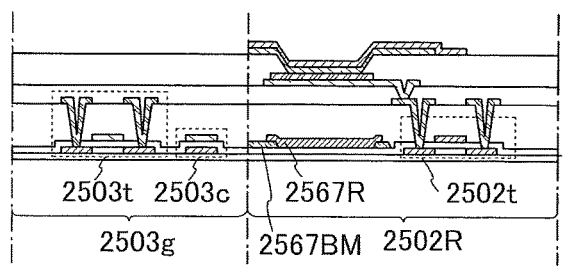

FIGS. 12A and 12B are cross-sectional views of the touch panel 2000'. In the touch panel 2000' illustrated in FIGS. 12A and 12B, the position of the touch sensor 2595 relative to the display panel 2501 is different from that in the touch panel 2000 illustrated in FIGS. 11A and 11B. Only different structures are described below, and the above description of the touch panel 2000 can be referred to for the other similar structures.

The coloring layer 2567R overlaps with the light-emitting element 2550R. Light from the light-emitting element 2550R illustrated in FIG. 12A is emitted to the side where the transistor 2502t is provided. That is, (part of) light emitted from the light-emitting element 2550R passes through the coloring layer 2567R and is extracted in the direction indicated by an arrow in FIG. 12A. Note that the light-blocking layer 2567BM is provided at an end portion of the coloring layer 2567R.

The touch sensor 2595 is provided on the transistor 2502t side (the far side from the light-emitting element 2550R) of the display panel 2501 (see FIG. 12A). The adhesive layer 2597 is in contact with the substrate 2510 of the display panel 2501 and attaches the display panel 2501 and the touch sensor 2595 to each other in the structure shown in FIG. 12A. The substrate 2510 is not necessarily provided between the display panel 2501 and the touch sensor 2595 that are attached to each other by the adhesive layer 2597.

As in the touch panel 2000, transistors with a variety of structures can be used for the display panel 2501 in the touch panel 2000'. Although a bottom-gate transistor is used in FIG. 12A, a top-gate transistor may be used as shown in FIG. 12B.

An example of a driving method of the touch panel is described with reference to FIGS. 13A and 13B.

Figure 13A:
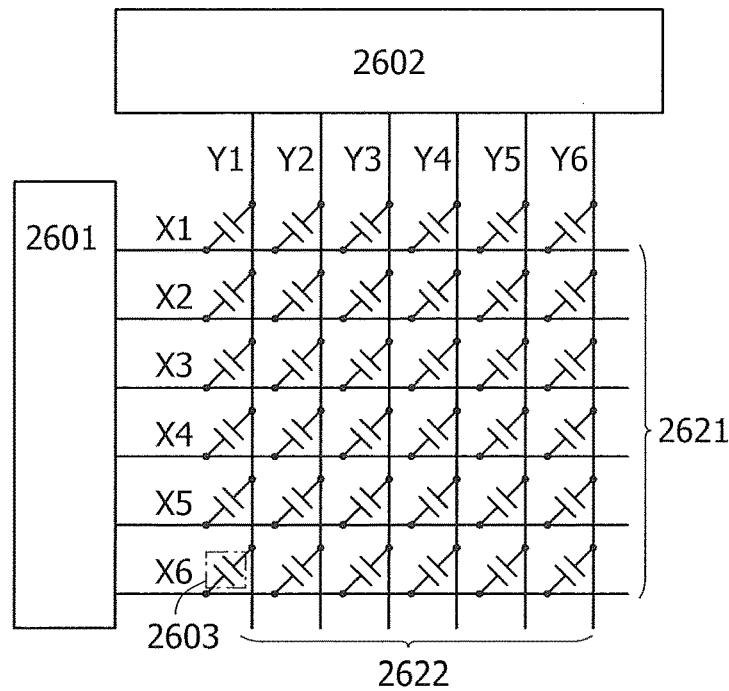
FIGS. 13A and 13B are a block diagram and a timing chart of a touch sensor.

FIG. 13A is a block diagram illustrating the structure of a mutual capacitive touch sensor. FIG. 13A illustrates a pulse voltage output circuit 2601 and a current sensing circuit 2602. Note that in the example of FIG. 13A, six wirings X1-X6 represent electrodes 2621 to which a pulse voltage is supplied, and six wirings Y1-Y6 represent electrodes 2622 that sense a change in current. FIG. 13A also illustrates a capacitor 2603 which is formed in a region where the electrodes 2621 and 2622 overlap with each other. Note that functional replacement between the electrodes 2621 and 2622 is possible.

The pulse voltage output circuit 2601 is a circuit for sequentially applying a pulse voltage to the wirings X1 to X6. By application of a pulse voltage to the wirings X1 to X6, an electric field is generated between the electrodes 2621 and 2622 of the capacitor 2603. When the electric field between the electrodes is shielded, for example, a change occurs in the capacitor 2603 (mutual capacitance). The approach or contact of a sensing target can be sensed by utilizing this change.

The current sensing circuit 2602 is a circuit for sensing changes in current flowing through the wirings Y1 to Y6 that are caused by the change in mutual capacitance in the capacitor 2603. No change in current value is sensed in the wirings Y1 to Y6 when there is no approach or contact of a sensing target, whereas a decrease in current value is sensed when mutual capacitance is decreased owing to the approach or contact of a sensing target. Note that an integrator circuit or the like is used for sensing of current.

Figure 13B:
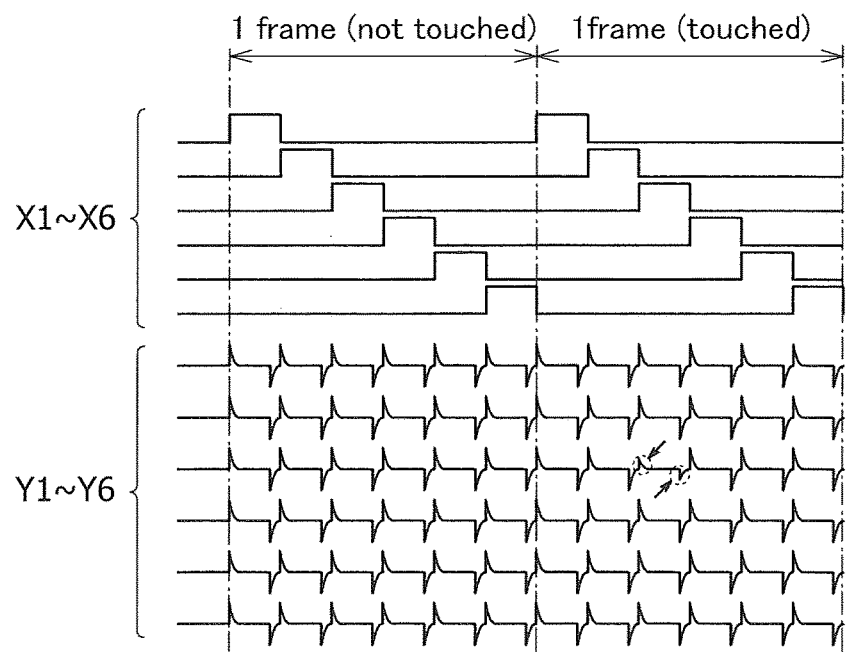

FIG. 13B is a timing chart showing input and output waveforms in the mutual capacitive touch sensor illustrated in FIG. 13A. In FIG. 13B, sensing of a sensing target is performed in all the rows and columns in one frame period. FIG. 13B shows a period when a sensing target is not sensed (not touched) and a period when a sensing target is sensed (touched). Sensed current values of the wirings Y1 to Y6 are shown as the waveforms of voltage values.

A pulse voltage is sequentially applied to the wirings X1 to X6, and the waveforms of the wirings Y1 to Y6 change in accordance with the pulse voltage. When there is no approach or contact of a sensing target, the waveforms of the wirings Y1 to Y6 change in accordance with changes in the voltages of the wirings X1 to X6. The current value is decreased at the point of approach or contact of a sensing target and accordingly the waveform of the voltage value changes. By sensing a change in mutual capacitance in this manner, the approach or contact of a sensing target can be sensed.

Figure 14:
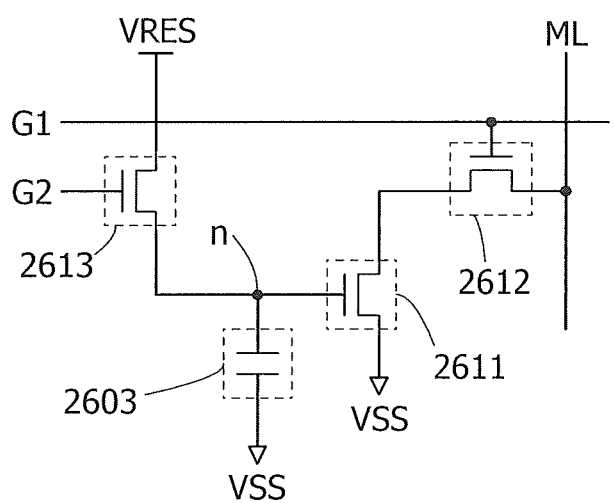
FIG. 14 is a circuit diagram of a touch sensor.

Although FIG. 13A illustrates a passive touch sensor in which only the capacitor 2603 is provided at the intersection of wirings as a touch sensor, an active touch sensor including a transistor and a capacitor may be used. FIG. 14 is a sensor circuit included in an active touch sensor.

The sensor circuit illustrated in FIG. 14 includes the capacitor 2603, a transistor 2611, a transistor 2612, and a transistor 2613.

A signal G2 is input to a gate of the transistor 2613. A voltage VRES is applied to one of a source and a drain of the transistor 2613, and one electrode of the capacitor 2603 and a gate of the transistor 2611 are electrically connected to the other of the source and the drain of the transistor 2613. One of a source and a drain of the transistor 2611 is electrically connected to one of a source and a drain of the transistor 2612, and a voltage VSS is applied to the other of the source and the drain of the transistor 2611. A signal G1 is input to a gate of the transistor 2612, and a wiring ML is electrically connected to the other of the source and the drain of the transistor 2612. The voltage VSS is applied to the other electrode of the capacitor 2603.

Next, the operation of the sensor circuit illustrated in FIG. 14 is described. First, a potential for turning on the transistor 2613 is supplied as the signal G2, and a potential with respect to the voltage VRES is thus applied to the node n connected to the gate of the transistor 2611. Then, a potential for turning off the transistor 2613 is applied as the signal G2, whereby the potential of the node n is maintained. Then, mutual capacitance of the capacitor 2603 changes owing to the approach or contact of a sensing target such as a finger, and accordingly the potential of the node n is changed from VRES.

In reading operation, a potential for turning on the transistor 2612 is supplied as the signal G1. A current flowing through the transistor 2611, that is, a current flowing through the wiring ML is changed in accordance with the potential of the node n. By sensing this current, the approach or contact of a sensing target can be sensed.

In each of the transistors 2611, 2612, and 2613, an oxide semiconductor layer is preferably used as a semiconductor layer in which a channel region is formed. Such a transistor is preferably used as the transistor 2613, in particular, so that the potential of the node n can be held for a long time and the frequency of operation of resupplying VRES to the node n (refresh operation) can be reduced.

At least part of this embodiment can be implemented in combination with any of the other embodiments described in this specification as appropriate.

EXAMPLE 1

Synthesis Example 1

In this example, a method of synthesizing 9,9'-[pyrimidine-4,6-diyl bis(biphenyl-3,3'-diyl)]bis(9H-carbazole) (abbreviation: 4,6mCzBP2Pm) (the structural formula (100)), which is a heterocyclic compound of one embodiment of the present invention, is described. The structure of 4,6mCzBP2Pm is shown below.

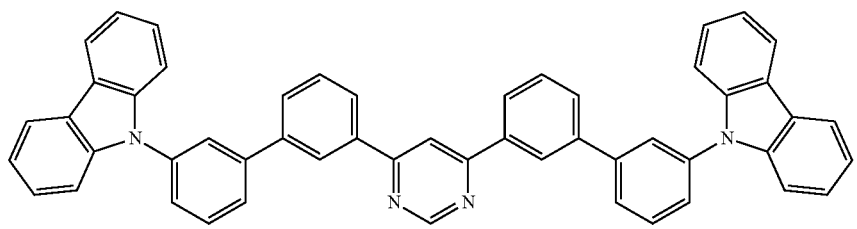

(100)

Synthesis of 4,6mCzBP2Pm

First, 0.54 g (2.3 mmol) of 2,4-dibromopyrimidine, 1.8 g (5.0 mmol) of 3-(3-(9H-carbazol-9-yl)phenyl)phenyl boronic acid, and 69 mg (0.23 mmol) of tris(2-methylphenyl)phosphine were put into a 50-mL three-neck flask, and the air in the flask was replaced with nitrogen.

Then, 4.9 mL of a 2M potassium carbonate aqueous solution, 12 mL of toluene, and 4 mL of ethanol were added to this mixture, and the mixture was degassed by being stirred under reduced pressure. To this mixture, 10 mg (0.045 mmol) of palladium(II) acetate was added and stirring was performed under a nitrogen stream at 90° C. for 16 hours. After the stirring, water was added to the mixture, and an aqueous layer was subjected to extraction with toluene.

The obtained solution of the extract and an organic layer were combined, and the mixture was washed with water and saturated brine. Then, the mixture was dried with magnesium sulfate. This mixture was separated by gravity filtration, and the filtrate was concentrated to give an oily substance. The oily substance was purified by silica gel column chromatography (as the developing solvent, first hexane and toluene in a ratio of 5:1 were used, and then chloroform and ethyl acetate in a ratio of 50:1 were used). The obtained fraction was concentrated to give an oily substance. Chloroform was added to this oily substance, the mixture was suction-filtered through Celite and alumina, and the filtrate was concentrated to give an oily substance. This oily substance was purified by high performance liquid column chromatography (HPLC) (developing solvent: chloroform).

The obtained fraction was concentrated to give an oily substance. This oily substance was recrystallized with toluene/hexane to give 1.0 g of a target white solid in a yield of 63%.

By a train sublimation method, 0.99 g of the obtained white solid was purified. In the purification by sublimation, the white solid was heated at 320° C. under the conditions where the pressure was 2.7 Pa and the argon flow rate was 5 mL/min. After the purification by sublimation, 0.91 g of a pale yellow solid was obtained at a collection rate of 92%. A synthesis scheme of the above synthesis method is shown in (A-1) below.

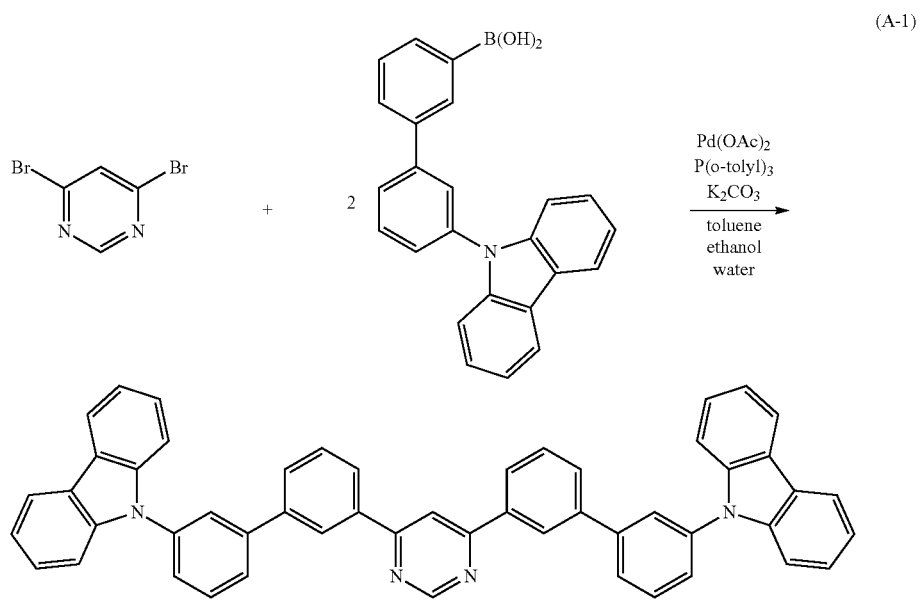

(A-1)

Figure 15A:
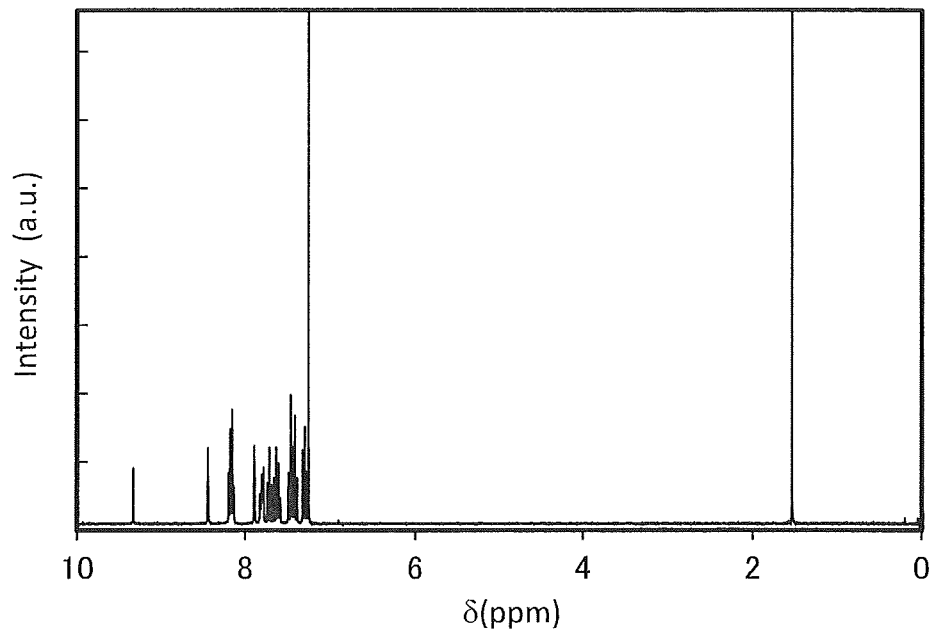
FIGS. 15A and 15B show a $^1$H-NMR chart of a heterocyclic compound represented by the structural formula (100)
Figure 15B:
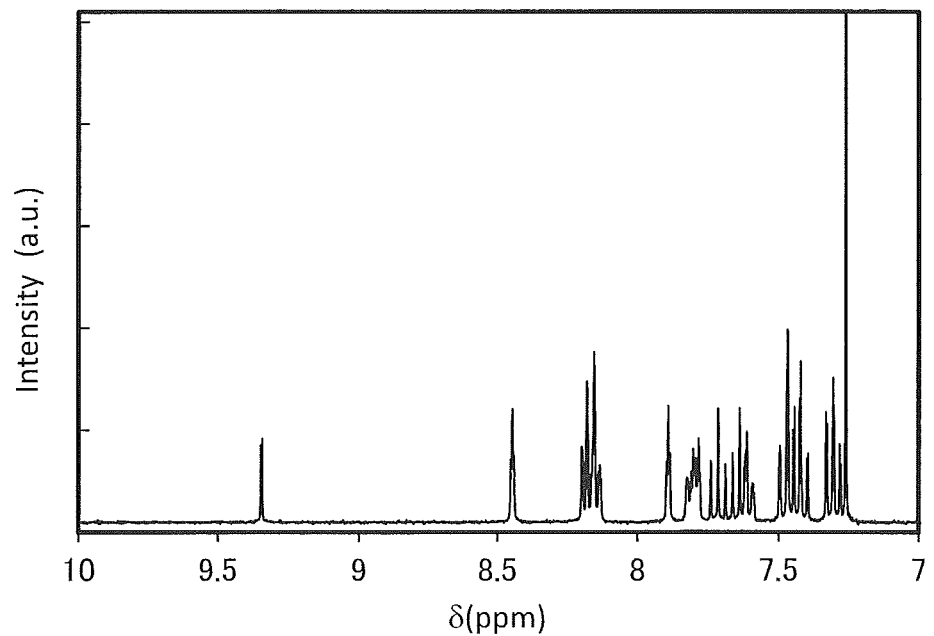

Analysis results by nuclear magnetic resonance ($^1$H-NMR) spectroscopy of the pale yellow solid obtained by the above-described synthesis method are described below. FIGS. 15A and 15B show the $^1$H-NMR chart. FIG. 15B is a chart where the range from 7 (ppm) to 10 (ppm) on the horizontal axis (δ) in FIG. 15A is enlarged. The results revealed that 4,6mCzBP2Pm (the structural formula (100)), which is a heterocyclic compound of one embodiment of the present invention, was obtained in this example.

$^1$H-NMR (CDCl$_3$, 300 MHz): δ=7.30 (td, J=7.2 Hz, 1.2 Hz, 4H), 7.39-7.50 (in, 8H), 7.59-7.66 (m, 4H), 7.72 (t,

J=7.8 Hz, 2H), 7.78-7.83 (m, 4H), 7.89 (s, 2H), 8.13-8.20 (in, 7H), 8.45 (s, 2H), 9.34 (sd, J=1.2 Hz, 1H).

Figure 16A:
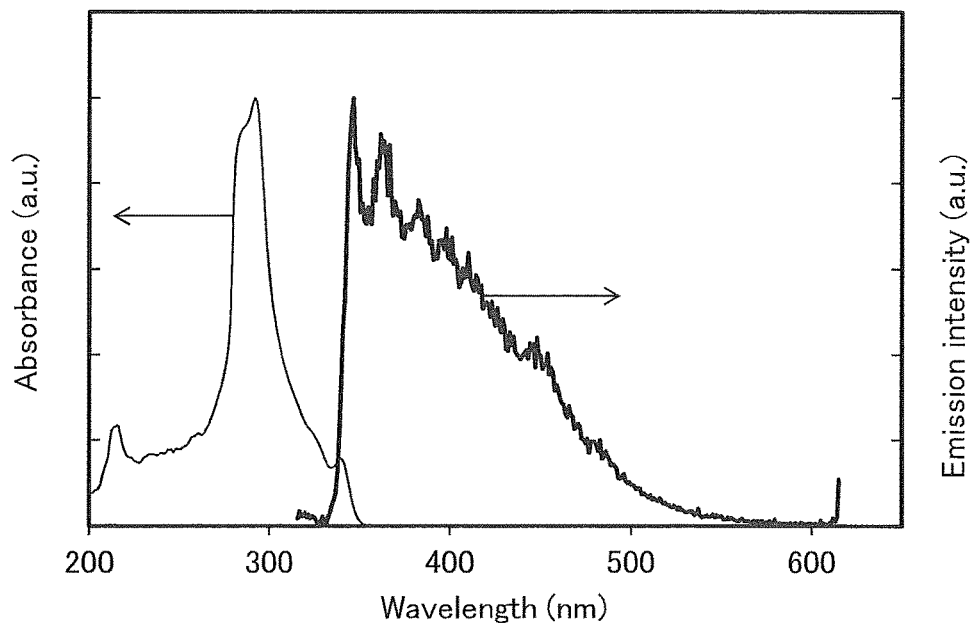
FIGS. 16A and 16B show ultraviolet-visible absorption spectra and emission spectra of the heterocyclic compound represented by the structural formula (100)
Figure 16B:
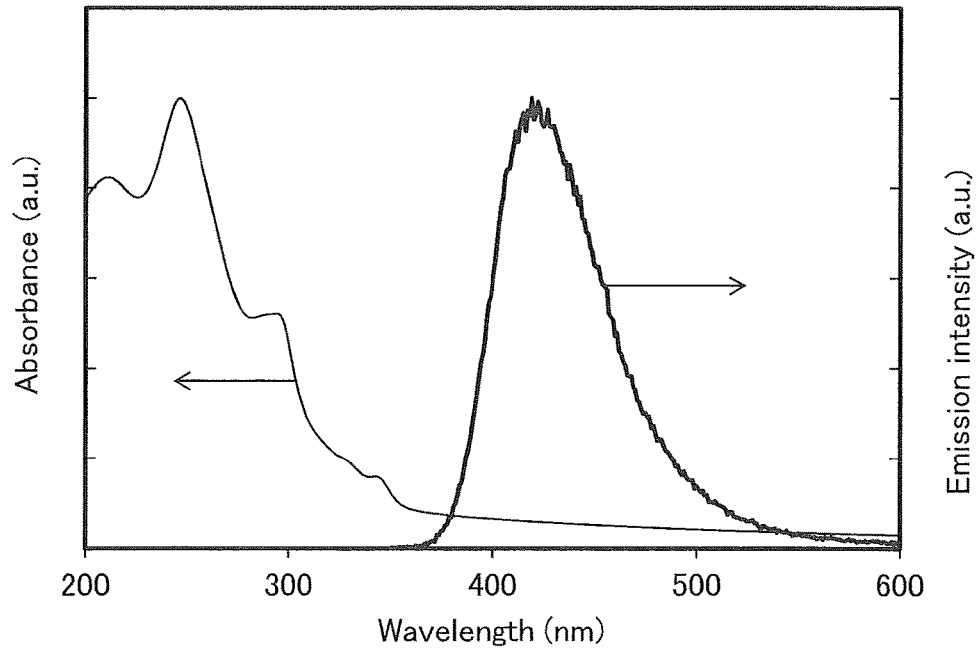

Next, ultraviolet-visible absorption spectra (hereinafter, simply referred to as "absorption spectra") and emission spectra of 4,6mCzBP2Pm in a toluene solution of 4,6mCzBP2Pm and a thin film of 4,6mCzBP2Pm were measured at room temperature. The spectra of the toluene solution of 4,6mCzBP2Pm were measured by putting the solution in a quartz cell. The spectra of the thin film were measured with a sample prepared by evaporation of 4,6mCzBP2Pm on a quartz substrate. The absorption spectra were measured with an ultraviolet-visible light spectrophotometer (V-550, manufactured by JASCO Corporation), and the emission spectra were measured with a fluorescence spectrophotometer (FS920, manufactured by Hamamatsu Photonics K.K.). FIG. 16A shows the obtained absorption and emission spectra of 4,6mCzBP2Pm in the toluene solution, and FIG. 16B shows the obtained absorption and emission spectra of the thin film. The horizontal axis represents wavelength and the vertical axes represent absorbance and emission intensity. The absorption spectrum shown in FIG. 16A was obtained by subtraction of the absorption spectra of toluene and the quartz cell from the obtained absorption spectrum. The absorption spectrum shown in FIG. 16B was obtained by subtraction of the absorption spectrum of the quartz substrate from the obtained absorption spectrum.

According to the above measurement, 4,6mCzBP2Pm, which is a heterocyclic compound of one embodiment of the present invention, in the toluene solution has absorption peaks at approximately 339 nm and 291 nm, and an emission peak at approximately 347 nm. In addition, the thin film of 4,6mCzBP2Pm has absorption peaks at approximately 342 nm, 293 nm, and 245 nm, and an emission peak at approximately 422 nm. Thus, it was found that absorption and emission of 4,6mCzBP2Pm occur in extremely short wavelength ranges. Therefore, 4,6mCzBP2Pm is favorable as a host material which is used in combination with a dopant that emits light in a short wavelength range.

Figure 17:
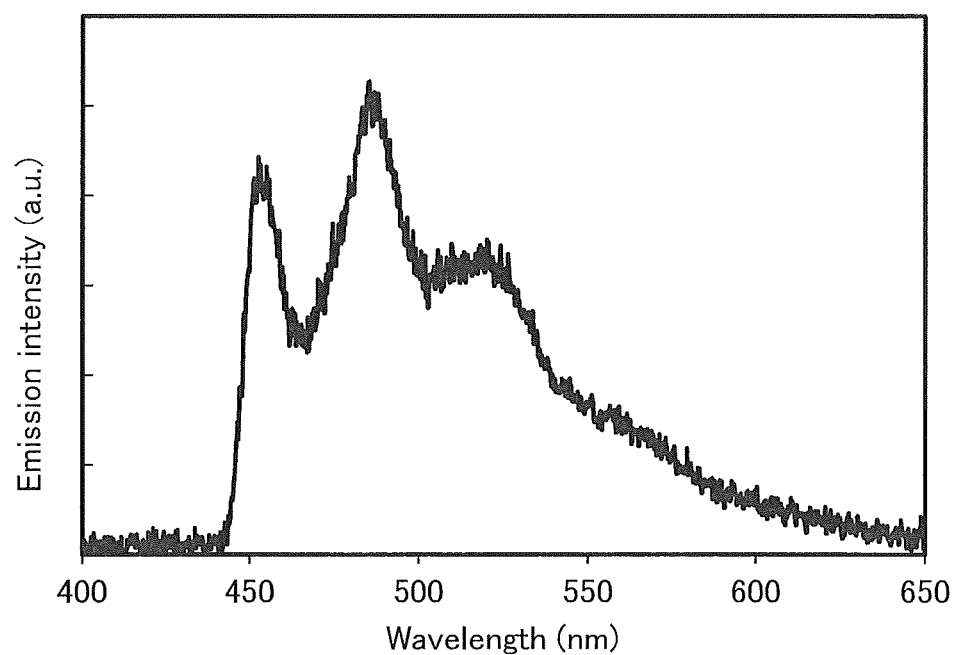
FIG. 17 shows a phosphorescence spectrum of the heterocyclic compound represented by the structural formula (100)

Phosphorescence of 4,6mCzBP2Pm was measured. The measurement was performed by using a PL microscope, LabRAM HR-PL, produced by HORIBA, Ltd., a He—Cd laser (325 nm) as excitation light, and a CCD detector at a measurement temperature of 10 K. For the measurement, a thin film as a sample was formed over a quartz substrate to a thickness of approximately 50 nm and another quartz substrate was attached to the deposition surface in a nitrogen atmosphere. The measurement results are shown in FIG. 17. The results showed that the peak on the shortest wavelength side of a phosphorescence spectrum of 4,6mCzBP2Pm is at approximately 452 nm, which means that 4,6mCzBP2Pm has a high T1 level.

Next, 4,6mCzBP2Pm was analyzed by liquid chromatography mass spectrometry (LC/MS). The analysis by LC/MS was carried out with Acquity UPLC (registered trademark, manufactured by Waters Corporation), and Xevo G2 Tof MS (manufactured by Waters Corporation).

In the MS analysis, ionization was carried out by an electrospray ionization (ESI) method. At this time, the capillary voltage and the sample cone voltage were set to 3.0 kV and 30 V, respectively, and detection was performed in a positive mode. A component that underwent the ionization under the above-described conditions was collided with an argon gas in a collision cell to dissociate into product ions. The energy (collision energy) for the collision with argon was 70 eV. The mass range for the measurement was m/z=100 to 1200.

Figure 18:
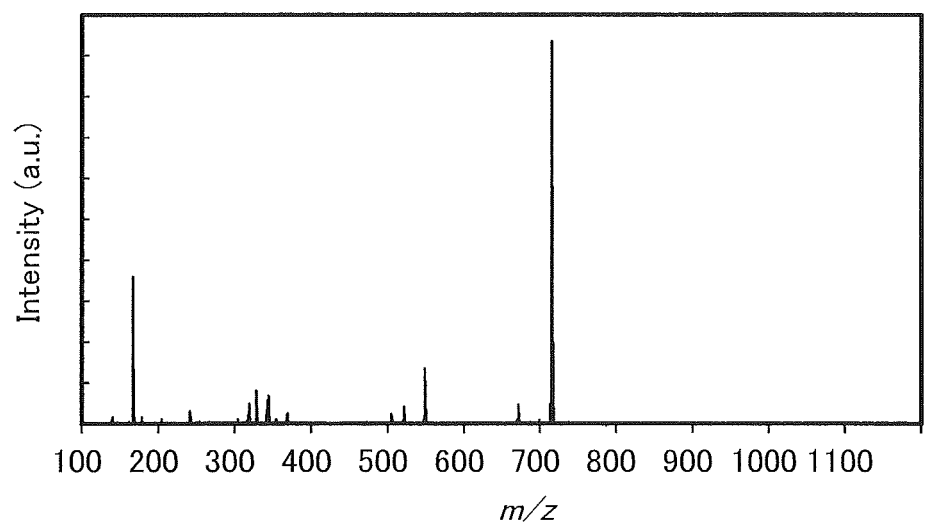
FIG. 18 shows results of LC-MS measurement on the heterocyclic compound represented by the structural formula (100)

FIG. 18 shows the measurement results. The results in FIG. 18 reveal that the product ions of 4,6mCzBP2Pm (the structural formula (100)), which is the heterocyclic compound of one embodiment of the present invention, are detected mainly around m/z=715, around m/z=548, and around m/z=166. Note that the results in FIG. 18 show characteristics derived from 4,6mCzBP2Pm and thus can be regarded as important data for identifying 4,6mCzBP2Pm contained in a mixture.

Next, 4,6mCzBP2Pm was subjected to cyclic voltammetry (CV) measurement. An electrochemical analyzer (ALS model 600A or 600C, manufactured by BAS Inc.) was used for the CV measurement.

Figure 19:
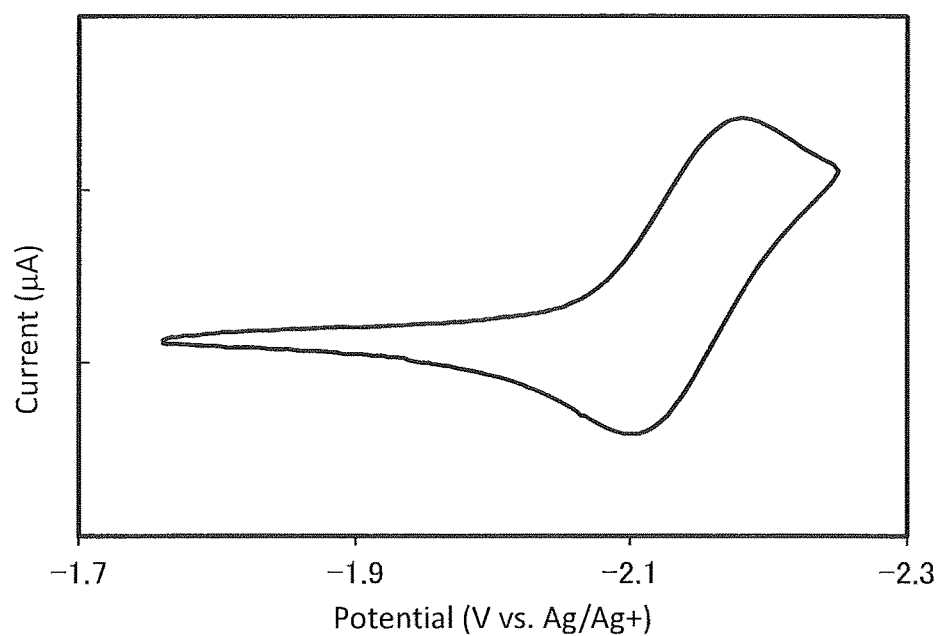
FIG. 19 shows results of CV measurement on the heterocyclic compound represented by the structural formula (100)

As for a solution used for the CV measurement, dehydrated dimethylformamide (DMF, produced by Sigma-Aldrich Inc., 99.8%, Catalog No. 227056-12) was used as a solvent, and tetra-n-butylammonium perchlorate (electrochemical grade, Wako Pure Chemical Industries, Ltd., manufacturer's code: 043999, CAS. No. 1923-70-2), which was a supporting electrolyte, was dissolved in the solvent so that the concentration of tetra-n-butylammonium perchlorate can be 100 mmol/L. Further, the measurement target was dissolved in the solution so that the concentration thereof can be 2 mmol/L. Then, the solution was put into an electrochemical cell, electrodes were set, and then degasification by argon bubbling was performed for approximately 30 minutes. The electrodes used for the measurement were a platinum electrode (produced by BAS Inc., PTE platinum electrode) as a working electrode, a platinum electrode (produced by BAS Inc., Pt counter electrode) as an auxiliary electrode, and a reference electrode for nonaqueous solvent (produced by BAS Inc., RE-7 reference electrode for nonaqueous solvent (Ag/Ag$^+$)) as a reference electrode. In the CV measurement, room temperature (20° C. to 25° C.) and a scan rate of 0.1 V/sec were employed. Note that the potential energy of the reference electrode with respect to the vacuum level was assumed to be −4.94 eV in this example. The reduction characteristics (initial) obtained by the CV measurement are shown in FIG. 19.

In this CV measurement, the electrode potential of the working electrode with respect to that of the reference electrode was swept from −1.76 V to −2.25 V in the negative direction, and then swept from −2.25 V to −1.76 V in the reverse direction. These sweeps in the negative and positive directions are one cycle, and measurement was performed until 100 cycles were carried out. An observed reduction peak had 93% of the initial intensity even after 100 cycles. This indicates that 4,6mCzBP2Pm has high resistance against repetition of redox reactions between a reduced state and a neutral state.

The LUMO level (reduction potential) of 4,6mCzBP2Pm was calculated from the CV measurement results. From an oxidation peak potential (from the reduction state to the neutral state) $E_{pc}$[V] and a reduction peak potential (from the neutral state to the reduction state) $E_{pa}$[V], a half wave potential (a potential intermediate between $E_{pa}$ and $E_{pc}$) was calculated to be −2.14 eV(=($E_{pa}$+$E_{pc}$)/2 [V]). Then, this half wave potential (−2.14 eV) was subtracted from the potential energy of the reference electrode with respect to the vacuum level (−4.94 eV), so that a LUMO level (a reduction potential) of 4,6mCzBP2Pm of −2.80 eV was obtained.

EXAMPLE 2

Synthesis Example 2

In this example, a method of synthesizing 9,9'-[pyridine-3,5-diyl bis(biphenyl-3,3'-diyl)]bis(9H-carbazole) (abbreviation: 3,5mCzBP2Py) (the structural formula (200)), which is a heterocyclic compound of one embodiment of the present invention, is described. The structure of 3,5mCzBP2Py is shown below.

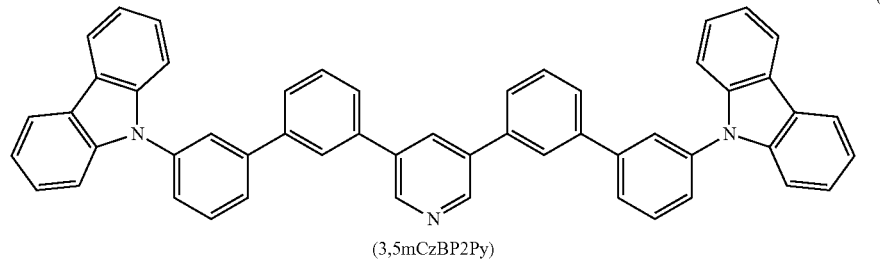

(200)

(3,5mCzBP2Py)

Synthesis of 3,5mCzBP2Py

First, 0.71 g (3.0 mmol) of 3,5-dibromopyridine, 2.2 g (6.1 mmol) of 3-(3-(9H-carbazol-9-yl)phenyl)phenyl boronic acid, and 55 mg (0.18 mmol) of tris(2-methylphenyl)phosphine were put into a 50-mL three-neck flask, and the air in the flask was replaced with nitrogen.

Then, 3.0 mL of a 2M potassium carbonate aqueous solution, 12 mL of toluene, and 3 mL of ethanol were added to this mixture, and the mixture was degassed by being stirred under reduced pressure. To this mixture, 50 mg (0.22 mmol) of palladium(II) acetate was added and stirring was performed under a nitrogen stream at 90° C. for 11 hours. After the stirring, water was added to the mixture, and an aqueous layer was subjected to extraction with ethyl acetate.

The obtained solution of the extract and an organic layer were combined, and the mixture was washed with water and saturated brine. Then, the mixture was dried with magnesium sulfate. This mixture was separated by gravity filtration, and the filtrate was concentrated to give an oily substance. The oily substance was purified by silica gel column chromatography (developing solvent: hexane and ethyl acetate in a ratio of 5:1). The obtained fraction was concentrated to give a solid. This solid was purified by high performance liquid column chromatography (HPLC) (developing solvent:chloroform) to give a solid.

Hexane was added to the obtained solid, and ultrasonic wave irradiation was performed. A solid was collected by suction filtration to give 1.3 g of a white solid, which was the target substance, in a yield of 62%.

By a train sublimation method, 1.3 g of the obtained white solid was purified. In the purification by sublimation, the white solid was heated at 340° C. under the conditions where the pressure was 3.0 Pa and the argon flow rate was 5 mL/min. After the purification by sublimation, 1.1 g of a white solid was obtained at a collection rate of 85%. A synthesis scheme of the above synthesis method is shown in (B-1) below.

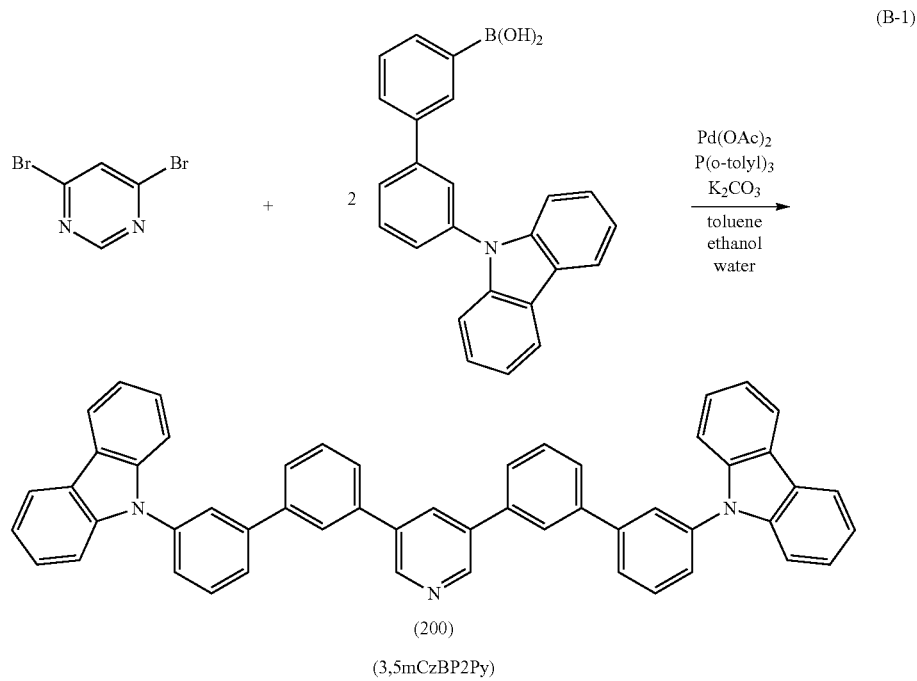

(B-1)

(200)

(3,5mCzBP2Py)

Figure 20A:
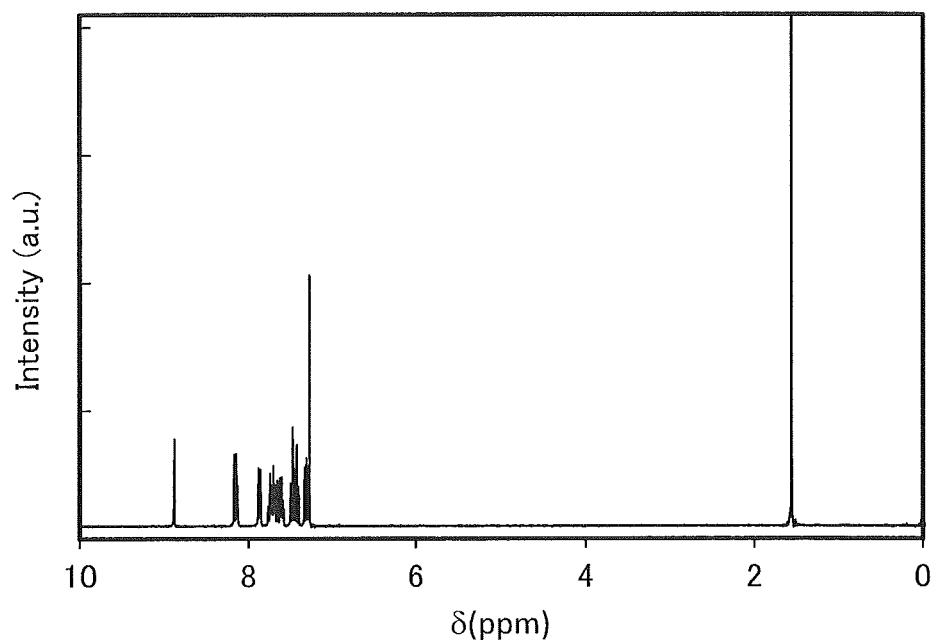
FIGS. 20A and 20B show a $^1$H-NMR chart of a heterocyclic compound represented by the structural formula (200)
Figure 20B:
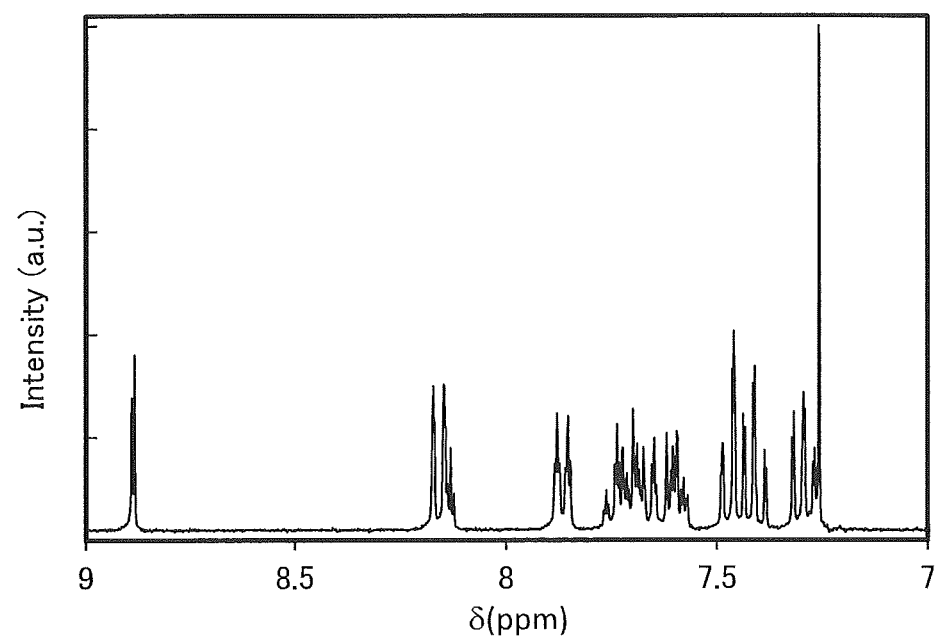

Analysis results by nuclear magnetic resonance ($^1$H-NMR) spectroscopy of the white solid obtained by the above-described synthesis method are described below. FIGS. 20A and 20B show the $^1$H-NMR chart. FIG. 20B is a chart where the range from 7 (ppm) to 9 (ppm) on the horizontal axis (δ) in FIG. 20A is enlarged. The results revealed that 3,5mCzBP2Py (the structural formula (200)), which is a heterocyclic compound of one embodiment of the present invention, was obtained in this example.

$^1$H-NMR (CDCl$_3$, 300 MHz): δ=7.30 (td, J=7.4 Hz, 0.9 Hz, 4H), 7.38-7.49 (m, 8H), 7.57-7.77 (m, 12H), 7.85 (s, 2H), 7.88 (s, 2H), 8.12-8.17 (m, 5H), 8.89 (s, d, J=2.1 Hz, 2H).

Figure 21A:
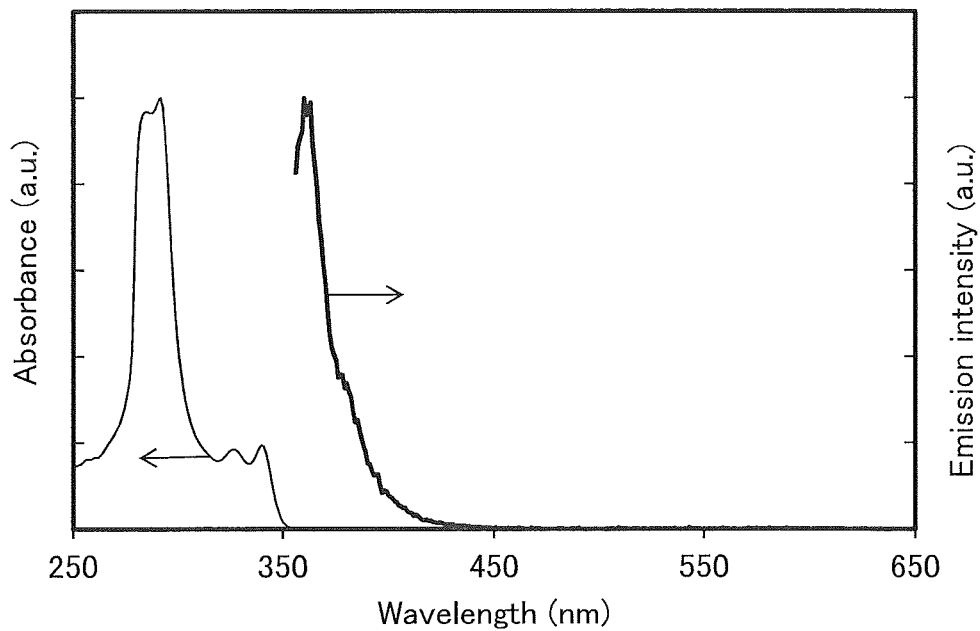
FIGS. 21A and 21B show ultraviolet-visible absorption spectra and emission spectra of the heterocyclic compound represented by the structural formula (200)
Figure 21B:
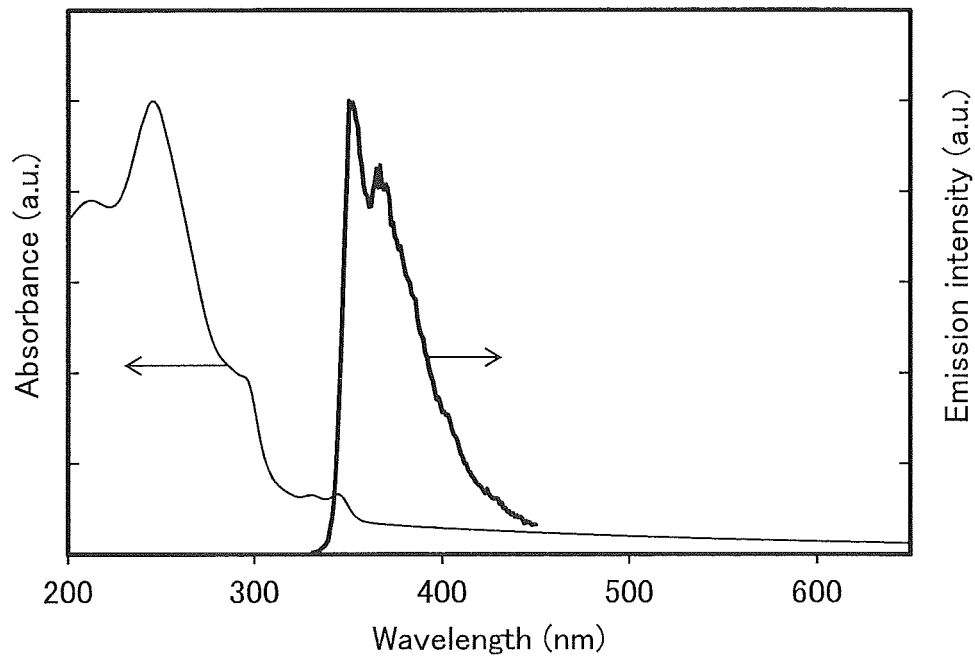

Next, ultraviolet-visible absorption spectra (hereinafter, simply referred to as "absorption spectra") and emission spectra of 3,5mCzBP2Py in a toluene solution of 3,5mCzBP2Py and a thin film of 3,5mCzBP2Py were measured at room temperature. The spectra of the toluene solution of 3,5mCzBP2Py were measured by putting the solution in a quartz cell. The spectra of the thin film were measured with a sample prepared by evaporation of 3,5mCzBP2Py on a quartz substrate. The absorption spectra were measured with an ultraviolet-visible light spectrophotometer (V-550, manufactured by JASCO Corporation), and the emission spectra were measured with a fluorescence spectrophotometer (FS920, manufactured by Hamamatsu Photonics K.K.). FIG. 21A shows the obtained absorption and emission spectra of 3,5mCzBP2Py in the toluene solution, and FIG. 21B shows the obtained absorption and emission spectra of the thin film. The horizontal axis represents wavelength and the vertical axes represent absorbance and emission intensity. The absorption spectrum shown in FIG. 21A was obtained by subtraction of the absorption spectra of toluene and the quartz cell from the obtained absorption spectrum. The absorption spectrum shown in FIG. 21B was obtained by subtraction of the absorption spectrum of the quartz substrate from the obtained absorption spectrum.

According to the above measurement, 3,5mCzBP2Py, which is a heterocyclic compound of one embodiment of the present invention, in the toluene solution has absorption peaks at approximately 341 nm, 328 nm, 292 nm, and 285 nm, and an emission peak at approximately 360 nm. In addition, the thin film of 3,5mCzBP2Py has absorption peaks at approximately 348 nm, 335 nm, 295 nm, and 244 nm, and emission peaks at approximately 365 nm and 350 nm. Thus, it was found that absorption and emission of 3,5mCzBP2Py occur in extremely short wavelength regions.

Figure 22:
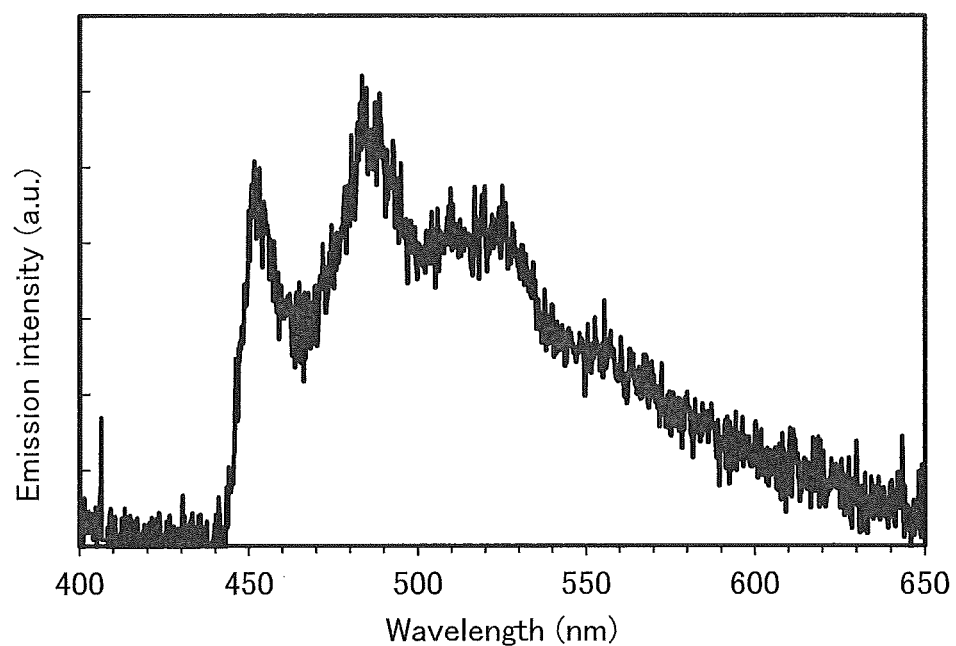
FIG. 22 shows a phosphorescence spectrum of the heterocyclic compound represented by the structural formula (200)

Phosphorescence of 3,5mCzBP2Py was measured. The measurement was performed by using a PL microscope, LabRAM HR-PL, produced by HORIBA, Ltd., a He—Cd laser (325 nm) as excitation light, and a CCD detector at a measurement temperature of 10 K. For the measurement, a thin film as a sample was formed over a quartz substrate to a thickness of approximately 50 nm and another quartz substrate was attached to the deposition surface in a nitrogen atmosphere. The measurement results are shown in FIG. 22. The results showed that the peak on the shortest wavelength side of a phosphorescence spectrum of 3,5mCzBP2Py is at approximately 450 nm, which means that 3,5mCzBP2Py has a high T1 level.

Next, 3,5mCzBP2Py was analyzed by liquid chromatography mass spectrometry (LC/MS). The analysis by LC/MS was carried out with Acquity UPLC (manufactured by Waters Corporation), and Xevo G2 Tof MS (manufactured by Waters Corporation).

In the MS analysis, ionization was carried out by an electrospray ionization (ESI) method. At this time, the capillary voltage and the sample cone voltage were set to 3.0 kV and 30 V, respectively, and detection was performed in a positive mode. A component that underwent the ionization under the above-described conditions was collided with an argon gas in a collision cell to dissociate into product ions. The energy (collision energy) for the collision with argon was 70 eV. The mass range for the measurement was m/z=100 to 1200.

Figure 23:
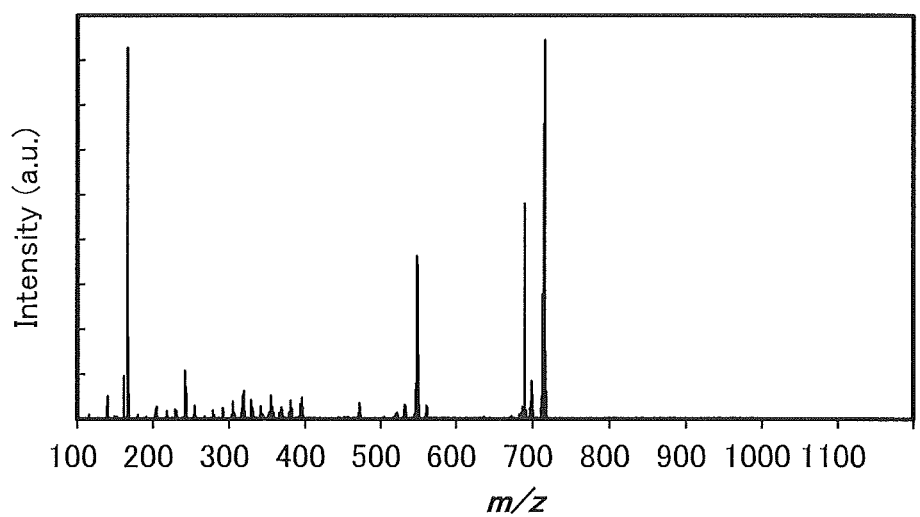
FIG. 23 shows results of LC-MS measurement on the heterocyclic compound represented by the structural formula (200)

FIG. 23 shows the measurement results. The results in FIG. 23 reveal that the product ions of 3,5mCzBP2Py (the structural formula (200)), which is the heterocyclic compound of one embodiment of the present invention, are detected mainly around m/z=715, around m/z=689, around m/z=547, and around m/z=166. Note that the results in FIG. 23 show characteristics derived from 3,5mCzBP2Py and thus can be regarded as important data for identifying 3,5mCzBP2Py contained in a mixture.

Figure 24:
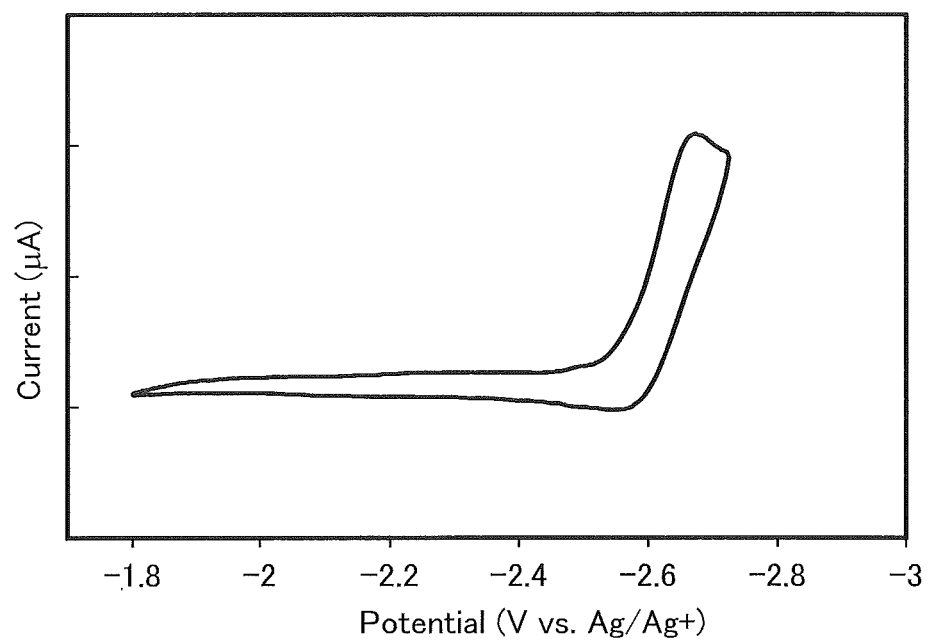
FIG. 24 shows results of CV measurement on the heterocyclic compound represented by the structural formula (200)

Next, 3,5mCzBP2Py was subjected to cyclic voltammetry (CV) measurement. Because the CV measurement was performed in the same manner as that described in Example 1, the description thereof is omitted here. The reduction characteristics (initial) obtained by the CV measurement are shown in FIG. 24.

In this CV measurement, the electrode potential of the working electrode with respect to that of the reference electrode was swept from −1.80 V to −2.72 V in the negative direction, and then swept from −2.72 V to −1.80 V in the reverse direction. These sweeps in the negative and positive directions are one cycle, and measurement was performed until 100 cycles were carried out. An observed reduction peak had 93% of the initial intensity even after 100 cycles. This indicates that 3,5mCzBP2Py has high resistance against repetition of redox reactions between a reduced state and a neutral state.

The LUMO level (reduction potential) of 3,5mCzBP2Py was calculated from the CV measurement results. From an oxidation peak potential (from the reduction state to the neutral state) $E_{pc}$[V] and a reduction peak potential (from the neutral state to the reduction state) $E_{pa}$[V], a half wave potential (a potential intermediate between $E_{pa}$ and $E_{pc}$) was calculated to be −2.61 eV(=($E_{pa}$+$E_{pc}$)/2 [V]). Then, this half wave potential (−2.61 eV) was subtracted from the potential energy of the reference electrode with respect to the vacuum level (−4.94 eV), so that a LUMO level (a reduction potential) of 3,5mCzBP2Py of −2.33 eV was obtained.

EXAMPLE 3

Figure 25:
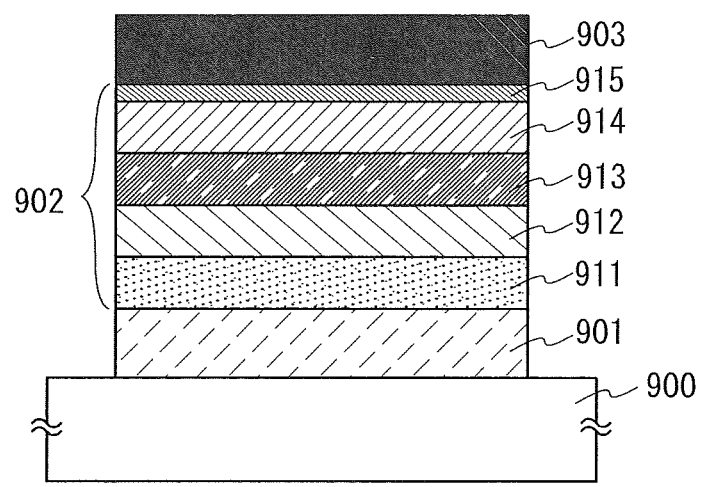
FIG. 25 illustrates a light-emitting element.
Figure 26:
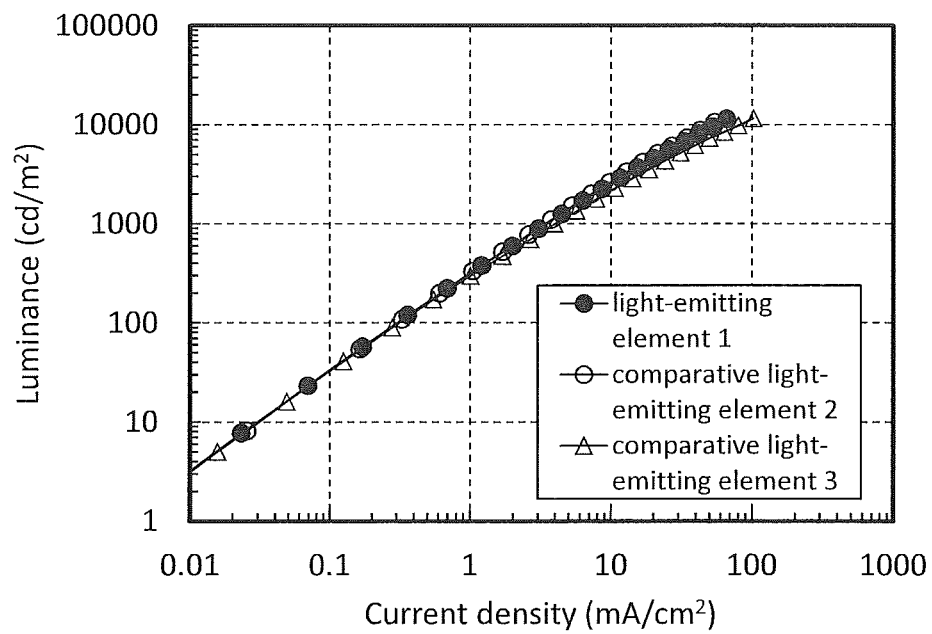
FIG. 26 shows current density-luminance characteristics of a light-emitting element 1, a comparative light-emitting element 2, and a comparative light-emitting element 3.
Figure 27:
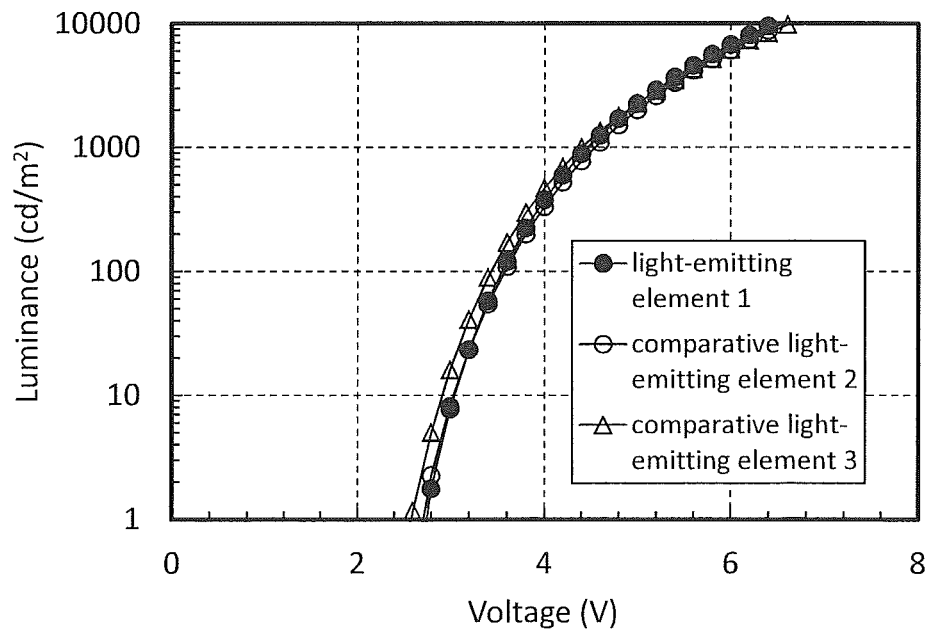
FIG. 27 shows voltage-luminance characteristics of the light-emitting element 1, the comparative light-emitting element 2, and the comparative light-emitting element 3.
Figure 28:
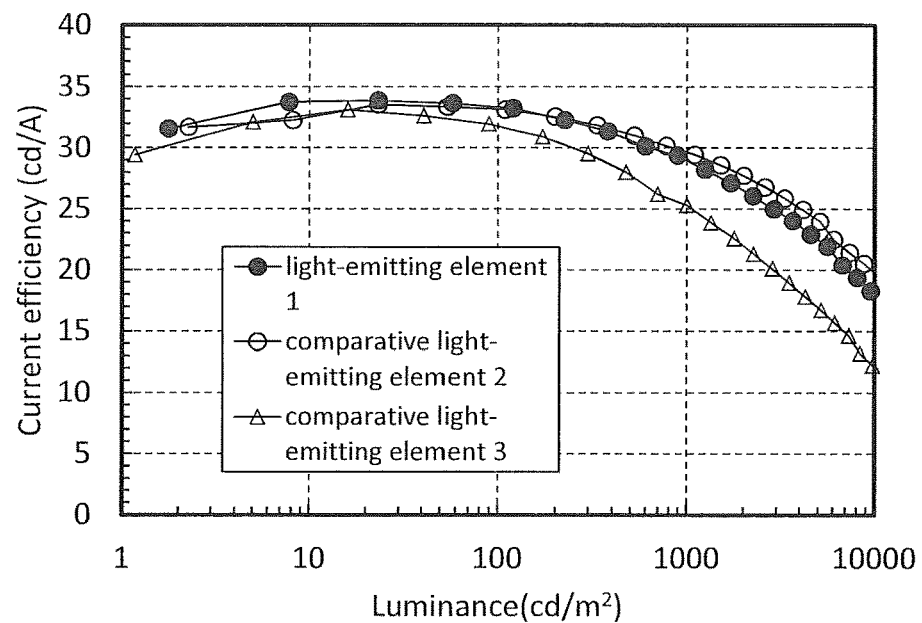
FIG. 28 shows luminance-current efficiency characteristics of the light-emitting element 1, the comparative light-emitting element 2, and the comparative light-emitting element 3.
Figure 29:
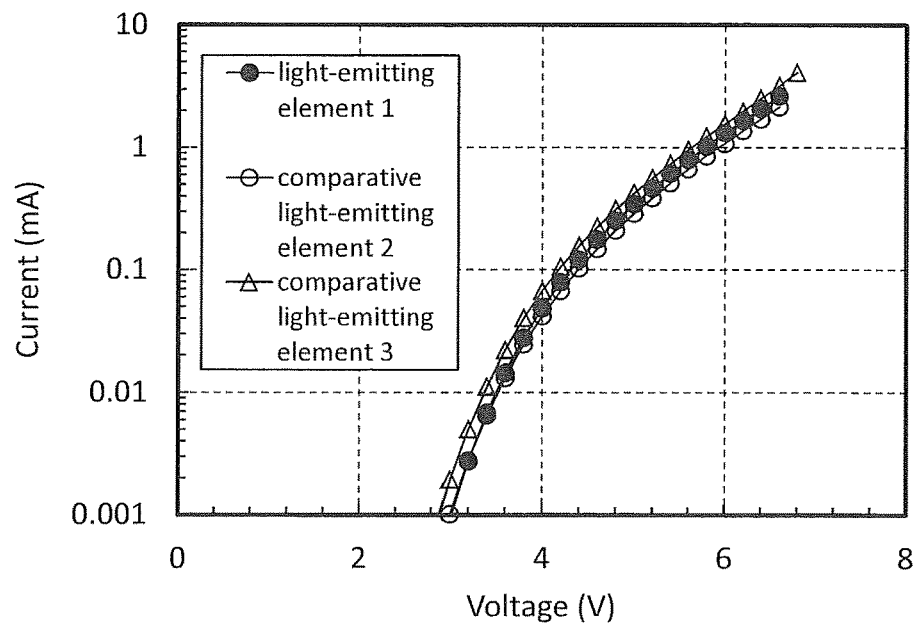
FIG. 29 shows voltage-current characteristics of the light-emitting element 1, the comparative light-emitting element 2, and the comparative light-emitting element 3.

In this example, a light-emitting element 1 that includes 4,6mCzBP2Pm (the structural formula (100)), which is a heterocyclic compound of one embodiment of the present invention, was fabricated. In addition, for reference, a comparative light-emitting element 2 that includes 2Ph-4,6mCzBP2Pm and a comparative light-emitting element 3 that includes 4,6mCzP2Pm were fabricated. Note that the fabrication of the light-emitting element 1 and the comparative light-emitting elements 2 and 3 is described with reference to FIG. 25. Chemical formulae of materials used in this example are shown below.

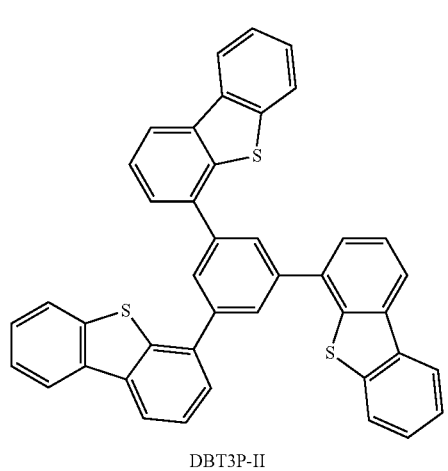
DBT3P-II

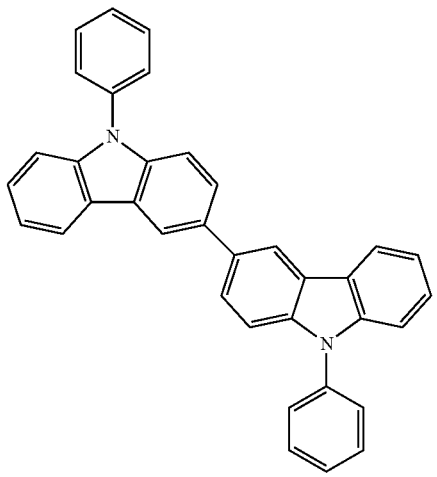
PCCP

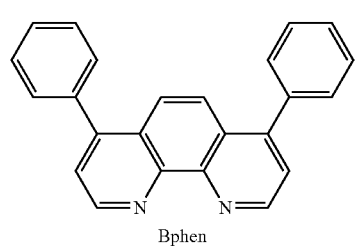
Bphen

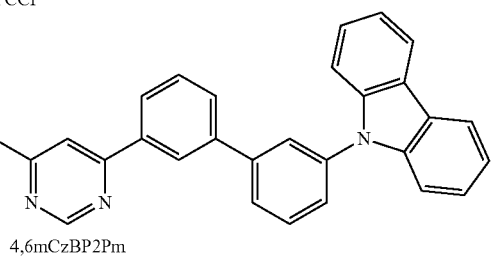
4,6mCzBP2Pm
(100)

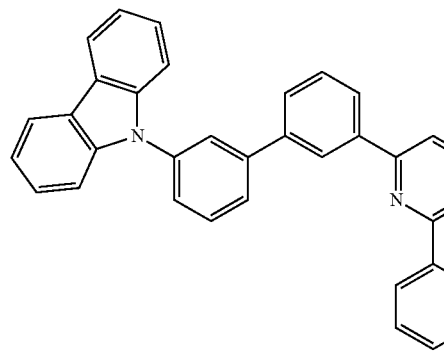
2Ph-4,6mCzBP2Pm

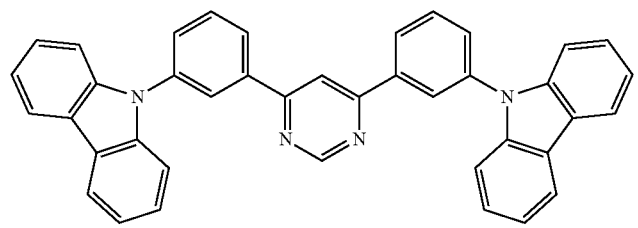
4,6mCzP2Pm

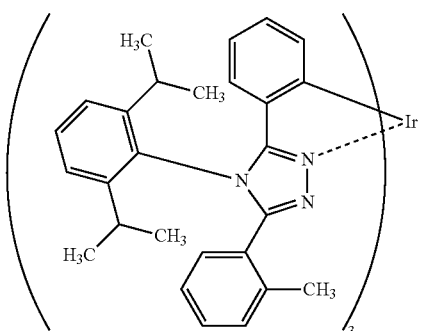
[Ir(mpptz-diPrp)$_3$]

<<Fabrication of Light-Emitting Element 1 and Comparative Light-Emitting Elements 2 and 3>>

First, indium tin oxide (ITO-2) containing silicon oxide was deposited over a glass substrate 900 by a sputtering method, whereby a first electrode 901 functioning as an anode was formed. Note that the thickness was set to 110 nm and the electrode area was set to 2 mm×2 mm.

Next, as pretreatment for fabricating the light-emitting element 1 over the substrate 900, UV ozone treatment was performed for 370 seconds after washing of a surface of the substrate with water and baking that was performed at 200° C. for 1 hour.

After that, the substrate was transferred into a vacuum evaporation apparatus where the pressure had been reduced to approximately $10^{-4}$ Pa, and subjected to vacuum baking at 170° C. in a heating chamber of the vacuum evaporation apparatus for 30 minutes, and then the substrate 900 was cooled down for approximately 30 minutes.

Next, the substrate 900 was fixed to a holder provided in the vacuum evaporation apparatus so that a surface of the substrate provided with the first electrode 901 faced downward. In this example, a case is described in which a hole-injection layer 911, a hole-transport layer 912, a light-emitting layer 913, an electron-transport layer 914, and an electron-injection layer 915, which were included in an EL layer 902, were sequentially formed by a vacuum evaporation method.

After the pressure in the vacuum apparatus was reduced to $10^{-4}$ Pa, 1,3,5-tri(dibenzothiophen-4-yl)benzene (abbreviation: DBT3P-II) and molybdenum oxide were deposited by co-evaporation so that the mass ratio of DBT3P-II to molybdenum oxide was 4:2, whereby the hole-injection layer 911 was formed over the first electrode 901. The thickness of the hole-injection layer 911 was set to 60 nm. Note that co-evaporation is an evaporation method in which a plurality of different substances are concurrently vaporized from different evaporation sources.

Then, 9-phenyl-9H-3-(9-phenyl-9H-carbazol-3-yl)carbazole (abbreviation: PCCP) was deposited by evaporation to a thickness of 20 nm, whereby the hole-transport layer 912 was formed.

Next, the light-emitting layer 913 was formed over the hole-transport layer 912. The light-emitting layer in this example includes at least a light-emitting substance (dopant) and a host material.

The light-emitting layer 913 for the light-emitting element 1 was formed to have a thickness of 40 nm with a stacked-layer structure as follows: PCCP, 4,6mCzBP2Pm, and tris{2-[5-(2-methylphenyl)-4-(2,6-diisopropylphenyl)-4H-1,2,4-triazol-3-yl-κN2]phenyl-κC} iridium(III) (abbreviation: [Ir(mpptz-diPrp)$_3$]) were deposited to a thickness of 30 mn by co-evaporation so that the mass ratio of PCCP to 4,6mCzBP2Pm and [Ir(mpptz-diPrp)$_3$] was 1:0.3:0.06, and then 4,6mCzBP2Pm and [Ir(mpptz-diPrp)$_3$] were deposited to a thickness of 10 nm by co-evaporation so that the mass ratio of 4,6mCzBP2Pm to [Ir(mpptz-diPrp)$_3$] was 1:0.06.

The light-emitting layer 913 for the comparative light-emitting element 2 was formed to have a thickness of 40 nm with a stacked-layer structure in the following manner: PCCP, 9,9'-[(2-phenyl-pyrimidine-4,6-diyl)bis(biphenyl-3,3'-diyl)]bis(9H-carbazole) (abbreviation: 2Ph-4,6mCzBP2Pm), and [Ir(mpptz-diPrp)$_3$] were deposited to a thickness of 30 nm by co-evaporation so that the mass ratio of PCCP to 2Ph-4,6mCzBP2Pm and [Ir(mpptz-diPrp)$_3$] was 1:0.3:0.06, and then 2Ph-4,6mCzBP2Pm and [Ir(mpptz-diPrp)$_3$] were deposited to a thickness of 10 nm by co-evaporation so that the mass ratio of 2Ph-4,6mCzBP2Pm to [Ir(mpptz-diPrp)$_3$] was 1:0.06.

The light-emitting layer 913 for the comparative light-emitting element 3 was formed to have a thickness of 40 nm with a stacked-layer structure as follows: PCCP, 9,9'-(pyrimidine-4,6-diyldi-3,1-phenylene)bis(9H-carbazole) (abbreviation: 4,6mCzP2Pm), and [Ir(mpptz-diPrp)$_3$]) were deposited to a thickness of 30 nm by co-evaporation so that the mass ratio of PCCP to 4,6mCzP2Pm and [Ir(mpptz-diPrp)$_3$] was 1:0.3:0.06, and then 4,6mCzP2Pm and [Ir(mpptz-diPrp)$_3$] were deposited to a thickness of 10 nm by co-evaporation so that the mass ratio of 4,6mCzP2Pm to [Ir(mpptz-diPrp)$_3$] was 1:0.06.

Next, over the light-emitting layer 913, the electron-transport layer 914 was formed. In the light-emitting element 1, the electron-transport layer 914 was formed by depositing 4,6mCzBP2Pm, by evaporation to a thickness of 10 nm and then depositing Bphen by evaporation to a thickness of 15 nm. In the comparative light-emitting element 2, the electron-transport layer 914 was formed by depositing 2Ph-4,6mCzBP2Pm by evaporation to a thickness of 10 nm and then depositing Bphen by evaporation to a thickness of 15 nm. In the comparative light-emitting element 3, the electron-transport layer 914 was formed by depositing 4,6mCzP2Pm by evaporation to a thickness of 10 nm and then depositing Bphen by evaporation to a thickness of 15 mn.

Furthermore, over the electron-transport layer 914, lithium fluoride was deposited by evaporation to a thickness of 1 nm to form the electron-injection layer 915.

Finally, aluminum was deposited to a thickness of 200 nm over the electron-injection layer 915 by evaporation, whereby a second electrode 903 functioning as a cathode was formed. Through the above-described steps, the light-emitting element 1 and the comparative light-emitting elements 2 and 3 were fabricated. Note that in all the above evaporation steps, evaporation was performed by a resistance-heating method.

Table 1 shows the element structures of the light-emitting element 1 and the comparative light-emitting elements 2 and 3 fabricated by the above-described method.

TABLE 1

|  | First electrode | Hole-injection layer | Hole-transport layer | Light-emitting layer | Electron-transport layer | Electron-injection layer | Second electrode |
| --- | --- | --- | --- | --- | --- | --- | --- |
| Light-emitting element 1 | ITO-2 (110 nm) | DBT3P-II:MoOx (4:2, 60 nm) | PCCP (20 nm) | * | 4,6mCzBP2Pm (10 nm) | Bphen (15 nm) | LiF (1 nm) | Al (200 nm) |
| Comparative light-emitting element 2 | ITO-2 (110 nm) | DBT3P-II:MoOx (4:2, 60 nm) | PCCP (20 nm) | ** | 2Ph-4,6mCzBP2Pm (10 nm) | Bphen (15 nm) | LiF (1 nm) | Al (200 nm) |
| Comparative light-emitting element 3 | ITO-2 (110 nm) | DBT3P-II:MoOx (4:2, 60 nm) | PCCP (20 nm) | *** | 4,6mCzP2Pm (10 nm) | Bphen (15 nm) | LiF (1 nm) | Al (200 nm) |

\* PCCP:4,6mCzBP2Pm:[Ir(mpptz-diPrp)$_3$]\4,6mCzBP2Pm:[Ir(mpptz-diPrp)$_3$] (1:0.3:0.06 (30 nm)\1:0.06 (10 nm))
\*\* PCCP:2Ph-4,6mCzBP2Pm:[Ir(mpptz-diPrp)$_3$]\2Ph-4,6mCzBP2Pm:[Ir(mpptz-diPrp)$_3$] (1:0.3:0.06 (30 nm)\1:0.06 (10 nm))
\*\*\* PCCP:4,6mCzP2Pm:[Ir(mpptz-diPrp)$_3$]\4,6mCzP2Pm:[Ir(mpptz-diPrp)$_3$] (1:0.3:0.06 (30 nm)\1:0.06 (10 nm))

The fabricated light-emitting element 1 and the comparative light-emitting elements 2 and 3 were sealed in a glove box under a nitrogen atmosphere so as not to be exposed to the air (a sealant was applied to surround the elements, and at the time of sealing, UV treatment was performed and heat treatment was performed at 80° C. for 1 hour).

<<Operation Characteristics of Light-Emitting Element 1 and Comparative Light-Emitting Elements 2 and 3>>

Operation characteristics of the fabricated light-emitting element 1 and the comparative light-emitting elements 2 and 3 were measured. Note that the measurement was carried out at room temperature (in an atmosphere kept at 25° C.).

FIG. 26, FIG. 27, FIG. 28, and FIG. 29 show current density-luminance characteristics, voltage-luminance characteristics, luminance-current efficiency characteristics, and voltage-current characteristics, respectively, of the light-emitting element 1 and the comparative light-emitting elements 2 and 3.

Table 2 shows initial values of main characteristics of the light-emitting element 1 and the comparative light-emitting elements 2 and 3 at a luminance of approximately 1000 cd/m$^2$.

TABLE 2

|  | Voltage (V) | Current (mA) | Current density (mA/cm$^2$) | Chromaticity (x, y) | Luminance (cd/m$^2$) | Current efficiency (cd/A) | Power efficiency (lm/W) | External quantum efficiency (%) |
| --- | --- | --- | --- | --- | --- | --- | --- | --- |
| Light-emitting element 1 | 4.4 | 0.12 | 3.0 | (0.19, 0.33) | 890 | 29 | 21 | 13 |
| Comparative light-emitting element 2 | 4.6 | 0.15 | 3.7 | (0.19, 0.33) | 1100 | 29 | 20 | 13 |
| Comparative light-emitting element 3 | 4.4 | 0.16 | 4.0 | (0.21, 0.36) | 1000 | 25 | 18 | 11 |

Figure 30:
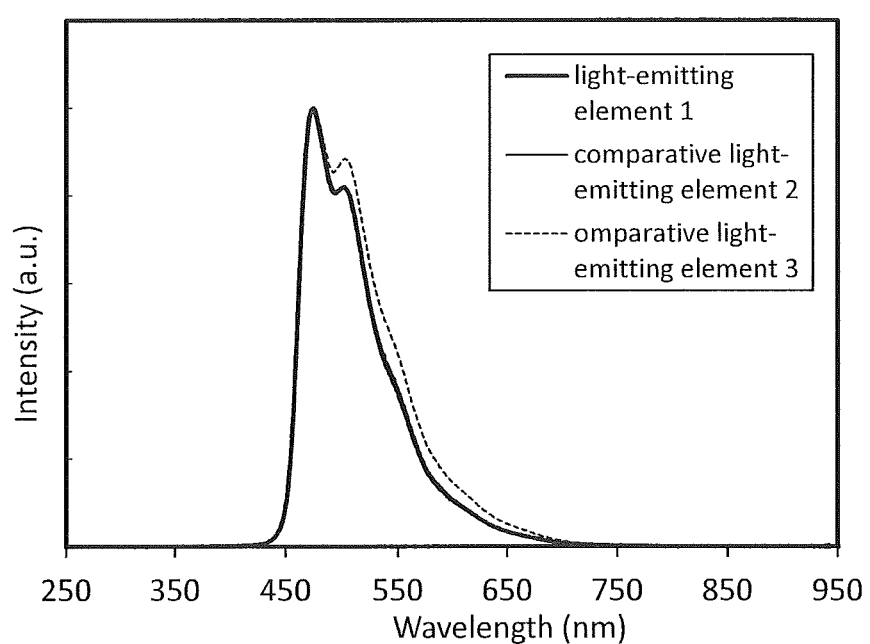
FIG. 30 shows emission spectra of the light-emitting element 1, the comparative light-emitting element 2, and the comparative light-emitting element 3.

FIG. 30 shows emission spectra of the light-emitting element 1 and the comparative light-emitting elements 2 and 3 to which current was applied at a current density of 25 mA/cm$^2$. As shown in FIG. 30, the emission spectra of the light-emitting element 1 and the comparative light-emitting elements 2 and 3 each have a peak at around 476 nm and it is suggested that the peak is derived from blue light emission of the organometallic complex, [Ir(mpptz-diPrp)$_3$], used in the EL layer of each light-emitting element.

Figure 31:
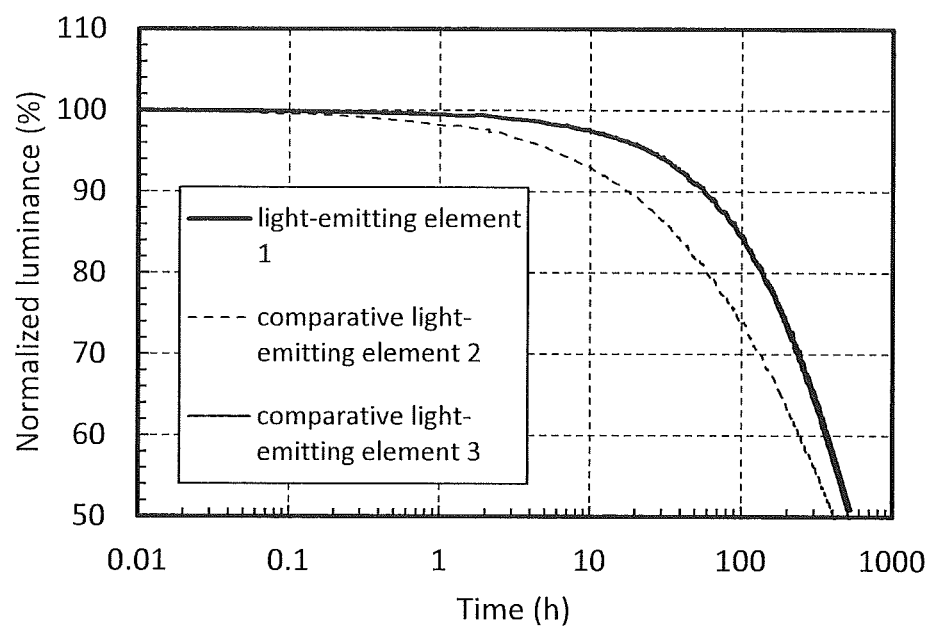
FIG. 31 shows reliability of the light-emitting element 1, the comparative light-emitting element 2, and the comparative light-emitting element 3.
Figure 32:
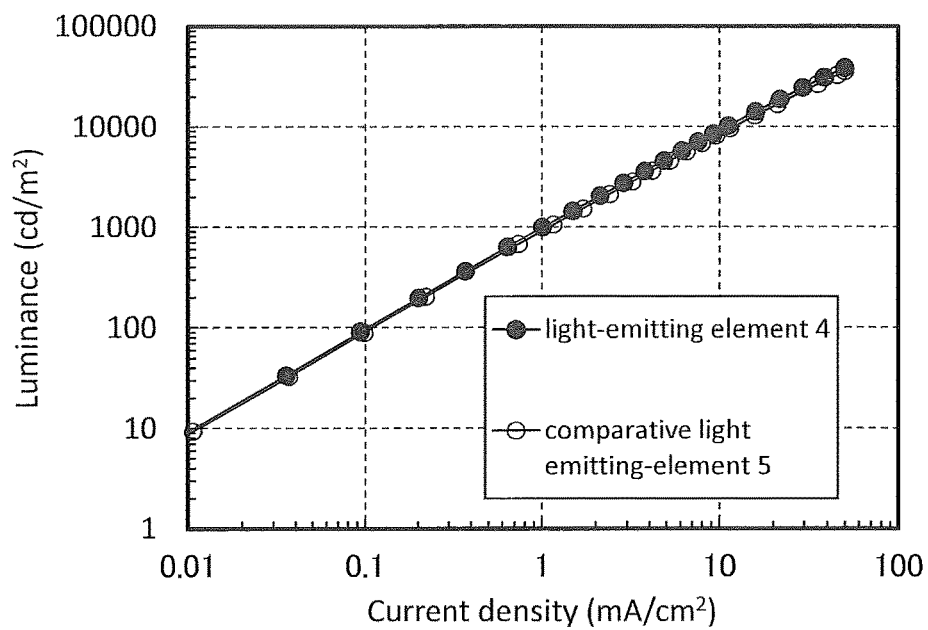
FIG. 32 shows current density-luminance characteristics of a light-emitting element 4 and a comparative light-emitting element 5.
Figure 33:
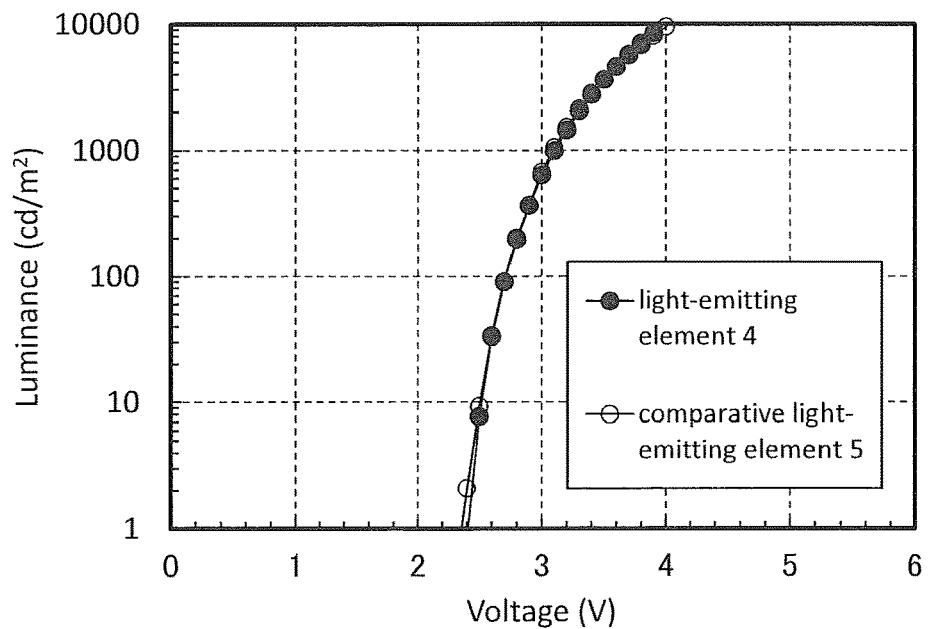
FIG. 33 shows voltage-luminance characteristics of the light-emitting element 4 and the comparative light emitting-element 5.
Figure 34:
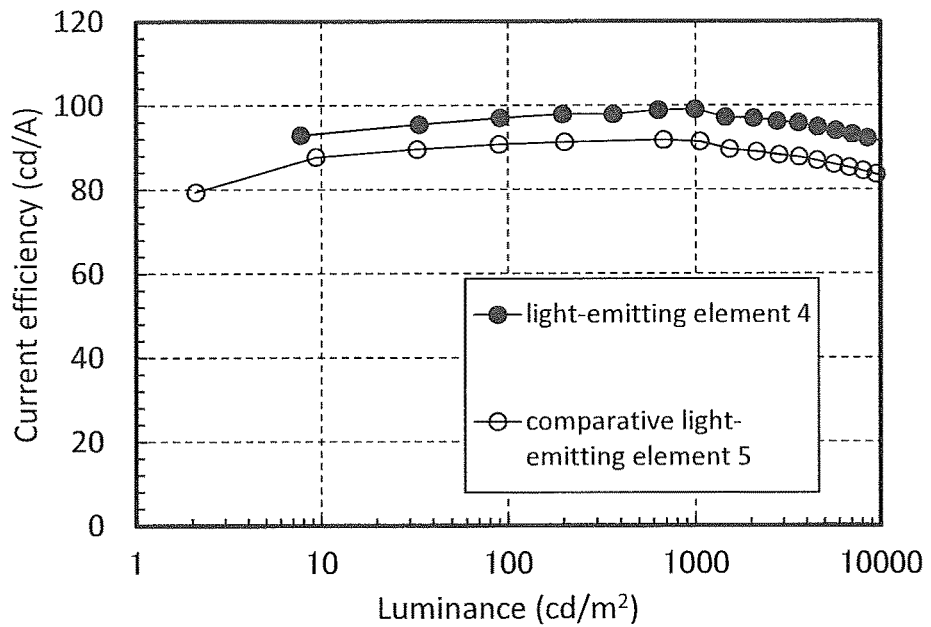
FIG. 34 shows luminance-current efficiency characteristics of the light-emitting element 4 and the comparative light-emitting element 5.
Figure 35:
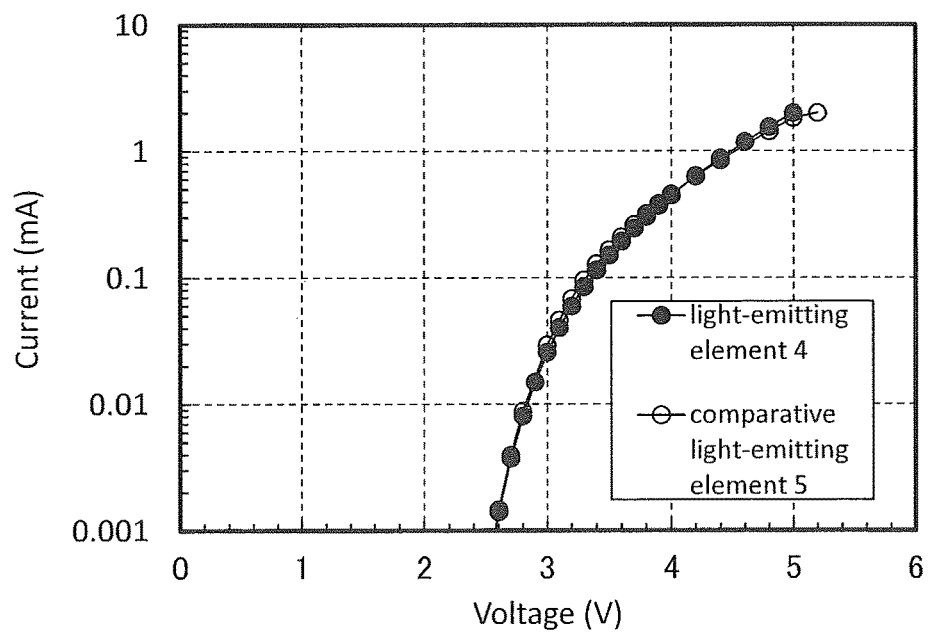
FIG. 35 shows voltage-current characteristics of the light-emitting element 4 and the comparative light-emitting element 5.

A reliability test was performed on the light-emitting element 1 and the comparative light-emitting elements 2 and 3. FIG. 31 shows results of the reliability test. In FIG. 31, the vertical axis represents normalized luminance (%) with an initial luminance of 100% and the horizontal axis represents driving time (h) of the light-emitting elements. Note that in the reliability test, the light-emitting element 1 and the comparative light-emitting elements 2 and 3 were driven under the conditions where the initial luminance was set to 5000 cd/m$^2$ and the current density was constant.

The light-emitting element 1 uses 4,6mCzBP2Pm, which is one embodiment of the present invention, in the EL layer. Note that 4,6mCzBP2Pm has a structure in which two substituents in total are bonded to the 4- and 6-positions of a pyrimidine skeleton, where each of the two substituents is a substituent that can bond a heterocyclic group including a carbazole skeleton to the pyrimidine skeleton via an arylene group. Similarly, 4,6mCzP2Pm used in the EL layer of the comparative light-emitting element 3 has a structure in which two substituents in total are bonded to a pyrimidine skeleton. In contrast, 2Ph-4,6mCzBP2Pm used in the EL layer of the comparative light-emitting element 2 has a structure in which three substituents in total are bonded to a pyrimidine skeleton.

The results shown in FIG. 31 indicate that a difference in the number of substituents affects the reliability. In other words, the reliability in the case where two substituents in total are included as in 4,6mCzBP2Pm or 4,6mCzP2Pm is higher than the reliability in the case where three substituents in total are included as in 2Ph-4,6mCzBP2Pm.

Moreover, it is found from Table 2 that higher efficiencies can be obtained when the arylene groups included in the substituents at the 4- and 6-positions of the pyrimidine skeleton (the substituents that can each bond a heterocyclic group including a carbazole skeleton to the pyrimidine skeleton via an arylene group) are biphenyl structures, than when the arylene groups are phenyl structures. In other words, the light-emitting element 1 that uses 4,6mCzBP2Pm, which has a biphenyl structure, in the EL layer and the comparative light-emitting element 2 that uses 2Ph-4,6mCzBP2Pm, which also has a biphenyl structure, in the EL layer have higher efficiencies than the comparative light-emitting element 3 that uses 4,6mCzP2Pm, which has a phenyl structure, in the EL layer.

The difference in the efficiencies depending on the structure of the arylene groups occurred probably because the efficiencies are determined by how easily an exciplex is formed between these substances and a dopant in the light-emitting layer. The easiness of forming an exciplex with a dopant can be found from the LUMO level (reduction potential) of the substance. That is, in the light-emitting layer of this example, when the difference between the LUMO level of the substance and that of [Ir(mpptz-diPrp)$_3$], which serves as a dopant, is smaller, an exciplex is more easily formed.

As shown in Example 1, the LUMO level (reduction potential) of 4,6mCzBP2Pm used in the light-emitting layer of the light-emitting element 1 in this example is −2.8 eV (note that 2Ph-4,6mCzBP2Pm used in the comparative light-emitting element 2 has a roughly equal LUMO level). Furthermore, the LUMO level of 4,6mCzP2Pm used in the light-emitting layer of the comparative light-emitting element 3 (−2.88 eV) was obtained by the same method. Because the energy difference between 4,6mCzBP2Pm (2Ph-4,6mCzBP2Pm) and the dopant is smaller than that between 4,6mCzBP2Pm and the dopant, an exciplex is more easily formed and efficiencies can be increased in the light-emitting element 1 (the comparative light-emitting element 2).

When the reduction potential is low like that of 4,6mCzP2Pm used in the comparative light-emitting element 3, the driving voltage of the light-emitting element is low and thus an improvement in reliability can be expected. In the comparative light-emitting element 3, the use of 4,6mCzP2Pm seems to positively influence an improvement in reliability rather than an improvement in efficiencies that accompanies the exciplex formation.

Note that the relation in the LUMO level between the substance and a dopant which are used in combination needs to be considered. It is preferable that the difference between the LUMO level of the substance and that of the dopant be larger than the emission energy of the dopant.

Furthermore, by using different materials in part of the above-described light-emitting elements, a light-emitting element 4 and a comparative light-emitting element 5 which emit light of colors different from those of the above-described light-emitting elements were fabricated. The method for fabricating the light-emitting element 4 and the comparative light-emitting element 5 is not described because it is the same as the method for fabricating the light-emitting element 1 and the comparative light-emitting element 3 except that different materials are used for the light-emitting layers and some layers have different thicknesses. The chemical formula of a material only used in the light-emitting element 4 and the comparative light-emitting element 5 is shown below.

under a nitrogen atmosphere so as not to be exposed to the air (a sealant was applied to surround the elements, and at the time of sealing, UV treatment was performed and heat treatment was performed at 80° C. for 1 hour).

<<Operation Characteristics of Light-Emitting Element 4 and Comparative Light-Emitting Element 5>>

Operation characteristics of the fabricated light-emitting elements were measured. Note that the measurement was carried out at room temperature (in an atmosphere kept at 25° C.).

FIG. 32, FIG. 33, FIG. 34, and FIG. 35 show current density-luminance characteristics, voltage-luminance characteristics, luminance-current efficiency characteristics, and voltage-current characteristics, respectively, of the light-emitting element 4 and the comparative light-emitting element 5.

Table 4 shows initial values of main characteristics of the light-emitting element 4 and the comparative light-emitting element 5 at a luminance of approximately 1000 cd/m$^2$.

TABLE 4

|  | Voltage (V) | Current (mA) | Current density (mA/cm$^2$) | Chromaticity (x, y) | Luminance (cd/m$^2$) | Current efficiency (cd/A) | Power efficiency (lm/W) | External quantum efficiency (%) |
| --- | --- | --- | --- | --- | --- | --- | --- | --- |
| Light-emitting element 4 | 3.1 | 0.040 | 1.0 | (0.32, 0.64) | 1000 | 99 | 100 | 27 |
| Comparative light-emitting element 5 | 3.6 | 0.053 | 1.3 | (0.33, 0.62) | 1100 | 91 | 93 | 25 |

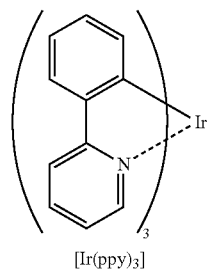

[Ir(ppy)$_3$]

<<Fabrication of Light-Emitting Element 4 and Comparative Light-Emitting Element 5>>

Table 3 shows the element structures of the light-emitting element 4 and the comparative light-emitting element 5 fabricated by the above-described method.

Figure 36:
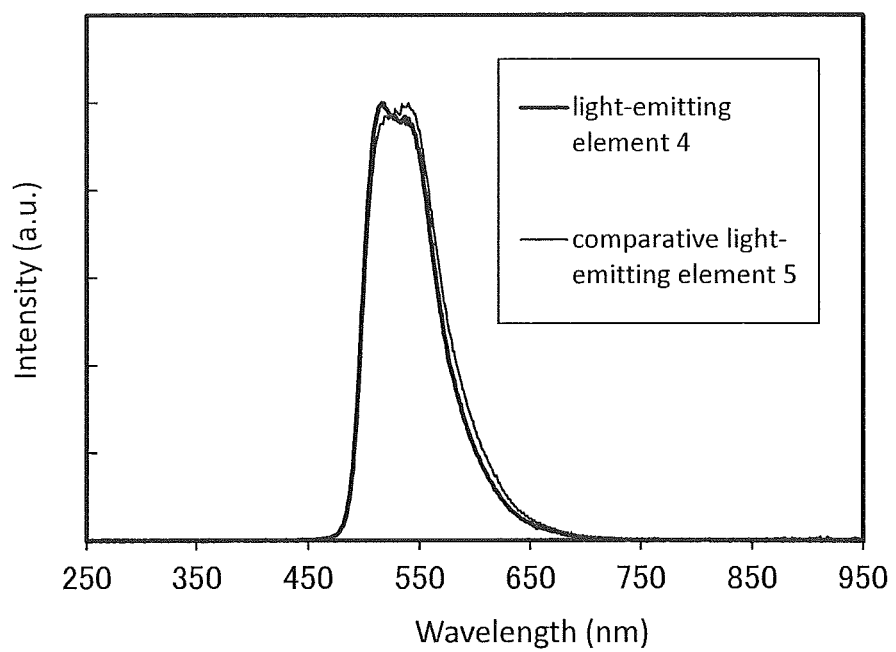
FIG. 36 shows emission spectra of the light-emitting element 4 and the comparative light-emitting element 5.

FIG. 36 shows emission spectra of the light-emitting element 4 and the comparative light-emitting element 5 to which current was applied at a current density of 25 mA/cm$^2$. As shown in FIG. 36, the emission spectra of the light-emitting element 4 and the comparative light-emitting element 5 each have a peak at around 516 nm and it is suggested that the peak is derived from green light emission of the organometallic complex, [Ir(ppy)$_3$], used in the EL layer of each light-emitting element.

Figure 37:
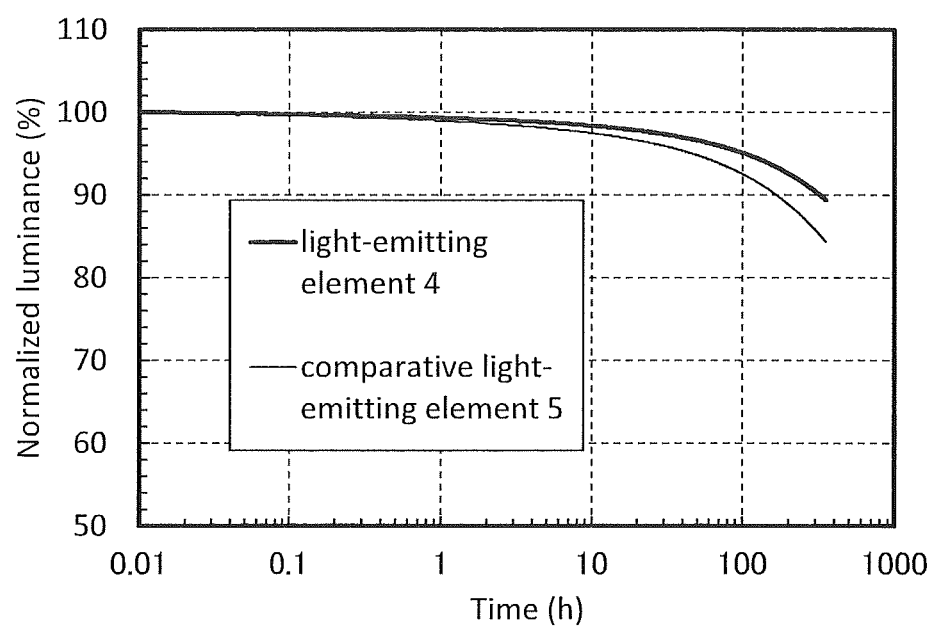
FIG. 37 shows reliability of the light-emitting element 4 and the comparative light-emitting element 5.
Figure 38:
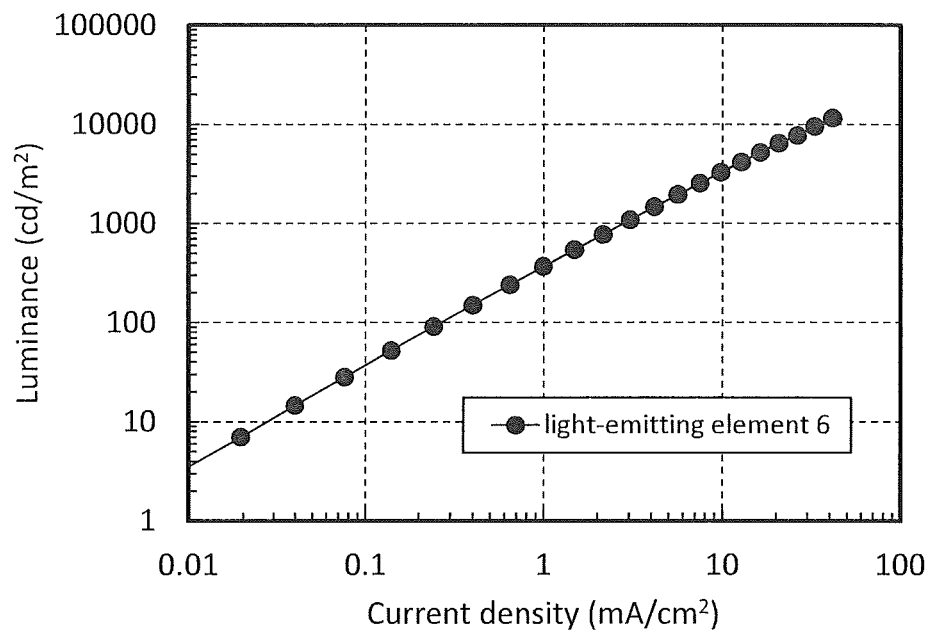
FIG. 38 shows current density-luminance characteristics of a light-emitting element 6.
Figure 39:
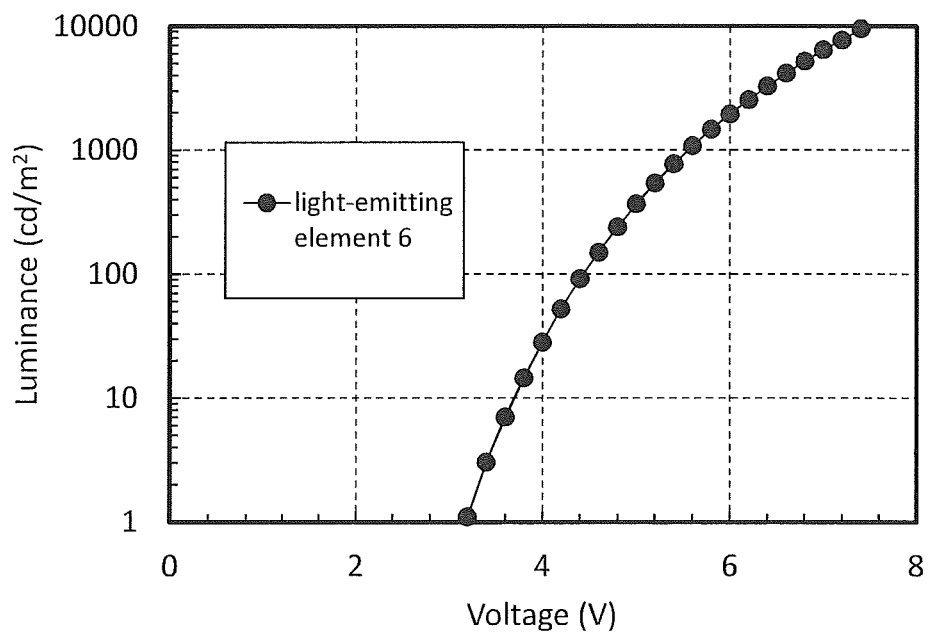
FIG. 39 shows voltage-luminance characteristics of the light-emitting element 6.
Figure 40:
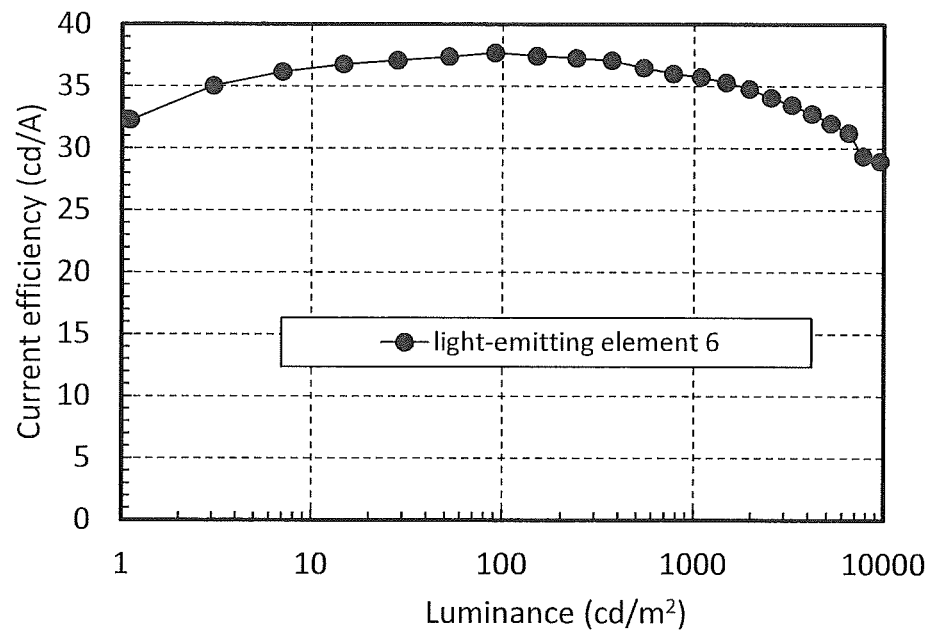
FIG. 40 shows luminance-current efficiency characteristics of the light-emitting element 6.
Figure 41:
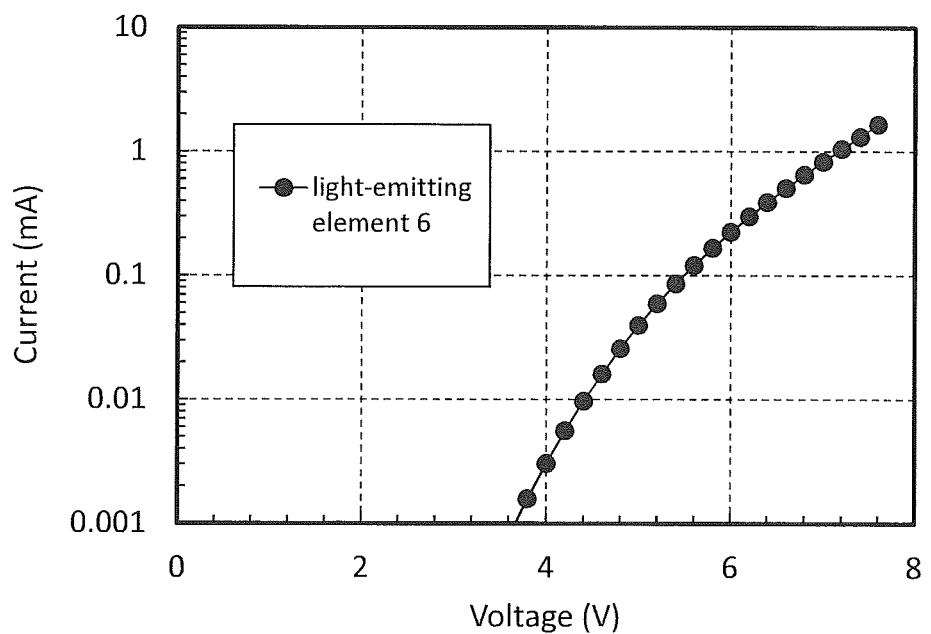
FIG. 41 shows voltage-current characteristics of the light-emitting element 6.

A reliability test was performed on the light-emitting element 4 and the comparative light-emitting element 5. FIG. 37 shows results of the reliability test. In FIG. 37, the vertical axis represents normalized luminance (%) with an initial luminance of 100% and the horizontal axis represents driving time (h) of the light-emitting elements. Note that in the reliability test, the light-emitting element 4 and the comparative light-emitting element 5 were driven under the conditions where the initial luminance was set to 5000 cd/m$^2$ and the current density was constant.

TABLE 3

|  | First electrode | Hole-injection layer | Hole-transport layer | Light-emitting layer | Electron-transport layer | Electron-injection layer | Second electrode |
| --- | --- | --- | --- | --- | --- | --- | --- |
| Light-emitting element 4 | ITO-2 (110 nm) | DBT3P-II:MoOx (4:2, 60 nm) | PCCP (20 nm) | * | 4,6mCzBP2Pm (20 nm) | Bphen (10 nm) | LiF (1 nm) | Al (200 nm) |
| Comparative light-emitting element 5 | ITO-2 (110 nm) | DBT3P-II:MoOx (4:2, 60 nm) | PCCP (20 nm) | ** | 4,6mCzP2Pm (20 nm) | Bphen (10 nm) | LiF (1 nm) | Al (200 nm) |

* 4,6mCzBP2Pm:PCCP:[Ir(ppy)$_3$] (0.5:0.5:0.05 (20 nm)\0.8:0.2:0.05 (20 nm))
** 4,6mCzP2Pm:PCCP:[Ir(ppy)$_3$] (0.5:0.5:0.05 (20 nm)\0.8:0.2:0.05 (20 nm))

The fabricated light-emitting element 4 and the comparative light-emitting elements 5 were sealed in a glove box It is also found from the comparison between the light-emitting element 4 and the comparative light-emitting element 5, which emit green light, shown in Table 4 that the light-emitting element 4 that uses 4,6mCzBP2Pm, which has a biphenyl structure, in the EL layer has higher efficiencies than the comparative light-emitting element 5 that uses 4,6mCzP2Pm, which has a phenyl structure, in the EL layer. Furthermore, the results shown in FIG. 37 show that the light-emitting element 4 has higher reliability than the comparative light-emitting element 5.

EXAMPLE 4

In this example, a light-emitting element 6 that includes 3,5mCzBP2Py (the structural formula (200)), which is a heterocyclic compound of one embodiment of the present invention, was fabricated. The method for fabricating the light-emitting element 6 is not described because the light-emitting element 6 is formed in the same manner as that in Example 3 except that different materials are used for some of the layers. Chemical formulae of materials used in this example are shown below.

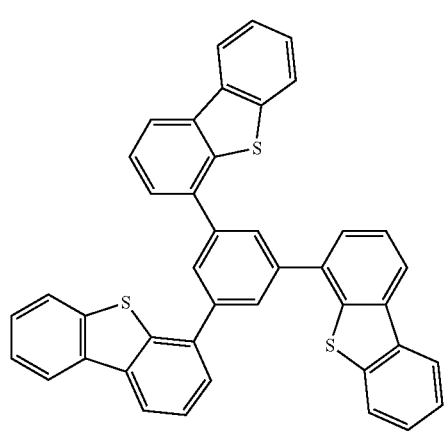

DBT3P-II

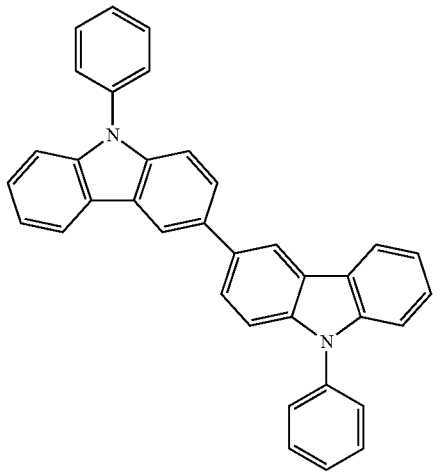

PCCP

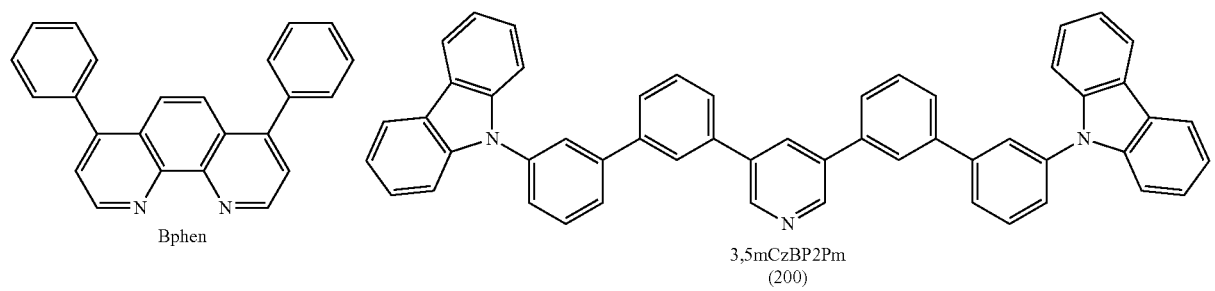

Bphen 3,5mCzBP2Pm
(200)

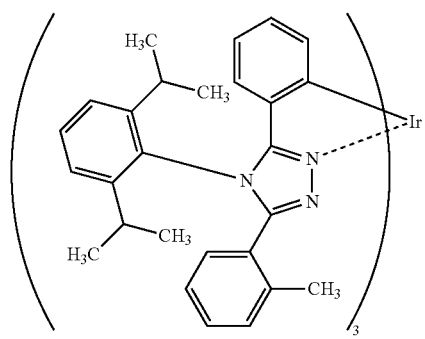

[Ir(mpptz-diPrp)$_3$]

<<Fabrication of Light-Emitting Element 6>>

Table 5 shows the element structure of the light-emitting element 6 fabricated in this example.

TABLE 5

| | First electrode | Hole-injection layer | Hole-transport layer | Light-emitting layer | Electron-transport layer | | Electron-injection layer | Second electrode |
|---|---|---|---|---|---|---|---|---|
| Lift-emitting element 6 | ITO-2 (110 nm) | DBT3P-II:MoOx (4:2, 60 nm) | PCCP (20 mn) | * | 3,5mCzBP2Py (10 nm) | Bphen (15 nm) | LiF (1 nm) | Al (200 nm) |

* PCCP:3,5mCzBP2Py:[Ir(mpptz-diPrp)₃]\3,5mCzBP2Py:[Ir(mpptz-diPrp)₃] (1:0.3:0.06 (30 nm)\1:0.06 (10 nm))

The fabricated light-emitting element 6 was sealed in a glove box under a nitrogen atmosphere so as not to be exposed to the air (a sealant was applied to surround the element, and at the time of sealing, UV treatment was performed and heat treatment was performed at 80° C. for 1 hour).

<<Operation Characteristics of Light-Emitting Element 6>>

Operation characteristics of the fabricated light-emitting element 6 were measured. Note that the measurement was carried out at room temperature (in an atmosphere kept at 25° C.).

FIG. 38, FIG. 39, FIG. 40, and FIG. 41 show current density-luminance characteristics, voltage-luminance characteristics, luminance-current efficiency characteristics, and voltage-current characteristics, respectively, of the light-emitting element 6.

Table 6 shows initial values of main characteristics of the light-emitting element 6 at a luminance of approximately 1000 cd/m².

TABLE 6

| | Voltage (V) | Current (mA) | Current density (mA/cm²) | Chromaticity (x, y) | Luminance (cd/m²) | Current efficiency (cd/A) | Power efficiency (lm/W) | External quantum efficiency (%) |
|---|---|---|---|---|---|---|---|---|
| Light-emitting element 6 | 5.6 | 0.12 | 3.0 | (0.19, 0.33) | 1100 | 36 | 20 | 16 |

Figure 42:
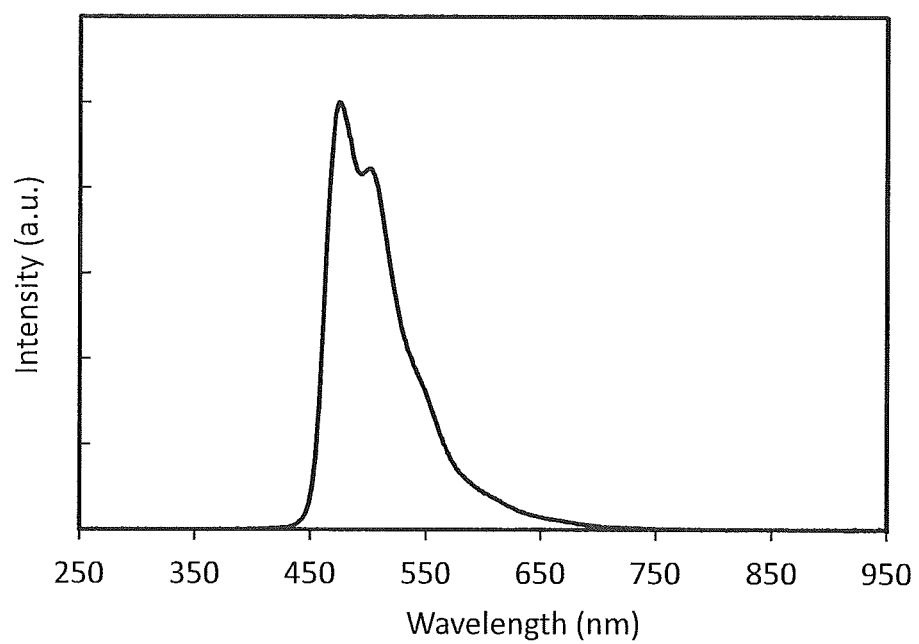
FIG. 42 shows an emission spectrum of the light-emitting element 6.

FIG. 42 shows an emission spectrum of the light-emitting element 6 to which current was applied at a current density of 25 mA/cm². As shown in FIG. 42, the emission spectrum of the light-emitting element 6 has a peak at around 476 nm and it is suggested that the peak is derived from blue light emission of the organometallic complex, [Ir(mpptz-diPrp)₃], used in the EL layer of the light-emitting element.

Figure 43:
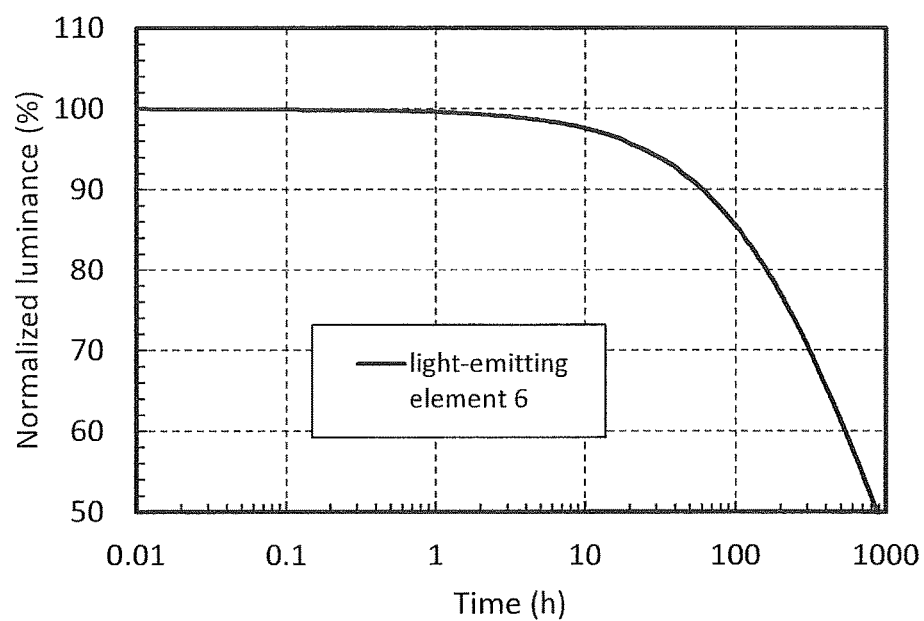
FIG. 43 shows reliability of the light-emitting element 6.

A reliability test was performed on the light-emitting element 6. FIG. 43 shows results of the reliability test. In FIG. 43, the vertical axis represents normalized luminance (%) with an initial luminance of 100% and the horizontal axis represents driving time (h) of the light-emitting element. Note that in the reliability test, the light-emitting element 6 was driven under the conditions where the initial luminance was set to 5000 cd/m² and the current density was constant.

In the light-emitting element 6, 3,5mCzBP2Py, which is one embodiment of the present invention, is used in the EL layer. Note that 3,5mCzBP2Py has a structure in which substituents (substituents that can each bond a heterocyclic group including a carbazole skeleton to the pyridine skeleton via an arylene group) are bonded to the 4- and 6-positions of the pyridine skeleton. As shown by the above results, like the light-emitting element 1 that uses 4,6mCzBP2Pm in the EL layer described in Example 3, the light-emitting element 6 that uses 3,5mCzBP2Py in the EL layer also has high efficiencies and reliability because the substituents at the 4- and 6-positions have biphenyl structures.

This application is based on Japanese Patent Application serial no. 2015-082469 filed with Japan Patent Office on Apr. 14, 2015, the entire contents of which are hereby incorporated by reference.

What is claimed is:

1. A heterocyclic compound represented by a general formula (G1):

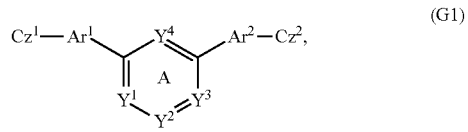

(G1)

wherein each of any one, two, or three of Y¹ to Y⁴ in a ring A represents N, and each of the rest of Y¹ to Y⁴ represents CH, wherein in the case where each of any two or three of the Y¹ to Y⁴ is N, the N of the any two or three of the Y¹ to Y⁴ are not next to each other, wherein Ar¹ represents a substituted or unsubstituted biphenyldiyl group, wherein Ar² represents a substituted or unsubstituted biphenyldiyl group, wherein Cz¹ represents a substituted or unsubstituted heterocyclic group including a carbazole skeleton, wherein Cz² represents a substituted or unsubstituted heterocyclic group including a carbazole skeleton, wherein the carbazole skeleton included in the Cz¹ is directly bonded to the Ar¹, and wherein the carbazole skeleton included in the Cz² is directly bonded to the Ar².

2. A heterocyclic compound represented by a general formula (G1):

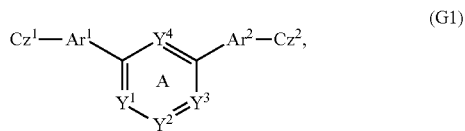
(G1)

wherein each of any one or two of $Y^1$ to $Y^4$ in a ring A represents N, and each of the rest of $Y^1$ to $Y^4$ represents CH, wherein in the case where each of two of the $Y^1$ to $Y^4$ is N, each of $Y^1$ and $Y^3$ is N, wherein $Ar^1$ represents a substituted or unsubstituted biphenyldiyl group, wherein $Ar^2$ represents a substituted or unsubstituted biphenyldiyl group, wherein $Cz^1$ represents a substituted or unsubstituted heterocyclic group including a carbazole skeleton, wherein $Cz^2$ represents a substituted or unsubstituted heterocyclic group including a carbazole skeleton, wherein the carbazole skeleton included in the $Cz^1$ is directly bonded to the $Ar^1$, and wherein the carbazole skeleton included in the $Cz^2$ is directly bonded to the $Ar^2$.

3. The heterocyclic compound according to claim 1,
wherein in the general formula (G1), the $Ar^1$ represents a substituted or unsubstituted biphenyl-3,3'-diyl group and the $Ar^2$ represents a substituted or unsubstituted biphenyl-3,3'-diyl group.

4. A heterocyclic compound represented by a general formula (G2):

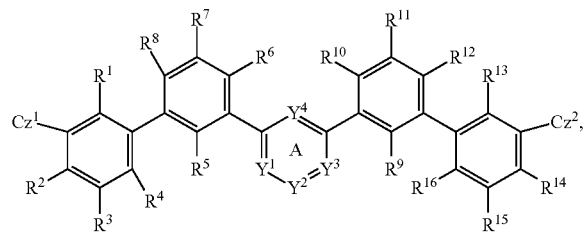
(G2)

wherein each of any one, two, or three of $Y^1$ to $Y^4$ in a ring A represents N, and each of the rest of $Y^1$ to $Y^4$ represents CH, wherein in the case where each of any two or three of the $Y^1$ to $Y^4$ is N, the N of the any two or three of the $Y^1$ to $Y^4$ are not next to each other, wherein $Cz^1$ represents a substituted or unsubstituted heterocyclic group including a carbazole skeleton, wherein $Cz^2$ represents a substituted or unsubstituted heterocyclic group including a carbazole skeleton, wherein the carbazole skeleton included in the $Cz^1$ and the carbazole skeleton included in the $Cz^2$ are directly bonded to different phenyl groups from each other, and wherein each of $R^1$ to $R^{16}$ independently represents any one of hydrogen, an alkyl group having 1 to 6 carbon atoms, an alkoxy group having 1 to 6 carbon atoms, and an aryl group having 6 to 12 carbon atoms.

5. A heterocyclic compound represented by a general formula (G2):

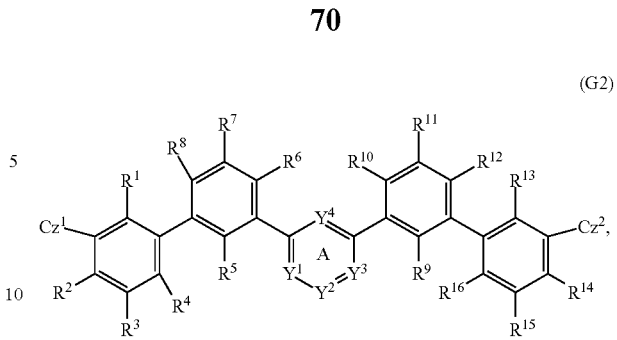
(G2)

wherein each of any one or two of $Y^1$ to $Y^4$ in a ring A represents N, and each of the rest of $Y^1$ to $Y^4$ represents CH, wherein in the case where each of two of the $Y^1$ to $Y^4$ is N, each of $Y^1$ and $Y^3$ is N, wherein $Cz^1$ represents a substituted or unsubstituted heterocyclic group including a carbazole skeleton, wherein $Cz^2$ represents a substituted or unsubstituted heterocyclic group including a carbazole skeleton, wherein the carbazole skeleton included in the $Cz^1$ and the carbazole skeleton included in the $Cz^2$ are directly bonded to different phenyl groups from each other, and wherein each of $R^1$ to $R^{16}$ independently represents any one of hydrogen, an alkyl group having 1 to 6 carbon atoms, an alkoxy group having 1 to 6 carbon atoms, and an aryl group having 6 to 12 carbon atoms.

6. The heterocyclic compound according to claim 1,
wherein the heterocyclic compound is represented by a general formula (G3):

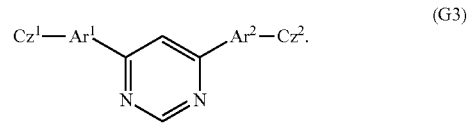
(G3)

7. The heterocyclic compound according to claim 6,
wherein in the general formula (G3), the $Ar^1$ represents a substituted or unsubstituted biphenyl-3,3'-diyl group and the $Ar^2$ represents a substituted or unsubstituted biphenyl-3,3'-diyl group.

8. A heterocyclic compound represented by a general formula (G4):

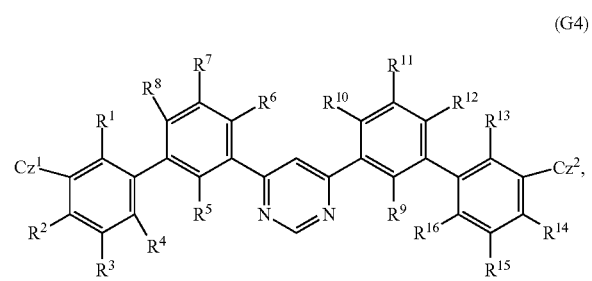
(G4)

wherein $Cz^1$ represents a substituted or unsubstituted heterocyclic group including a carbazole skeleton, wherein $Cz^2$ represents a substituted or unsubstituted heterocyclic group including a carbazole skeleton, wherein the carbazole skeleton included in the $Cz^1$ and the carbazole skeleton included in the $Cz^2$ are directly bonded to different phenyl groups from each other, and wherein each of $R^1$ to $R^{16}$ independently represents any one of hydrogen, an alkyl group having 1 to 6 carbon atoms, an alkoxy group having 1 to 6 carbon atoms, and an aryl group having 6 to 12 carbon atoms.

9. The heterocyclic compound according to claim 1, wherein the heterocyclic compound is represented by a general formula (G5):

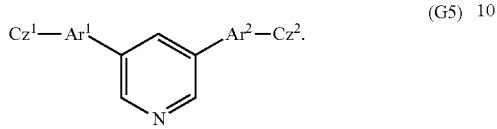

(G5)

10. The heterocyclic compound according to claim 9, wherein in the general formula (G5), the $Ar^1$ represents a substituted or unsubstituted biphenyl-3,3'-diyl group and the $Ar^2$ represents a substituted or unsubstituted biphenyl-3,3'-diyl group.

11. A heterocyclic compound represented by a general formula (G6):

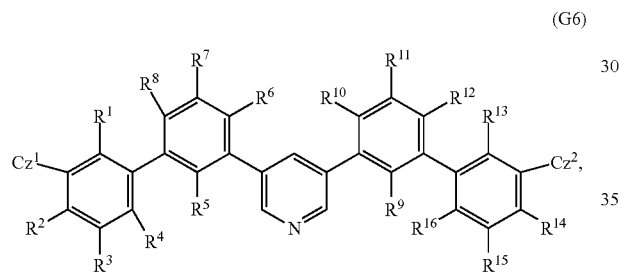

(G6)

wherein $Cz^1$ represents a substituted or unsubstituted heterocyclic group including a carbazole skeleton,
wherein $Cz^2$ represents a substituted or unsubstituted heterocyclic group including a carbazole skeleton,
wherein the carbazole skeleton included in the $Cz^1$ and the carbazole skeleton included in the $Cz^2$ are directly bonded to different phenyl groups from each other, and
wherein each of $R^1$ to $R^{16}$ independently represents any of hydrogen, an alkyl group having 1 to 6 carbon atoms, an alkoxy group having 1 to 6 carbon atoms, and an aryl group having 6 to 12 carbon atoms.

12. The heterocyclic compound according to claim 1, wherein in the general formula (G1), N in the carbazole skeleton included in the $Cz^1$ is directly bonded to the $Ar^1$, and N in the carbazole skeleton included in the $Cz^2$ is directly bonded to the $Ar^2$.

13. The heterocyclic compound according to claim 1, wherein in the general formula (G1), the $Cz^1$ represents a substituted or unsubstituted carbazolyl group and the $Cz^2$ represents a substituted or unsubstituted carbazolyl group.

14. The heterocyclic compound according to claim 13, wherein at least one of the carbazolyl groups is a N-carbazolyl group.

15. The heterocyclic compound according to claim 1, wherein at least one of the heterocyclic groups is represented by a general formula (α):

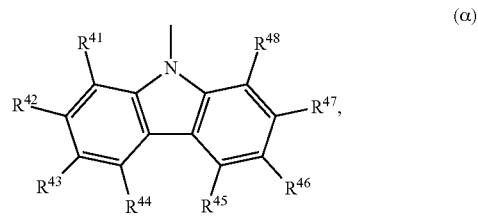

(α)

wherein each of $R^{41}$ to $R^{48}$ independently represents any one of hydrogen, an alkyl group having 1 to 6 carbon atoms, an alkoxy group having 1 to 6 carbon atoms, a hydroxyl group, a sulfanyl group, an arylamino group having 6 to 12 carbon atoms, a vinyl group, and an aryl group having 6 to 12 carbon atoms, and
wherein any adjacent substituents among the $R^{41}$ to $R^{48}$ are capable of being bonded to each other to form a ring.

16. The heterocyclic compound according to claim 1, wherein at least one of the heterocyclic groups is an unsubstituted N-carbazolyl group.

17. The heterocyclic compound according to claim 1, wherein the heterocyclic compound is represented by a structural formula (100):

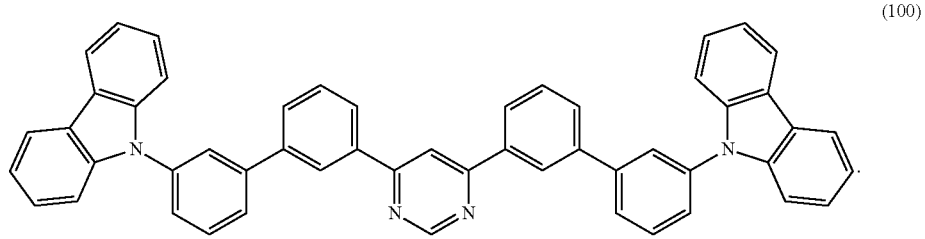 [SMILES: c1cc(-c2cccc(-n3c4ccccc4c4ccccc43)c2)cc(-c2cc(-c3cccc(-c4cccc(-n5c6ccccc6c6ccccc65)c4)c3)ncn2)c1]

(100)

18. The heterocyclic compound according to claim 1, wherein the heterocyclic compound is represented by a structural formula (200):

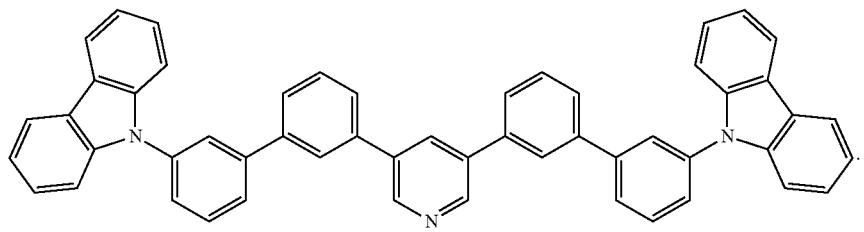

(200)

19. A light-emitting element comprising the heterocyclic compound according to claim 1.

20. A light-emitting element comprising the heterocyclic compound according to claim 1,
wherein the light-emitting element comprises an EL layer between a pair of electrodes, and
wherein the EL layer comprises the heterocyclic compound.

21. A light-emitting element comprising the heterocyclic compound according to claim 1,
wherein the light-emitting element comprises an EL layer between a pair of electrodes, the EL layer comprising a light-emitting layer, and
wherein the EL layer comprises the heterocyclic compound.

22. A light-emitting element comprising the heterocyclic compound according to claim 1,
wherein the light-emitting element comprises an EL layer between a pair of electrodes, the EL layer comprising a light-emitting layer,
wherein the light-emitting layer comprises three or more kinds of organic compounds, and
wherein at least one of the three or more kinds of organic compounds is the heterocyclic compound.

23. A light-emitting device comprising the light-emitting element according to claim 19,
wherein the light-emitting device comprises one of a transistor and a substrate.

24. An electronic device comprising the light-emitting device according to claim 23,
wherein the electronic device comprises one of a microphone, a camera, an operation button, an external connection portion, and a speaker.

25. A lighting device comprising the light-emitting element according to claim 19,
wherein the lighting device comprises one of a transistor, a substrate and a sealing substrate.

* * * * *